US009999664B2

(12) United States Patent
Wilson et al.

(10) Patent No.: US 9,999,664 B2
(45) Date of Patent: Jun. 19, 2018

(54) HIV-1 GP120 MINI V3 LOOP AND USES THEREOF

(71) Applicant: The Scripps Research Institute, La Jolla, CA (US)

(72) Inventors: Ian A. Wilson, La Jolla, CA (US); Robyn L. Stanfield, San Diego, CA (US); Robert Pejchal, Lyme, NH (US)

(73) Assignee: The Scripps Research Institute, La Jolla, CA (US)

( * ) Notice: Subject to any disclaimer, the term of this patent is extended or adjusted under 35 U.S.C. 154(b) by 247 days.

(21) Appl. No.: 14/251,070

(22) Filed: Apr. 11, 2014

(65) Prior Publication Data

US 2014/0302081 A1    Oct. 9, 2014

Related U.S. Application Data

(63) Continuation-in-part of application No. PCT/US2012/059734, filed on Oct. 11, 2012.

(60) Provisional application No. 61/546,347, filed on Oct. 12, 2011.

(51) Int. Cl.
| | |
|---|---|
| *A61K 39/21* | (2006.01) |
| *C07K 14/005* | (2006.01) |
| *C07K 16/10* | (2006.01) |
| *C07K 16/44* | (2006.01) |
| *A61K 39/12* | (2006.01) |
| *G01N 33/569* | (2006.01) |

(52) U.S. Cl.
CPC ............. *A61K 39/21* (2013.01); *A61K 39/12* (2013.01); *C07K 14/005* (2013.01); *C07K 16/1063* (2013.01); *C07K 16/44* (2013.01); *G01N 33/56983* (2013.01); *C07K 2317/21* (2013.01); *C07K 2317/34* (2013.01); *C07K 2317/55* (2013.01); *C07K 2317/76* (2013.01); *C12N 2740/15034* (2013.01); *C12N 2740/16034* (2013.01); *C12N 2740/16122* (2013.01); *C12N 2740/16134* (2013.01); *G01N 33/56988* (2013.01)

(58) Field of Classification Search
CPC ................. A61K 39/21; C07K 14/005; G01N 33/56988; C12N 2740/16134; C12N 2740/16122
See application file for complete search history.

(56) References Cited

U.S. PATENT DOCUMENTS

| | | | | |
|---|---|---|---|---|
| 7,022,324 B2* | 4/2006 | Binley | .................... | C12N 7/00 424/188.1 |
| 2007/0224211 A1 | 9/2007 | Wang | | |
| 2008/0181913 A1 | 7/2008 | Dwek et al. | | |
| 2009/0191235 A1 | 7/2009 | Kwong et al. | | |

OTHER PUBLICATIONS

Fitch, W. M., May 2000, Homology a personal view on some of the problems, TIG 16(5):227-231.*
TheiBen, G., Feb. 2002, Secret life of genes, Nature 415:741.*
Ivanoff, L. A., et al., 1991, Alteration of HIV-1 infectivity and neutralization by a single amino acid replacement in the V3 loop domain, AIDS Res. Human Retrovir. 7(7):595-606.*
Lee, S.-K., et al., 2000, A single point mutation in HIV-1 V3 loop alters the immunogenic properties of rgp120, Arch. Virol. 145:2087-2103.*
West, Jr., A. P., et al., 2014, Structural insights on the role of antibodies in HIV-1 vaccine and therapy, Cell 156:633-648.*
Walker, B. D., and D. R. Burton, 2008, Toward an AIDS vaccine, Science 320:760-764.*
Barouch, D. H., 2008, Challenges in the development of an HIV-1 vaccine, Nature 455:613-619.*
Letvin, N. L., and Walker, B. D., 2003, Immunopathogenesis and immunotherapy in AIDS virus infections, Nat. Med. 9(7):861-866.*
Supplementary European Search Report dated Jul. 3, 2015, which issued during prosecution of European Application No. EP 12 84 0238.
Doores, et al. "Envelope glycans of immunodeficiency virions are almost entirely oligomannose antigens" Proceedings of the National Academy of Sciences 107(31):13800-13805, Aug. 3, 2010.
Geng, et al. "In Pursuit of Carbohydrate-Based HIV Vaccines, Part 2: The Total Synthesis of High-Mannose-Type gp120 Fragments—Evaluation of Strategies Directed to Maximal Convergence" Angewandte Chemie 116 (19):2616-2619, May 3, 2004.
Joyce, et al. "An oligosaccharide-based HIV-1 2G12 mimotope vaccine induces carbohydrate-specific antibodies that fail to neutralize HIV-1 virions" Proceedings of the National Academy of Sciences 105(41):15684-15689, Oct. 6, 2008.

(Continued)

*Primary Examiner* — Jeffrey Parkin
(74) *Attorney, Agent, or Firm* — Vedder Price P.C.; Thomas J. Kowalski; Deborah L. Lu

(57) ABSTRACT

The invention relates to an immunogenic HIV-1 gp120 mini V3 loop, which is a truncated version of the full-length gp120 V3 loop useful for crystallization with antibodies that recognize carbohydrate moieties. The invention also relates to the structure of a broadly neutralizing antibody as a complex with a glycosylated gp120 outer domain, as determined by crystallographic techniques, and the confirmation that a glycosylated gp120 outer domain has a functional relevant conformation, as well as the determination of key residues on a glycosylated gp120 outer domain, and uses thereof and compounds and compositions therefrom. Furthermore, the invention also relates to other peptides and mimetic peptides, which bind to broadly neutralizing antibodies.

10 Claims, 30 Drawing Sheets

(30 of 30 Drawing Sheet(s) Filed in Color)

(56) References Cited

OTHER PUBLICATIONS

Mandal, et al. "In pursuit of Carbohydrate-Based HIV Vaccines, Part 1: The Total Synthesis of Hybrid-Type gp120 Fragment" Angewandte Chemie International Edition 43(19).2557-2561, Jan. 1, 2004.

Walker, et al "Broad neutralization coverage HIV by multiple highly potent antibodies" Nature 477 (7365):406-470, Sep. 22, 2011.

Resik, S. et. al. HIV-1 clone 82-00 from Cuba envelope glycoprotein (env) gene, partial cds. ENBL Database Entry DQ320410 [online] Apr. 20, 2007 [Retrieved on Jan. 8, 2013], http://www/ebi.ac.uk/Tools/dbfetch/emblfetch?style=html&id=DQ320410&Submit=Go> , pp. 1-2.

Pejchal, R. et. al., "A Potent and Broad Neutralizing Antibody Recognizes and Penetrates the HIV Glycan Shield," Science, vol. 334, pp. 1097-1103. Oct. 13, 2011.

\* cited by examiner

B

| Antibody | JR-FL cell surface binding (EC$_{50}$) (nM) | JR-FL neutralization (IC$_{50}$) (nM) | EC$_{50}$/IC$_{50}$ |
|---|---|---|---|
| PGT 127 Fab | 12.7 | 14.6 | 0.87 |
| PGT 127 IgG | 3.1 | 0.18 | 17.2 |
| PGT 128 Fab | 10.3 | 6.3 | 1.63 |
| PGT 128 IgG | 2.8 | 0.09 | 31.1 |
| 2G12 IgG | 11.6 | 8.5 | 1.36 |

C

D

A

B

| Glycosidic Linkage | Dihedral angle (°) | | |
|---|---|---|---|
| | φ | ψ | ω |
| Man(α1→2)Man Library Conf. #1 | 62.2 ±8.3 | −175.0 ±10.3 | - |
| Man(α1→2)Man Library Conf. #2 | 71.9 ±13.3 | −104.4 ±15.4 | - |
| D1(α1→2)C | 82.1 | −104.0 | - |
| C(α1→2)4 | 71.1 | −93.1 | - |
| D3(α1→2)B | 78.9 | −95.2 | - |
| Man(α1→3)Man Library | 72.5 ±11.0 | −112.3 ±22.5 | - |
| A(α1→3)4' | 97.8 | −96.0 | - |
| 4(α1→3)3 | 77.1 | −139.0 | - |
| Man(α1→6)Man Library Conf. #1 | 65.4 ±9.0 | 182.6 ±5.1 | 66.4 ±10.2 |
| Man(α1→6)Man Library Conf. #2 | 66.5 ±10.8 | 186.7 ±15.1 | 185.0 ±11.2 |
| Man(α1→6)Man Library Conf. #3 | 67.4 ±14.4 | 109.1 ±13.7 | 203.0 ±22.7 |
| B(α1→3) 4' | 51.6 | 171.4 | 55.3 |
| 4'(α1→3)3 | 83.9 | −174.9 | 63.9 |

```
1-40      DTITLPCRPAPPPHCSSNITGLILTRDGGNSNNESEIFRP 41-80     GGGDMRDIARCQIAGTVVSTQLLLNGSLAEEEVVIRSVNF

|--*----mV3------|
81-120    TDNAKSICVQLNTSVEINCTRPNNTRPGEIIGDIRQAHC

•
121-160   NISRAKWNNTLKQIASKLREQFGNNKTIIFKQSSGGDPEI 161-190   VTHSFNCGGEFFYCDSTQLFNSTWFNSTWS
```

HIV-1 GP120 MINI V3 LOOP AND USES THEREOF

RELATED APPLICATIONS AND INCORPORATION BY REFERENCE

This application is a continuation-in-part of international patent application Serial No. PCT/US2012/059734 filed 11 Oct. 2012, which published as PCT Publication No. WO 2013/055908 on 18 Apr. 2013, which claims priority to U.S. provisional patent application Ser. No. 61/546,347 filed Oct. 12, 2011. Reference is also made to international patent application Serial No. PCT/US11/49880 filed Aug. 31, 2011.

FEDERAL FUNDING LEGEND

This invention was made with government support under Grant No. AI084817, AI074372 and AI082362 awarded by the National Institutes of Health. The federal government has certain rights to this invention.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE LISTING

The instant application contains a Sequence Listing which has been submitted electronically in ASCII format and is hereby incorporated by reference in its entirety. Said ASCII copy, created on Aug. 2, 2016, is named 43094_01_2020 SL.txt and is 3,579 bytes in size.

FIELD OF THE INVENTION

The present invention relates to an HIV-1 gp120 mini V3 loop, which is a truncated version of the full-length gp120 V3 loop useful for crystallization with antibodies that recognize carbohydrate moieties located at the base of the V3 loop. A composition containing the mini V3 loop, when administered, may elicit anti-HIV antibodies, in particular broadly neutralizing antibodies. The composition containing the mini V3 loop may then be used in diagnostic, pharmaceutical, immunogenic, immunological or vaccine compositions. These compositions are useful in the detection or treatment and/or prevention of HIV infections. Further, antibodies elicited by such compounds also can be used in diagnostic or pharmaceutical, immunogenic, immunological or vaccine compositions.

BACKGROUND OF THE INVENTION

Viruses have evolved a variety of mechanisms to escape antibody recognition, many of which involve features of the viral surface proteins, such as high variability, steric occlusion, and glycan coating. For HIV, the dense shield of glycans that decorate the viral Env protein was once believed to be refractory to antibody recognition, shielding conserved protein epitopes of important functional significance whose greater exposure would result in increased susceptibility to antibody neutralization.

However, bnMAb 2G12 and several PGT antibodies appear to bind directly to the HIV glycan coat. Although carbohydrate-protein interactions are typically weak, 2G12 recognizes terminal Man$\alpha$1,2Man moieties on oligomannose glycans using a unique domain-exchanged antibody structure that creates a multivalent binding surface and enhances the affinity of the interaction through avidity effects.

However, although 2G12 neutralizes clade B isolates broadly, it is less effective against other clades, in particular clade C viruses that have a somewhat different oligomannose glycan arrangement to clade B viruses. In contrast, Applicants have recently isolated at least six bnMAbs (PGTs 125-128, 130-131) that bind specifically to the Man$_{8/9}$ glycans on gp120 and neutralize across clades with exceptional breadth and potency. PGT 128, the broadest of these antibodies, neutralizes over 70% of globally circulating viruses and is, on average, an order of magnitude more potent than the recently described PG9, PG16, VRC01, and VRC-PG04 bnMAbs and two orders of magnitude more potent than prototype bnMAbs described earlier.

Citation or identification of any document in this application is not an admission that such document is available as prior art to the present invention.

SUMMARY OF THE INVENTION

The present invention relates to an HIV-1 gp120 mini V3 loop which may be a truncated version of the full-length gp120 V3 loop. In an advantageous embodiment, the sequence of a mini V3 loop may be: 295-NCTRPNNNTR PGEIIGDIRQAHCN-332 (SEQ ID NO: 1). SEQ ID NO: 1 corresponds to residues 295-304, an inserted Proline (underlined), and residues 321-332 from the JR-FL strain of gp120. This truncated V3 loop may be used in gp120, gp120 core, and gp120 outer domain constructs in place of full-length V3.

Constructs containing mini-V3 may be useful for crystallization with antibodies that recognize carbohydrates at N295, N301, and N332, and other and other, adjoining carbohydrates in the vicinity, such as N392, N301, and N332, and these constructs may also be useful for eliciting broadly neutralizing antibodies. The tip of full-length V3 (around residues 303-319) is highly immunogenic, but usually elicits type-specific or non-neutralizing antibodies, so the removal of that part of the V3 loop may eliminate type-specific and/or non-neutralizing responses against those residues. Constructs that bind highly potent broadly neutralizing antibodies may be tested as immunogens in animal models to aid in vaccine design to elicit the same types of antibodies in humans.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DEPOSITS

Coordinates and structure factors for the Fab PGT 128/Man$_9$, Fab PGT 127/Man$_9$, and Fab PGT 128/eODmV3 structures have been deposited with the PDB under accession codes 3TV3, 3TWC, and 3TYG. The Fab PGT 128/d664G trimer EM reconstruction density has been deposited with the EMDB under accession code EMD-1970.

The Deposits were made pursuant to the terms of the Budapest Treaty. Upon issuance of a patent, all restrictions upon the deposit will be removed, and the deposit is intended to meet the requirements of 37 CFR §§ 1.801-1.809. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The following detailed description, given by way of example, but not intended to limit the invention solely to the specific embodiments described, may best be understood in conjunction with the accompanying drawings.

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
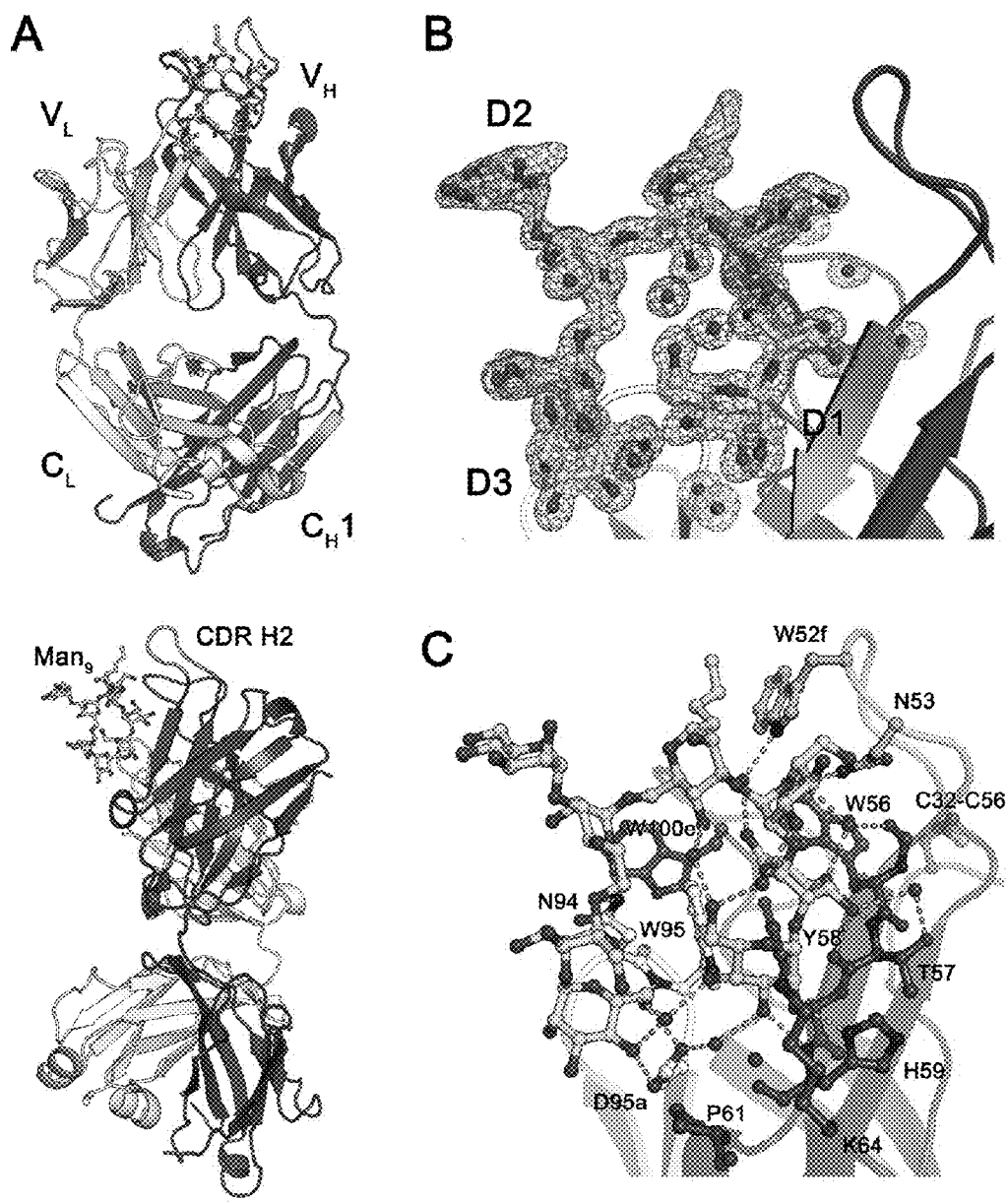
FIG. 1. Unique binding mode of Man$_9$ by antibody PGT 128 revealed by the high-resolution crystal structure of the complex. (A) Front (top) and side (bottom) views of PGT 128 Fab with bound Man$_9$ glycan. The light and heavy chains are depicted as grey and magenta ribbons, respectively, and the glycan as yellow and red sticks. (B) Close-up view of glycan binding site of PGT 128 showing electron density (2Fo-Fc) at 1.0 sigma for glycan and associated water molecules. Water molecules are shown as red spheres, electron density is colored red for waters that bridge mannose residues and green for glycan-antibody interfacial positions. (C) Detailed view of the tryptophan-rich ($V_H$ W52f, W56, W100e and $V_L$ W95) and Asn/Asp-rich ($V_H$ N53, $V_L$ N94, D95a) glycan binding site at the interface of CDRs H2, H3, L3 and FR2. The D1 arm is bound by residues in the 6-amino acid CDR H2 insert and $V_H$ FR2. The D3 arm is bound by residues within CDR L3. Potential hydrogen bonds are shown as green dashes.

The present invention relates to an HIV-1 gp120 mini V3 loop which may be a truncated version of the full-length gp120 V3 loop. In an advantageous embodiment, the sequence of a mini V3 loop may be: 295-NCTRPNNNTR PGEIIGDIRQAHCN-332 (SEQ ID NO: 1). SEQ ID NO: 1 corresponds to residues 295-304, an inserted Proline (underlined), and residues 321-332 from the JR-FL strain of gp120. This truncated V3 loop may be used in gp120, gp120 core, and gp120 outer domain constructs in place of full-length V3.

The V3 loop is very flexible, so deleting it from gp120 constructs often aids in their crystallization. However the carbohydrate attachment sites at N295, N301, and N332 are essential for recognition from some of the PGT series of antibodies, so a shortened V3 loop was designed to include the glycosylation sites, and also reduce flexibility. Therefore, a modified sequence of SEQ ID NO: 1 is envisioned with amino acid substitutions maintaining carbohydrate attachment sites at N295, N301, and N332 as well as an inserted proline or other similar amino acid residue to introduce rigidity to the peptide.

Constructs containing SEQ ID NO: 1 may be useful for crystallization with antibodies that recognize or are dependent on carbohydrates at N295, N301, and N332, and other, adjoining carbohydrates in the vicinity, and these constructs may also be useful for eliciting broadly neutralizing antibodies. The tip of full-length V3 (around residues 303-319) is highly immunogenic, but usually elicits type-specific or non-neutralizing antibodies, so the removal of that part of the V3 loop may eliminate a type-specific and non-neutralizing responses against those residues. Constructs that bind highly potent broadly neutralizing antibodies may be tested as immunogens in animal models to aid in vaccine design to elicit the same types of antibodies in humans.

Additionally, the invention pertains to the identification, design, synthesis and isolation of SEQ ID NO: 1. The present invention also relates to homologues, derivatives and variants of SEQ ID NO: 1, wherein it is preferred that the homologue, derivative or variant have at least 50%, at least 60%, at least 70%, at least 75%, at least 80%, at least 85%, at least 90%, at least 93%, at least 95%, at least 97%, at least 98% or at least 99% homology or identity with the sequence of SEQ ID NO: 1. It is noted that within this specification, homology to SEQ ID NO: 1 refers to the homology of the homologue, derivative or variant to the binding site of SEQ ID NO: 1.

The mini-V3 was designed, and incorporated into several different constructs, including the gp120 outer domain, gp120 core (strains JR-FL, JR-CSF, 92RW020, 93IN905), and a fusion protein between human Fc and mini-V3. Other regions of the gp120 protein are contemplated such as an inner domain and a bridging sheet or beta sheet.

The present invention also contemplates the crystallization of a composition or construct containing SEQ ID NO: 1 with a broadly neutralizing antibody such as, but not limited to, 1443_C16 (PG16) (TCN-116), 1503 H05 (PG16) (TCN-119), 1456 A12 (PG16) (TCN-117), 1469 M23 (PG16) (TCN-118), 1489_I13 (PG16) (TCN-120), 1480_I08 (PG16), 1456_P20 (PG20), 1460_G14 (PGG14), 1495_C14 (PGC14), 1496_C09 (PG9) (TCN-109), 4838_L06 (PGT-121), 4873_E03 (PGT-121), 4877_D15 (PGT-122), 4858_P08 (PGT-123), 6123_A06 (PGT-125), 5141_B17 (PGT-126), 5145_B14 (PGT-127), 5114_A19 (PGT-128), 5147_N06 (PGT-130), 5136_H01 (PGT-131), 5343_B08 (PGT-135), 5344_E16 (PGT-135), 5329_C19 (PGT-136), 5366_P21 (PGT-136), 4964_G22 (PGT-141), 5345_I01 (PGT-137), 4993_K13 (PGT-141), 4995_E20 (PGT-142), 4980_N08 (PGT-143), 4970_K22 (PGT-144), 4995_P16 (PGT-145), 4835_F12 (PGT-124), 4869-K15

(PGT-133), 4876_M06 (PGT-134), 5131_A17 (PGT-132), 5138_G07 (PGT-138), 5120_N10 (PGT-139), 6831_A21 (PGT-151), 6889_I17 (PGT-152), 6891_F06 (PGT-153), 6843_G20 (PGT-154), 6892_D19 (PGT-155), 6808_B09 (PGT-156), 6892_C23 (PGT-157), and 6881 N05 (PGT-158) and sister clones thereof. For instance, an exemplary sister clone of the 1443_C16 (PG16) (TCN-116) antibody is the 1503 H05 (PG16) (TCN-119) antibody, the 1456 A12 (PG16) (TCN-117) antibody, the 1469 M23 (PG16) (TCN-118) antibody, the 1489_I13 (PG16) (TCN-120) antibody, or the 1480_I08 (PG16) antibody (see, e.g., international patent application Serial No. PCT/US11/49880 filed Aug. 31, 2011, the disclosure of which is incorporated by reference).

As discussed herein and illustrated in the Figures, the invention pertains to the structure of PGT 127 or PGT 128, e.g., as a complex with SEQ ID NO: 1, eODmV3 or $Man_9$ glycan, as determined by crystallographic techniques, and to the confirmation that SEQ ID NO: 1, eODmV3 or $Man_9$ glycan has a functional relevant conformation, as well as to the determination of key residues on PGT 127 or PGT 128. As likewise discussed herein, the present invention thus provides a means for identifying or designing compounds, such as peptides or derivatized peptides (e.g., glycosylated peptides) that bind to the antibody (such as, for example, SEQ ID NO: 1). Similarly, the present invention also provides a means for identifying or designing compounds that bind to the SEQ ID NO: 1, eODmV3 or $Man_9$ or Man-rich glycan binding domains in the antibody. The design of these compounds that act as an immunogen is based on the crystal structure described herein. These compounds, when administered, elicit anti-HIV antibodies. The compounds may then be used in diagnostic, pharmaceutical, immunogenic, immunological or vaccine compositions. These compositions are useful in the detection or treatment and/or prevention of HIV infections. And, antibodies elicited by such compounds also can be used in diagnostic or pharmaceutical, immunogenic, immunological or vaccine compositions.

The invention still further relates to nucleic acid sequences expressing SEQ ID NO: 1, or homologues, variants or derivatives thereof. One of skill in the art will know, recognize and understand techniques used to create such. Additionally, one of skill in the art will be able to incorporate such a nucleic acid sequence into an appropriate vector, allowing for production of the amino acid sequence of SEQ ID NO: 1 or a homologue, variant or derivative thereof. In particular, SEQ ID NO: 1 may further comprise glycans, advantageously $Man_{8/9}GlcNAc_2$ and/or $Man_{8/9}GlcNAc_2$. $Man_{8/9}GlcNAc_2$ may be attached to N332 and/or $Man_{8/9}$ $GlcNAc_2$ may be attached to N301. Other glycan binding sites include, but are not limited to, N295 and N392 on the V3 loop or a corresponding position thereto. Other glycans that are contemplated include, but are not limited to, $Man_8$, $Man_9$ or $Man_9$-oligodendrons, mannose-rich (Man-rich) glycans and modified non-natural glycan that mimic Man glycans.

Glycan microarray analysis (Consortium for Functional Glycomics, CFG, v 5.0) previously revealed that PGT MAbs 125, 126, 127, 128, and 130 contact $Man_8$ (313), $Man_8GlcNAc_2$ (193), $Man_9$ (314) and $Man_9GlcNAc_2$ (194) glycans directly. PGT-131 showed no detectable binding to the CFG glycan array but bound to $Man_9$-oligodendrons.

Additional glycans that bind broadly neutralizing antibodies may be identified by glycan microarray analysis. Monoclonal antibodies may be screened on a printed glycan microarray version 5.0 from the Consortium for Functional Glycomics (CFG) as described previously (Blixt, O., et al. Proc Natl Acad Sci USA 101, 17033-17038 (2004)). Antibodies are used at a concentration of 30 µg/ml and were precomplexed with 15 µg/ml secondary antibody (goat-anti-human-Fc-rPE, Jackson Immunoresearch) before addition to the slide. Complete glycan array data sets for all antibodies may be found at www.functionalglycomics.org in the CFG data archive under "cfg_rRequest_2250".

Where used herein and unless specifically indicated otherwise, the following terms are intended to have the following meanings in addition to any broader (or narrower) meanings the terms might enjoy in the art:

The term "isolated" or "non-naturally occurring" is used herein to indicate that the isolated moiety (e.g. peptide or compound) exists in a physical milieu distinct from that in which it occurs in nature. For example, the isolated peptide may be substantially isolated with respect to the complex cellular milieu in which it naturally occurs. The absolute level of purity is not critical, and those skilled in the art can readily determine appropriate levels of purity according to the use to which the peptide is to be put. The term "isolating" when used a step in a process is to be interpreted accordingly.

In many circumstances, the isolated moiety will form part of a composition (for example a more or less crude extract containing many other molecules and substances), buffer system, matrix or excipient, which may for example contain other components (including proteins, such as albumin).

In other circumstances, the isolated moiety may be purified to essential homogeneity, for example as determined by PAGE or column chromatography (for example HPLC or mass spectrometry). In preferred embodiments, the isolated peptide or nucleic acid of the invention is essentially the sole peptide or nucleic acid in a given composition.

The proteins and compounds of the invention need not be isolated in the sense defined above, however.

The term "pharmaceutical composition" is used herein to define a solid or liquid composition in a form, concentration and level of purity suitable for administration to a patient (e.g. a human patient) upon which administration it can elicit the desired physiological changes. The terms "immunogenic composition" and "immunological composition" and "immunogenic or immunological composition" cover any composition that elicits an immune response against the targeted pathogen, HIV. Terms such as "vaccinal composition" and "vaccine" and "vaccine composition" cover any composition that induces a protective immune response against the targeted pathogen or which efficaciously protects against the pathogen; for instance, after administration or injection, elicits a protective immune response against the targeted pathogen or provides efficacious protection against the pathogen. Accordingly, an immunogenic or immunological composition induces an immune response, which can, but need not, be a protective immune response. An immunogenic or immunological composition can be used in the treatment of individuals infected with the pathogen, e.g., to stimulate an immune response against the pathogen, such as by stimulating antibodies against the pathogen. Thus, an immunogenic or immunological composition can be a pharmaceutical composition. Furthermore, when the text speaks of "immunogen, antigen or epitope", an immunogen can be an antigen or an epitope of an antigen. A diagnostic composition is a composition containing a compound or antibody, e.g., a labeled compound or antibody, that is used for detecting the presence in a sample, such as a biological sample, e.g., blood, semen, vaginal fluid, etc, of an antibody that binds to the compound or an immunogen, antigen or epitope that binds to the antibody; for instance, an anti-HIV antibody or an HIV immunogen, antigen or epitope.

A "binding site" can be a site (such as an atom, a functional group of an amino acid residue or a plurality of such atoms and/or groups) in a binding cavity or region, which may bind to a compound such as a candidate immunogen, antigen or epitope, protein, peptide, derivatized protein or peptide, or compound. An "active site" can be a site (such as an atom, a functional group of an amino acid residue or a plurality of such atoms and/or groups) in a binding cavity or region, which is/are involved in binding.

By "fitting", is meant determining by automatic, or semi-automatic means, interactions between one or more atoms of a candidate molecule and at least one atom of a structure of the invention, and calculating the extent to which such interactions are stable. Interactions include attraction and repulsion, brought about by charge, steric considerations and the like. Various computer-based methods for fitting are described further herein.

By a "computer system", we mean the hardware means, software means and data storage means used to analyse atomic coordinate data. The minimum hardware means of the computer-based systems of the present invention typically comprises a central processing unit (CPU), input means, output means and data storage means. Desirably a monitor is provided to visualize structure data. The data storage means may be RAM or means for accessing computer readable media of the invention. Examples of such systems are Linux and Mac OS X workstations.

By "computer readable media", we mean any medium or media, which can be read and accessed directly by a computer e.g. so that the media is suitable for use in the above-mentioned computer system. Such media include, but are not limited to: hard disc storage medium; optical storage media such as optical discs or CD-ROM and electrical storage media such as RAM and ROM.

A "conservative amino acid change" is one in which the amino acid residue is replaced with an amino acid residue having a similar side chain. Families of amino acid residues having similar side chains have been defined in the art. These families include amino acids with basic side chains (e.g. lysine, arginine and histidine), acidic side chains (e.g. aspartic acid and glutamic acid), non-charged amino acids or polar side chains (e.g. glycine, asparagine, glutamine, serine, threonine, tyrosine and cysteine), non-polar side chains (e.g. alanine, valine, leucine, isoleucine, proline, phenylalanine, methionine and tryptophan), beta-branched side chains (e.g. threonine, valine and isoleucine), and aromatic side chains (e.g. tyrosine, phenylalanine, tryptophan and histidine).

Thus, references herein to proteins and peptides that are to some defined extent "identical" (or which share a defined extent of "identity") with a reference protein or peptide may also optionally be interpreted to include proteins and peptides in which conservative amino acid changes are disregarded so that the original amino acid and its changed counterpart are regarded as identical for the purposes of sequence comparisons. Accordingly, the invention can comprehend proteins or peptides and the use thereof having conservative amino acid changes as to SEQ ID NO: 1, so long as the three dimensional structure, as defined herein, is maintained, e.g., so that there is binding/complexing with a PGT or PG antibody, advantageously PGT 127 or PGT 128.

The terms "protein", "peptide", "polypeptide", and "amino acid sequence" are used interchangeably herein to refer to polymers of amino acid residues of any length. The polymer may be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

As used herein, the terms "antigen" or "immunogen" are used interchangeably to refer to a substance, typically a protein, which is capable of inducing an immune response in a subject. The term also refers to proteins that are immunologically active in the sense that once administered to a subject (either directly or by administering to the subject a nucleotide sequence or vector that encodes the protein) is able to evoke an immune response of the humoral and/or cellular type directed against that protein.

The term "antibody" includes intact molecules as well as fragments thereof, such as Fab, $F(ab')_2$, Fv and scFv which are capable of binding the epitope determinant. These antibody fragments retain some ability to selectively bind with its antigen or receptor and include, for example:

a. Fab, the fragment which contains a monovalent antigen-binding fragment of an antibody molecule can be produced by digestion of whole antibody with the enzyme papain to yield an intact light chain and a portion of one heavy chain;
b. Fab', the fragment of an antibody molecule can be obtained by treating whole antibody with pepsin, followed by reduction, to yield an intact light chain and a portion of the heavy chain; two Fab' fragments are obtained per antibody molecule;
c. $F(ab')_2$, the fragment of the antibody that can be obtained by treating whole antibody with the enzyme pepsin without subsequent reduction; $F(ab')_2$ is a dimer of two Fab' fragments held together by two disulfide bonds;
d. scFv, including a genetically engineered fragment containing the variable region of a heavy and a light chain as a fused single chain molecule.

General methods of making these fragments are known in the art. (See for example, Harlow and Lane, Antibodies: A Laboratory Manual, Cold Spring Harbor Laboratory, New York (1988), which is incorporated herein by reference). Fabs, Fv and scFV may also be made recombinantly, i.e. expressed as Fab, Fv or scFV rather than cleaving an intact IgG.

A "neutralizing antibody" may inhibit the entry of HIV-1 virus for example SF162 and/or JR-CSF with a neutralization index >1.5 or >2.0. Broad and potent neutralizing antibodies may neutralize greater than about 50% of HIV-1 viruses (from diverse clades and different strains within a clade) in a neutralization assay. The inhibitory concentration of the monoclonal antibody may be less than about 25 mg/ml to neutralize about 50% of the input virus in the neutralization assay.

An "isolated antibody" or "non-naturally occurring antibody" is one that has been separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In preferred embodiments, the antibody is purified: (1) to greater than 95% by weight of antibody as determined by the Lowry method, and most preferably more than 99% by weight; (2) to a degree sufficient to obtain at least 15 residues of N-terminal or internal amino acid sequence by use of a spinning cup sequenator; or (3) to homogeneity by SDS-PAGE under reducing or non-reducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222: 581-597 (1991), for example.

An "antibody fragment" comprises a portion of an intact antibody, preferably the antigen binding or variable region of the intact antibody. Examples of antibody fragments include Fab, Fab', F(ab')$_2$, scFV and Fv fragments; diabodies; linear antibodies (see U.S. Pat. No. 5,641,870; Zapata et al., Protein Eng. 8(10): 1057-1062 [1995]); single-chain antibody molecules; and multispecific antibodies formed from antibody fragments.

It should be understood that the proteins, including the antibodies of the invention may differ from the exact sequences illustrated and described herein. Thus, the invention contemplates deletions, additions and substitutions to the sequences shown, so long as the sequences function in accordance with the methods of the invention. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. It is reasonably predictable that an isolated or non-naturally occurring replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the biological activity. Proteins having substantially the same amino acid sequence as the sequences illustrated and described but possessing minor amino acid substitutions that do not substantially affect the immunogenicity of the protein are, therefore, within the scope of the invention.

As used herein the terms "nucleotide sequences" and "nucleic acid sequences" refer to deoxyribonucleic acid (DNA) or ribonucleic acid (RNA) sequences, including, without limitation, messenger RNA (mRNA), DNA/RNA hybrids, or synthetic nucleic acids. The nucleic acid can be single-stranded, or partially or completely double-stranded (duplex). Duplex nucleic acids can be homoduplex or heteroduplex.

As used herein the term "transgene" may used to refer to "recombinant" nucleotide sequences that may be derived from any of the nucleotide sequences encoding the proteins of the present invention. The term "recombinant" means a nucleotide sequence that has been manipulated "by man" and which does not occur in nature, or is linked to another nucleotide sequence or found in a different arrangement in nature. It is understood that manipulated "by man" means manipulated by some artificial means, including by use of machines, codon optimization, restriction enzymes, etc.

For example, in one embodiment the nucleotide sequences may be mutated such that the activity of the encoded proteins in vivo is abrogated. In another embodiment the nucleotide sequences may be codon optimized, for example the codons may be optimized for human use. In preferred embodiments the nucleotide sequences of the invention are both mutated to abrogate the normal in vivo function of the encoded proteins, and codon optimized for human use. For example, each of the sequences of the invention, such as SEQ ID NO: 1, may be altered in these ways.

As regards codon optimization, the nucleic acid molecules of the invention have a nucleotide sequence that encodes the antigens of the invention and can be designed to employ codons that are used in the genes of the subject in which the antigen is to be produced. Many viruses, including HIV and other lentiviruses, use a large number of rare codons and, by altering these codons to correspond to codons commonly used in the desired subject, enhanced expression of the antigens can be achieved. In a preferred embodiment, the codons used are "humanized" codons, i.e., the codons are those that appear frequently in highly expressed human genes (Andre et al., J. Virol. 72:1497-1503, 1998) instead of those codons that are frequently used by HIV. Such codon usage provides for efficient expression of the transgenic HIV proteins in human cells. Any suitable method of codon optimization may be used. Such methods, and the selection of such methods, are well known to those of skill in the art. In addition, there are several companies that will optimize codons of sequences, such as Geneart (geneart.com). Thus, the nucleotide sequences of the invention can readily be codon optimized.

The invention further encompasses nucleotide sequences encoding functionally and/or antigenically equivalent variants and derivatives of the antigens of the invention and functionally equivalent fragments thereof. These functionally equivalent variants, derivatives, and fragments display the ability to retain antigenic activity. For instance, changes in a DNA sequence that do not change the encoded amino acid sequence, as well as those that result in conservative substitutions of amino acid residues, one or a few amino acid deletions or additions, and substitution of amino acid residues by amino acid analogs are those which will not significantly affect properties of the encoded polypeptide. Conservative amino acid substitutions are glycine/alanine; valine/isoleucine/leucine; asparagine/glutamine; aspartic acid/glutamic acid; serine/threonine/methionine; lysine/arginine; and phenylalanine/tyrosine/tryptophan. In one embodiment, the variants have at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% homology or identity to the antigen, epitope, immunogen, peptide or polypeptide of interest.

For the purposes of the present invention, sequence identity or homology is determined by comparing the sequences when aligned so as to maximize overlap and identity while minimizing sequence gaps. In particular, sequence identity may be determined using any of a number of mathematical algorithms. A nonlimiting example of a mathematical algorithm used for comparison of two sequences is the algorithm of Karlin & Altschul, Proc. Natl. Acad. Sci. USA 1990; 87: 2264-2268, modified as in Karlin & Altschul, Proc. Natl. Acad. Sci. USA 1993; 90: 5873-5877.

Another example of a mathematical algorithm used for comparison of sequences is the algorithm of Myers & Miller, CABIOS 1988; 4: 11-17. Such an algorithm is incorporated into the ALIGN program (version 2.0) which is part of the GCG sequence alignment software package. When utilizing the ALIGN program for comparing amino acid sequences, a PAM 120 weight residue table, a gap length penalty of 12, and a gap penalty of 4 can be used. Yet another useful algorithm for identifying regions of local sequence similarity and alignment is the FASTA algorithm as described in Pearson & Lipman, Proc. Natl. Acad. Sci. USA 1988; 85: 2444-2448.

Advantageous for use according to the present invention is the WU-BLAST (Washington University BLAST) version 2.0 software. WU-BLAST version 2.0 executable programs for several UNIX platforms can be downloaded from ftp://blast.wustl.edu/blast/executables. This program is based on WU-BLAST version 1.4, which in turn is based on the public domain NCBI-BLAST version 1.4 (Altschul & Gish, 1996, Local alignment statistics, Doolittle ed., Methods in Enzymology 266: 460-480; Altschul et al., Journal of Molecular Biology 1990; 215: 403-410; Gish & States, 1993; Nature Genetics 3: 266-272; Karlin & Altschul, 1993; Proc. Natl. Acad. Sci. USA 90: 5873-5877; all of which are incorporated by reference herein).

The various recombinant nucleotide sequences and antibodies of the invention are made using standard recombinant DNA and cloning techniques. Such techniques are well known to those of skill in the art. See for example, "Molecular Cloning: A Laboratory Manual", second edition (Sambrook et al. 1989).

The nucleotide sequences of the present invention may be inserted into "vectors." The term "vector" is widely used and understood by those of skill in the art, and as used herein the term "vector" is used consistent with its meaning to those of skill in the art. For example, the term "vector" is commonly used by those skilled in the art to refer to a vehicle that allows or facilitates the transfer of nucleic acid molecules from one environment to another or that allows or facilitates the manipulation of a nucleic acid molecule.

Any vector that allows expression of the antibodies of the present invention may be used in accordance with the present invention. In certain embodiments, the antibodies of the present invention may be used in vitro (such as using cell-free expression systems) and/or in cultured cells grown in vitro in order to produce the encoded HIV-antibodies, which may then be used for various applications such as in the production of proteinaceous vaccines. For such applications, any vector that allows expression of the antibodies in vitro and/or in cultured cells may be used.

For applications where it is desired that the antibodies be expressed in vivo, for example when the transgenes of the invention are used in DNA or DNA-containing vaccines, any vector that allows for the expression of the antibodies of the present invention and is safe for use in vivo may be used. In preferred embodiments the vectors used are safe for use in humans, mammals and/or laboratory animals.

For the antibodies of the present invention to be expressed, the protein coding sequence should be "operably linked" to regulatory or nucleic acid control sequences that direct transcription and translation of the protein. As used herein, a coding sequence and a nucleic acid control sequence or promoter are said to be "operably linked" when they are covalently linked in such a way as to place the expression or transcription and/or translation of the coding sequence under the influence or control of the nucleic acid control sequence. The "nucleic acid control sequence" can be any nucleic acid element, such as, but not limited to promoters, enhancers, IRES, introns, and other elements described herein that direct the expression of a nucleic acid sequence or coding sequence that is operably linked thereto. The term "promoter" will be used herein to refer to a group of transcriptional control modules that are clustered around the initiation site for RNA polymerase II and that when operationally linked to the protein coding sequences of the invention lead to the expression of the encoded protein. The expression of the transgenes of the present invention can be under the control of a constitutive promoter or of an inducible promoter, which initiates transcription only when exposed to some particular external stimulus, such as, without limitation, antibiotics such as tetracycline, hormones such as ecdysone, or heavy metals. The promoter can also be specific to a particular cell-type, tissue or organ. Many suitable promoters and enhancers are known in the art, and any such suitable promoter or enhancer may be used for expression of the transgenes of the invention. For example, suitable promoters and/or enhancers can be selected from the Eukaryotic Promoter Database (EPDB).

The vectors used in accordance with the present invention should typically be chosen such that they contain a suitable gene regulatory region, such as a promoter or enhancer, such that the antibodies of the invention can be expressed.

For example, when the aim is to express the antibodies of the invention in vitro, or in cultured cells, or in any prokaryotic or eukaryotic system for the purpose of producing the protein(s) encoded by that antibody, then any suitable vector can be used depending on the application. For example, plasmids, viral vectors, bacterial vectors, protozoal vectors, insect vectors, baculovirus expression vectors, yeast vectors, mammalian cell vectors, and the like, can be used. Suitable vectors can be selected by the skilled artisan taking into consideration the characteristics of the vector and the requirements for expressing the antibodies under the identified circumstances.

In an advantageous embodiment, IgG1 and Fab expression vectors may be utilized to reconstitute heavy and light chain constant regions if heavy and light chain genes of the antibodies of the present invention are cloned.

When the aim is to express the antibodies of the invention in vivo in a subject, for example in order to generate an immune response against an HIV-1 antigen and/or protective immunity against HIV-1, expression vectors that are suitable for expression on that subject, and that are safe for use in vivo, should be chosen. For example, in some embodiments it may be desired to express the antibodies of the invention in a laboratory animal, such as for pre-clinical testing of the HIV-1 immunogenic compositions and vaccines of the invention. In other embodiments, it will be desirable to express the antibodies of the invention in human subjects, such as in clinical trials and for actual clinical use of the immunogenic compositions and vaccine of the invention. Any vectors that are suitable for such uses can be employed, and it is well within the capabilities of the skilled artisan to select a suitable vector. In some embodiments it may be preferred that the vectors used for these in vivo applications are attenuated to vector from amplifying in the subject. For example, if plasmid vectors are used, preferably they will lack an origin of replication that functions in the subject so as to enhance safety for in vivo use in the subject. If viral vectors are used, preferably they are attenuated or replication-defective in the subject, again, so as to enhance safety for in vivo use in the subject.

In preferred embodiments of the present invention viral vectors are used. Viral expression vectors are well known to those skilled in the art and include, for example, viruses such as adenoviruses, adeno-associated viruses (AAV), alphaviruses, herpesviruses, retroviruses and poxviruses, including avipox viruses, attenuated poxviruses, vaccinia viruses, and particularly, the modified vaccinia Ankara virus (MVA; ATCC Accession No. VR-1566). Such viruses, when used as expression vectors are innately non-pathogenic in the selected subjects such as humans or have been modified to render them non-pathogenic in the selected subjects. For example, replication-defective adenoviruses and alphaviruses are well known and can be used as gene delivery vectors.

The nucleotide sequences and vectors of the invention can be delivered to cells, for example if the aim is to express the HIV-1 antigens in cells in order to produce and isolate the expressed proteins, such as from cells grown in culture. For expressing the antibodies in cells any suitable transfection, transformation, or gene delivery methods can be used. Such methods are well known by those skilled in the art, and one of skill in the art would readily be able to select a suitable method depending on the nature of the nucleotide sequences, vectors, and cell types used. For example, transfection, transformation, microinjection, infection, electroporation, lipofection, or liposome-mediated delivery could be used. Expression of the antibodies can be carried out in any suitable type of host cells, such as bacterial cells, yeast, insect cells, and mammalian cells. The antibodies of the invention can also be expressed using including in vitro transcription/translation systems. All of such methods are well known by those skilled in the art, and one of skill in the art would readily be able to select a suitable method depending on the nature of the nucleotide sequences, vectors, and cell types used.

The synthetic SEQ ID NO: 1 described herein may be chemically synthesized in whole or part using techniques that are well-known in the art (see, e.g., Kochendoerfer, G. G., 2001). Additionally, homologs and derivatives of the polypeptide may be also be synthesized.

Alternatively, methods which are well known to those skilled in the art can be used to construct expression vectors containing nucleic acid molecules that encode the polypeptide or homologs or derivatives thereof under appropriate transcriptional/translational control signals, for expression. These methods include in vitro recombinant DNA techniques, synthetic techniques and in vivo recombination/ genetic recombination. See, for example, the techniques described in Maniatis et al., 1989.

The crystals of the invention can be obtained by conventional means as are well-known in the art of protein crystallography, including batch, liquid bridge, dialysis, vapor diffusion and hanging drop methods (see, e.g., McPherson, 1982; McPherson, 1990; Webber, 1991). Generally, the crystals of the invention are grown by combining substantially pure PGT 127 or PGT 128 and compound (e.g., SEQ ID NO: 1 or polypeptide eODmV3 in example, but other compounds may be used to test if such compounds form crystals analogous to those disclosed herein) in an aqueous buffer containing a precipitant at a concentration just below that necessary to precipitate the protein. Water is removed by controlled evaporation to produce precipitating conditions, which are maintained until crystal growth ceases.

The crystals of the invention, and particularly the atomic structure co-ordinates obtained therefrom, have a wide variety of uses. The crystals and structure co-ordinates are particularly useful for identifying compounds that bind to PGT 127 or PGT 128 and thus are useful to elicit anti-HIV antibodies.

The structure co-ordinates described herein can be used as phasing models in determining the crystal structures of additional synthetic or mutated PGT 127 or PGT 128 domains, as well as the structures of co-crystals of such domains with ligands.

The provision of the crystal structure of PGT 127 or PGT 128 complexed with eODmV3 or Man$_9$ glycan in Table S1 and the Figures provide the skilled artisan with a detailed insight into the mechanisms of action of PGT 127 or PGT 128. This insight provides a means to design compounds that bind to PGT 127 or PGT 128 and thus to certain anti-HIV antibodies, and therefore compounds that elicit anti-HIV antibodies, which are useful in diagnosis, treatment, or prevention of HIV in an individual in need thereof.

The provision of the crystal structure of PGT 127 or PGT 128 complexed with eODmV3 or Man$_9$ or Man-rich glycans or and modified non-natural glycan that mimic Man glycans allows a novel approach for drug or compound discovery, identification, and design for compounds that bind to PGT 127 or PGT 128 and thus to anti-HIV antibodies, and therefore compounds that elicit anti-HIV antibodies, which are useful in diagnosis, treatment, or prevention of HIV in an individual in need thereof. Accordingly, the invention provides a computer-based method of rational drug or compound design or identification which comprises: providing the structure of the PGT 127 or PGT 128 complex as defined by the co-ordinates or the identifying co-ordinates in Table S1 and/or in the Figures; providing a structure of a candidate compound; and fitting the structure of the candidate to the structure of PGT 127 or PGT 128 of Table S1 and the Figures.

In an alternative aspect, the method may use the co-ordinates of atoms of interest of PGT 127 or PGT 128, which are in the vicinity of the active site or binding region in order to model the pocket in which the substrate or ligand binds. These co-ordinates may be used to define a space which is then screened "in silico" against a candidate molecule. Thus, the invention provides a computer-based method of rational drug or compound design or identification which comprises: providing the co-ordinates of at least two atoms of Table S1 ("selected co-ordinates"); providing the structure of a candidate compound; and fitting the structure of the candidate to the selected coordinates.

In practice, it may be desirable to model a sufficient number of atoms of PGT 127 or PGT 128 as defined by the co-ordinates of Table S1, which represent the active site or binding region. Thus, there can be provided the co-ordinates of at least 5, advantageously at least 10, more advantageously at least 50 and even more advantageously at least 100 atoms of the structure. Accordingly, the methods of the invention can employ a sub-domain of interest of PGT 127 or PGT 128 which is in the vicinity of the active site or binding region, and the invention can provide a computer-based method for identifying or rationally designing a compound or drug which comprises: providing the coordinates of at least a sub-domain of; providing the structure of a candidate modulator or inhibitor of PGT 127 or PGT 128; and fitting the structure of the candidate to the coordinates of the PGT 127 or PGT 128 sub-domain provided.

These methods can optionally include synthesizing the candidate and can optionally further include contacting the candidate with PGT 127 or PGT 128 to test whether there is binding and/or inhibition and/or administering the compound to an animal capable of eliciting antibodies and testing whether the compound elicits anti-HIV antibodies. Compounds which elicit anti-HIV antibodies are useful for diagnostic purposes, as well as for immunogenic, immunological or even vaccine compositions, as well as pharmaceutical compositions.

The present invention may also be extrapolated to crystallizing other complexes of broadly neutralizing antibodies and compositions that bind to such broadly neutralizing antibodies including, for example, compositions that contain SEQ ID NO: 1. One of skill in the art may utilize the teachings of the present invention to crystallize such a complex, identify a binding region and design a compound that fit the coordinates of the binding region and testing the compound to determine if the compound elicits anti-HIV antibodies.

"Fitting" can mean determining, by automatic or semi-automatic means, interactions between at least one atom of the candidate and at least one atom of a neutralizing antibody, such as PGT 127 or PGT 128, and calculating the extent to which such an interaction is stable. Interactions can include attraction, repulsion, brought about by charge, steric considerations, and the like. A "sub-domain" can mean at least one, e.g., one, two, three, or four, complete element(s) of secondary structure. Particular regions of a neutralizing antibody, such as PGT 127 or PGT 128, include those identified in Table 51.

The step of providing the structure of a candidate molecule may involve selecting the compound by computationally screening a database of compounds for interaction with the active site. For example, a 3-D descriptor for the potential modulator may be derived, the descriptor including geometric and functional constraints derived from the architecture and chemical nature of the active site. The descriptor may then be used to interrogate the compound database, a potential modulator being a compound that has a good match to the features of the descriptor. In effect, the descriptor can be a type of virtual pharmacophore.

In any event, the determination of the three-dimensional structure of a neutralizing antibody, such as PGT 127 or PGT 128, complex provides a basis for the design of new and specific compounds that bind to a neutralizing antibody, such as PGT 127 or PGT 128, and are useful for eliciting an immune response. For example, from knowing the three-dimensional structure of a neutralizing antibody, such as PGT 127 or PGT 128, complex, computer modelling programs may be used to design or identify different molecules expected to interact with possible or confirmed active sites such as binding sites or other structural or functional features of A neutralizing antibody, such as PGT 127 or PGT 128. More specifically, a compound that potentially binds ("binder") to a neutralizing antibody, such as PGT 127 or PGT 128, activity can be examined through the use of computer modeling using a docking program such as GRAM, DOCK or AUTODOCK (see Walters et al. Drug Discovery Today, vol. 3, no. 4 (1998), 160-178, and Dunbrack et al. Folding and Design 2 (1997), 27-42). This procedure can include computer fitting of potential binders to a neutralizing antibody, such as PGT 127 or PGT 128, to ascertain how well the shape and the chemical structure of the potential binder will bind to the antibody.

Also, computer-assisted, manual examination of the active site or binding site of A neutralizing antibody, such as PGT 127 or PGT 128, may be performed. The use of programs such as GRID (P. Goodford, J. Med. Chem., 1985, 28, 849-57)—program that determines probable interaction sites between molecules with various functional groups and the antibody—may also be used to analyze the active site or binding site to predict partial structures of binding compounds.

Computer programs can be employed to estimate the attraction, repulsion or steric hindrance of the two binding partners, e.g., a neutralizing antibody, such as PGT 127 or PGT 128, and a candidate binder. Generally, the tighter the fit, the fewer the steric hindrances, and the greater the attractive forces, the more potent the potential binder, since these properties are consistent with a tighter binding constant. Furthermore, the more specificity in the design of a candidate binder, the more likely it is that it will not interact with other proteins as well.

In a further aspect, the invention provides for a method for determining the structure of a binder of a neutralizing antibody, such as PGT 127 or PGT 128, bound to A neutralizing antibody, such as PGT 127 or PGT 128, said method comprising, (a) providing a crystal of a neutralizing antibody, such as PGT 127 or PGT 128, according to the invention, (b) soaking the crystal or another crystal with said binder; and (c) determining the structure of said neutralizing antibody, such as PGT 127 or PGT 128-binder complex. Such other crystal may have essentially the same coordinates discussed herein, however due to minor alterations in the polypeptide or sequence, the crystal may form in a different space group.

The invention further involves, in place of or in addition to in silico methods, high throughput screening of compounds to select compounds with binding activity. Those compounds which show binding activity may be selected as possible candidate binders, and further crystallized with a neutralizing antibody, such as PGT 127 or PGT 128, e.g., by co-crystallization or by soaking, for X-ray analysis. The resulting X-ray structure may be compared with that of Table 51 and the information in the Figures for a variety of purposes. For example, where the contacts made by such compounds overlap with those made by PGT 127 or PGT 128, novel molecules comprising residues which contain contacts of PGT 127 or PGT 128 and other compounds may be provided.

Having designed, identified, or selected possible binding candidate binders by determining those that have favorable fitting properties, e.g., strong attraction between a candidate and a neutralizing antibody, such as PGT 127 or PGT 128, these can then be screened for activity. Consequently, the invention further involves: obtaining or synthesizing the candidate modulator or inhibitor; and contacting the candidate binder with a neutralizing antibody, such as PGT 127 or PGT 128, to determine the ability of the candidate to bind with a neutralizing antibody, such as PGT 127 or PGT 128. In the latter step, the candidate is advantageously contacted with a neutralizing antibody, such as PGT 127 or PGT 128, under conditions to determine its function. Instead of, or in addition to, performing such an assay, the invention may comprise: obtaining or synthesizing the candidate modulator, forming a complex of a neutralizing antibody, such as PGT 127 or PGT 128, and the candidate, and analyzing the complex, e.g., by X-ray diffraction or NMR or EM or other means, to determine the ability of the candidate to interact with a neutralizing antibody, such as PGT 127 or PGT 128. Detailed structural information can then be obtained about the binding of the candidate to a neutralizing antibody, such as PGT 127 or PGT 128, and in light of this information, adjustments can be made to the structure or functionality of the potential modulator, e.g., to improve its binding to a neutralizing antibody, such as PGT 127 or PGT 128. These steps may be repeated and re-repeated as necessary. Alternatively or additionally, potential binders can be administered to an animal capable of eliciting an antibody response, to ascertain whether the potential binder elicits anti-HIV antibodies.

The invention further involves a method of determining three-dimensional structures of a neutralizing antibody, such as PGT 127 or PGT 128, and SEQ ID NO: 1, eODmV3 or $Man_9$ glycan homologues of unknown structure by using the structural co-ordinates of Table 51 and the information in the Figures. For example, if X-ray crystallographic or NMR spectroscopic data are provided for a PGT 127 or PGT 128 and/or SEQ ID NO: 1, eODmV3 or $Man_9$ glycan homologue of unknown structure, the structure of PGT 127 or PGT 128 complex as defined in Table 51 and the Figures may be used to interpret that data to provide a likely structure for the PGT 127 or PGT 128 and/or SEQ ID NO: 1, eODmV3 or $Man_9$ glycan homologue by techniques well known in the art, e.g., by phase modeling in the case of X-ray crystallography. Thus, an inventive method can comprise: aligning a representation of an amino acid sequence of a PGT 127 or PGT 128 and/or SEQ ID NO: 1, eODmV3 or $Man_9$ or Man-rich glycan homologue or modified non-natural glycan that mimic Man glycans of unknown structure with the amino acid sequence of PGT 127 or PGT 128 and/or SEQ ID NO: 1, eODmV3 or $Man_9$ or Man-rich glycan to match homologous regions of the amino acid sequences; modeling the structure of the matched homologous regions of the PGT 127 or PGT 128 and/or SEQ ID NO: 1, eODmV3 or $Man_9$ or Man-rich glycan or modified non-natural glycan that mimic Man glycans of unknown structure on the structure as defined in Table 51 and/or in the Figures of the corresponding regions of PGT 127 or PGT 128 and/or SEQ ID NO: 1, eODmV3 or $Man_9$ or Man-rich glycan or modified non-natural glycan that mimic Man glycans and, determining a conformation (e.g. so that favorable interactions are formed within the PGT 127 or PGT 128 and/or SEQ ID NO: 1, eODmV3 or $Man_9$ or Man-rich glycan of unknown structure pr modified non-natural glycan that mimic Man glycans so that a low energy conformation is formed) for the PGT 127 or PGT 128 and/or SEQ ID NO: 1, eODmV3 or $Man_9$ glycan of unknown structure which substantially preserves the structure of said matched homologous regions. "Homologous regions" describes amino acid residues in two sequences that are identical or have similar, e.g., aliphatic, aromatic, polar, negatively charged, or positively charged, side-chain chemical groups. Identical and similar residues in homologous regions are sometimes described as being respectively "invariant" and "conserved" by those skilled in the art. Advantageously, the first and third steps are performed by computer modeling. Homology modeling is a technique that is well known to those skilled in the art (see, e.g., Greer, 1985; and Blundell et al. 1988).

In general, comparison of amino acid sequences is accomplished by aligning an amino acid sequence of a polypeptide of a known structure with the amino acid sequence of the polypeptide of unknown structure. Amino acids in the sequences are then compared and groups of amino acids that are homologous are grouped together. This method detects conserved regions of the polypeptides and accounts for amino acid insertions and deletions. Homology between amino acid sequences can be determined by using commercially available algorithms (see also the description of homology above). In addition to those otherwise mentioned herein, mention is made too of the programs BLAST, gapped BLAST, BLASTN, BLASTP, and PSI-BLAST, provided by the National Center for Biotechnology Information. These programs are widely used in the art for this purpose and can align homologous regions of two amino acid sequences.

Once the amino acid sequence of the polypeptides with known and unknown structures are aligned, the structures of the conserved amino acids in a computer representation of the polypeptide with known structure are transferred to the corresponding amino acids of the polypeptide whose structure is unknown. For example, a tyrosine in the amino acid sequence of known structure may be replaced by a phenylalanine, the corresponding homologous amino acid in the amino acid sequence of unknown structure. The structures of amino acids located in non-conserved regions may be assigned manually using standard peptide geometries or by molecular simulation techniques, such as molecular dynamics. Refining the entire structure can be by molecular dynamics and/or energy minimization.

The aspects of the invention which employ the PGT 127 or PGT 128 and/or eODmV3 or $Man_9$ or Man-rich glycan or modified non-natural glycan that mimic Man glycans structure in silico may be equally applied to homologue models of PGT 127 or PGT 128 and/or SEQ ID NO: 1, eODmV3 or $Man_9$ glycan obtained by the above aspect of the invention and this forms yet a further embodiment of the invention. Thus, having determined a conformation of a PGT 127 or PGT 128 and/or SEQ ID NO: 1, eODmV3 or $Man_9$ or Man-rich glycan or modified non-natural glycan that mimic Man glycans by the methods described herein, such a conformation may be used in a computer-based method of rational drug or compound design or identification as described herein.

The invention further provides a method for determining the structure of a binder of a neutralizing antibody, such as PGT 127 or PGT 128, bound to a neutralizing antibody, such as PGT 127 or PGT 128, comprising: providing a crystal a neutralizing antibody, such as PGT 127 or PGT 128, e.g., according to the invention, soaking the crystal with the binder, and determining the structure of the a neutralizing antibody, such as PGT 127 or PGT 128-binder complex. Alternatively or additionally, a neutralizing antibody, such as PGT 127 or PGT 128, and the binder may be cocrystallized.

The invention further provides systems, such as computer systems, intended to generate structures and/or perform rational drug or compound design for a neutralizing antibody, such as PGT 127 or PGT 128, or complex of a neutralizing antibody, such as PGT 127 or PGT 128, and a potential binder. The system can contain: atomic co-ordinate data according to Table 51 and the Figures or derived therefrom by homology modeling, said data defining the three-dimensional structure of a PGT 127 or PGT 128 or at least one sub-domain thereof; or structure factor data for PGT 127 or PGT 128, said structure factor data being derivable from the atomic co-ordinate data of Table 51 and the Figures. The invention also involves computer readable media with: atomic coordinate data according to Table 51 and/or the Figures or derived therefrom by homology modeling, said data defining the three-dimensional structure of a PGT 127 or PGT 128 or at least one sub-domain thereof; or structure factor data for PGT 127 or PGT 128, said structure factor data being derivable from the atomic co-ordinate data of Table 51 and/or the Figures.

"Computer readable media" refers to any media which can be read and accessed directly by a computer, and includes, but is not limited to: magnetic storage media such as floppy discs, hard storage medium and magnetic tape; optical storage media such as optical discs or CD-ROM; electrical storage media such as RAM and ROM; and hybrids of these categories, such as magnetic/optical media. By providing such computer readable media, the atomic co-ordinate data can be routinely accessed to model PGT 127 or PGT 128 or a sub-domain thereof. For example RASMOL (Sayle et al., TIBS vol. 20 (1995), 374) is a publicly available software package, which allows access and analysis of atomic coordinate data for structural determination and/or rational drug design. The invention further comprehends methods of doing business by providing access to such computer readable media and/or computer systems and/or atomic co-ordinate data to users; e.g., the media and/or atomic co-ordinate data can be accessible to a user, for instance on a subscription basis, via the Internet or a global communication/computer network; or, the computer system can be available to a user, on a subscription basis. Structure factor data, which are derivable from atomic co-ordinate data (see, e.g., Blundell et al., in Protein Crystallography, Academic Press, NY, London and San Francisco (1976)), are particularly useful for calculating electron density maps, e.g., difference Fourier electron density maps. Thus, there are additional uses for the computer readable media and/or computer systems and/or atomic co-ordinate data and additional reasons to provide them to users. A "computer system" refers to the hardware means, software means and data storage means used to analyze the atomic co-ordinate data of the present invention. The minimum hardware means of computer-based systems of the invention may comprise a central processing unit (CPU), input means, output means, and data storage means. Desirably, a monitor is provided to visualize structure data. The data storage means may be RAM or other means for accessing computer readable media of the invention.

Accordingly, the invention further comprehends methods of transmitting information obtained in any method or step thereof described herein or any information described herein, e.g., via telecommunications, telephone, mass communications, mass media, presentations, internet, email, etc.

The invention also provides a method of analyzing a complex of PGT 127 or PGT 128 and a potential binder comprising: employing X-ray crystallographic diffraction data from the complex and a three-dimensional structure of PGT 127 or PGT 128 or at least a sub-domain thereof, to generate a Fourier electron density map of the complex; advantageously, the three-dimensional structure being as defined by the atomic co-ordinate data according to Table 51 and/or the Figures.

Such complexes can be crystallized and analyzed using X-ray diffraction methods, e.g., according to the approaches described by Greer et al., 1994, and Fourier electron density maps can be calculated based on X-ray diffraction patterns of soaked or co-crystallized a neutralizing antibody, such as PGT 127 or PGT 128, and the solved structure of uncomplexed a neutralizing antibody, such as PGT 127 or PGT 128. These maps can then be used to determine whether and where a particular potential binder binds to PGT 127 or PGT 128 and/or changes the conformation of a neutralizing antibody, such as PGT 127 or PGT 128. Electron density maps can be calculated using programs such as those from the CCP4 computer package (Collaborative Computing Project, No. 4. The CCP4 Suite: Programs for Protein Crystallography, Acta Crystallographica, D50, 1994, 760-763). For map visualization and model building programs such as "QUANTA" (1994, San Diego, Calif.: Molecular Simulations, Jones et al., 1991) can be used.

Table S1 gives atomic co-ordinate data for PGT 127 or PGT 128 complexed with SEQ ID NO: 1, eODmV3 or Man$_9$ glycan, and lists each atom by a unique number; the chemical element and its position for each amino acid residue (as determined by electron density maps and antibody sequence comparisons), the amino acid residue in which the element is located, the chain identifier, the number of the residue, coordinates (e.g., X, Y, Z) which define with respect to the crystallographic axes the atomic position (in .ANG.) of the respective atom, the occupancy of the atom in the respective position, "B", isotropic displacement parameter (in .ANG..sup.2), which accounts for movement of the atom around its atomic center, and atomic number. See also the text herein and the Figures.

Determination of the 3D structure of a neutralizing antibody, such as PGT 127 or PGT 128, provides important information about the likely active/binding site(s) of a neutralizing antibody, such as PGT 127 or PGT 128. This information may be used for rational design of a neutralizing antibody, such as PGT 127 or PGT 128, binders, e.g., by computational techniques that identify possible binding ligands for the active site(s), by enabling linked-fragment approaches to drug design, and by enabling the identification and location of bound ligands using analyses such as X-ray crystallographic analysis.

Greer et al., supra, relates to an iterative approach to ligand design based on repeated sequences of computer modeling, protein-ligand complex formation, and X-ray analysis. Thymidylate synthase inhibitors were designed by Greer; and, PGT 127 or PGT 128 binders may also be designed in this way. Using, for example, GRID (P. Goodford, 1985) or the solved 3D structure of a neutralizing antibody, such as PGT 127 or PGT 128, a potential binder of a neutralizing antibody, such as PGT 127 or PGT 128, may be designed that complements the functionalities of the a neutralizing antibody, such as PGT 127 or PGT 128, active site(s). The potential binder can be synthesized, formed into a complex with a neutralizing antibody, such as PGT 127 or PGT 128, and the complex then analyzed, e.g., by X-ray crystallography, NMR or a combination thereof, to identify the actual position of the bound compound.

Determination of the position of the potential binder compound in the complex allows determination of the interactions of it with a neutralizing antibody, such as PGT 127 or PGT 128. This allows the skilled artisan to analyze the affinity and specificity of the compound for a neutralizing antibody, such as PGT 127 or PGT 128, and to propose modifications to the compound to increase or decrease either or both of these properties. Thus, the structure and/or functional groups of the compound can then be adjusted, if necessary or desired, in view of the results from the analysis (e.g., X-ray analysis), and the synthesis and analysis sequence repeated until an optimized compound is obtained. Related approaches to structure-based drug and compound design are also discussed in other documents cited herein, as well as in Bohacek et al., 1996.

As a result of the determination of a neutralizing antibody, such as PGT 127 or PGT 128, 3D structure, more purely computational techniques for rational drug and compound design may also be used to design neutralizing antibody, such as PGT 127 or PGT 128, binders and hence compounds that elicit anti-HIV antibodies; for example, automated ligand-receptor docking programs (see Jones et al., 1995) which require accurate information on the atomic coordinates of target receptors, may be used to design or identify potential PGT 127 or PGT 128 binders.

Linked-fragment approaches to drug or compound design also require accurate information on the atomic co-ordinates of a target. Small compounds that have the potential to bind to regions of a neutralizing antibody, such as PGT 127 or PGT 128, which in themselves may not be binder compounds may be assembled by chemical linkage to provide potential binders. Thus, the basic idea behind these approaches is to determine the binding locations of more than one, e.g., plural or a plurality of, ligands to a target molecule, and then construct a molecular scaffold to connect the ligands together in such a way that their relative binding positions are preserved. The ligands may be provided computationally and modeled in a computer system, or provided in an experimental setting, wherein crystals according to the invention are provided and more than one, e.g., plural or a plurality of, ligands soaked separately or in mixed pools into the crystal prior to analysis, e.g., X-ray analysis, and determination of their location.

The binding site of two or more ligands are determined and may be connected to thus form a potential lead compound that can be further refined, e.g., the iterative technique of Greer et al. For a virtual linked-fragment approach, see Verlinde et al., 1992; and for NMR and X-ray approaches, see Skuker et al., 1996; and Stout et al., 1998. The use of these or other approaches to design and/or identify neutralizing antibody, such as PGT 127 or PGT 128, binders and hence compounds that elicit anti-HIV antibodies is made possible by the determination of the PGT 127 or PGT 128 structure.

Many of the techniques and approaches to structure-based described herein employ X-ray analysis to identify the binding position of a potential modulator in a complex with a protein. A common way of doing this is to perform X-ray crystallography on the complex, produce a Fourier electron density map, and associate a particular pattern of electron density with the potential modulator. However, to produce a map (See Blundell et al., supra), it is important to know the 3D structure of the protein beforehand (or at least the protein structure factors). Therefore, determination of a neutralizing antibody, such as PGT 127 or PGT 128, structure also allows difference Fourier electron density maps of complexes of neutralizing antibody, such as PGT 127 or PGT 128, with a potential modulator to be produced, which can greatly assist in the process of rational compound and/or drug design or identification.

The approaches to structure-based drug or compound design or identification described herein involve initial identification of possible compounds for interaction with the target molecule (in this case PGT 127 or PGT 128), and thus elicit anti-HIV antibodies. Sometimes these compounds are known, e.g., from research literature. However, when they are not, or when novel compounds are wanted, a first stage of the drug or compound design or identification program may involve computer-based in silico screening of compound databases (such as the Cambridge Structural Database) with the aim of identifying compounds which interact with the active site or sites of the target bio-molecule (in this case PGT 127 or PGT 128). Screening selection criteria may be based on pharmacokinetic properties such as metabolic stability and toxicity. However, determination of a neutralizing antibody, such as PGT 127 or PGT 128, structure allows the architecture and chemical nature of each neutralizing antibody, such as PGT 127 or PGT 128, active site to be identified, which in turn allows the geometric and functional constraints of a descriptor for the potential binder to be derived. The descriptor can be, therefore, a type of virtual 3D pharmacophore, which can also be used as selection criteria or filter for database screening.

Compounds which have a chemical structure selected using the invention, wherein said compounds are neutralizing antibody, such as PGT 127 or PGT 128, binders, form a further aspect of the invention; and, such compounds may be used in methods of medical treatments, such as for diagnosis, preventing or treating HIV or for eliciting antibodies for diagnosis of HIV, including use in vaccines. Further, such compounds may be used in the preparation of medicaments for such treatments or prevention, or compositions for diagnostic purposes. The compounds may be employed alone or in combination with other treatments, vaccines or preventatives; and, the compounds may be used in the preparation of combination medicaments for such treatments or prevention, or in kits containing the compound and the other treatment or preventative.

It is noted that these therapeutics can be a chemical compound, a composition comprising a polypeptide of the present invention and/or antibody elicited by such a chemical compound and/or portion thereof or a pharmaceutically acceptable salt or a composition comprising a polypeptide of the invention, and can be administered alone or as an active ingredient in combination with pharmaceutically acceptable carriers, diluents, and vehicles, as well as other active ingredients.

The compounds or compositions can be administered orally, subcutaneously or parenterally including intravenous, intraarterial, intramuscular, intraperitoneally, and intranasal administration as well as intrathecal and infusion techniques.

It is noted that humans are treated generally longer than the mice or other experimental animals which treatment has a length proportional to the length of the disease process and drug effectiveness. The doses may be single doses or multiple doses over a period of several days, but single doses are preferred. Thus, one can scale up from animal experiments, e.g., rats, mice, and the like, to humans, by techniques from this disclosure and documents cited herein and the knowledge in the art, without undue experimentation.

The treatment generally has a length proportional to the length of the disease process and drug effectiveness and the patient being treated.

When administering a therapeutic of the present invention parenterally, it will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions.

Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various amounts of the other ingredients, as desired.

A pharmacological formulation of the present invention, e.g., comprising a therapeutic compound or polypeptide of the present invention, can be administered to the patient in an injectable formulation containing any compatible carrier, such as various vehicles, adjuvants, additives, and diluents; or the compounds utilized in the present invention can be administered parenterally to the patient in the form of slow-release subcutaneous implants or targeted delivery systems such as monoclonal antibodies, iontophoretic, polymer matrices, liposomes, and microspheres.

A pharmacological formulation of the compound and composition comprising a polypeptide utilized in the present invention can be administered orally to the patient. Conventional methods such as administering the compounds in tablets, suspensions, solutions, emulsions, capsules, powders, syrups and the like are usable. Known techniques, which deliver the compound orally or intravenously and retain the biological activity, are preferred.

In one embodiment, a formulation of the present invention can be administered initially, and thereafter maintained by further administration. For instance, a formulation of the invention can be administered in one type of composition and thereafter further administered in a different or the same type of composition. For example, a formulation of the invention can be administered by intravenous injection to bring blood levels to a suitable level. The patient's levels are then maintained by an oral dosage form, although other forms of administration, dependent upon the patient's condition, can be used. In the instance of a vaccine composition, the vaccine may be administered as a single dose, or the vaccine may incorporate set booster doses. For example, booster doses may comprise variants in order to provide protection against multiple clades of HIV.

The quantity to be administered will vary for the patient being treated and whether the administration is for treatment or prevention and will vary from a few micrograms to a few milligrams for an average 70 kg patient, e.g., 5 micrograms to 5 milligrams such as 500 micrograms, or about 100 ng/kg of body weight to 100 mg/kg of body weight per administration and preferably will be from 10 pg/kg to 10 mg/kg per administration. Typically, however, the antigen is present in an amount on, the order of micrograms to milligrams, or, about 0.001 to about 20 wt %, preferably about 0.01 to about 10 wt %, and most preferably about 0.05 to about 5 wt %.

Of course, for any composition to be administered to an animal or human, including the components thereof, and for any particular method of administration, it is preferred to determine therefor: toxicity, such as by determining the lethal dose (LD) and $LD_{50}$ in a suitable animal model e.g., rodent such as mouse; and, the dosage of the composition(s), concentration of components therein and timing of administering the composition(s), which elicit a suitable immunological response, such as by titrations of sera and analysis thereof for antibodies or antigens, e.g., by ELISA and/or RFFIT analysis. Such determinations do not require undue experimentation from the knowledge of the skilled artisan, this disclosure and the documents cited herein. And, the time for sequential administrations can be ascertained without undue experimentation. For instance, dosages can be readily ascertained by those skilled in the art from this disclosure and the knowledge in the art. Thus, the skilled artisan can readily determine the amount of compound and optional additives, vehicles, and/or carrier in compositions and to be administered in methods of the invention. Typically, an adjuvant or additive is commonly used as 0.001 to 50 wt % solution in phosphate buffered saline, and the active ingredient is present in the order of micrograms to milligrams, such as about 0.0001 to about 5 wt %, preferably about 0.0001 to about 1 wt %, most preferably about 0.0001 to about 0.05 wt % or about 0.001 to about 20 wt %, preferably about 0.01 to about 10 wt %, and most preferably about 0.05 to about 5 wt %. Such determinations do not require undue experimentation from the knowledge of the skilled artisan, this disclosure and the documents cited herein. And, the time for sequential administrations can be ascertained without undue experimentation.

Examples of compositions comprising a therapeutic of the invention include liquid preparations for orifice, e.g., oral, nasal, anal, vaginal, peroral, intragastric, mucosal (e.g., perlingual, alveolar, gingival, olfactory or respiratory mucosa) etc., administration such as suspensions, syrups or elixirs; and, preparations for parenteral, subcutaneous, intradermal, intramuscular or intravenous administration (e.g., injectable administration), such as sterile suspensions or emulsions. Such compositions may be in admixture with a suitable carrier, diluent, or excipient such as sterile water, physiological saline, glucose or the like. The compositions can also be lyophilized. The compositions can contain auxiliary substances such as wetting or emulsifying agents, pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Compositions of the invention, are conveniently provided as liquid preparations, e.g., isotonic aqueous solutions, suspensions, emulsions or viscous compositions which may be buffered to a selected pH. If digestive tract absorption is preferred, compositions of the invention can be in the "solid" form of pills, tablets, capsules, caplets and the like, including "solid" preparations which are time-released or which have a liquid filling, e.g., gelatin covered liquid, whereby the gelatin is dissolved in the stomach for delivery to the gut. If nasal or respiratory (mucosal) administration is desired, compositions may be in a form and dispensed by a squeeze spray dispenser, pump dispenser or aerosol dispenser. Aerosols are usually under pressure by means of a hydrocarbon. Pump dispensers can preferably dispense a metered dose or, a dose having a particular particle size.

Compositions of the invention can contain pharmaceutically acceptable flavors and/or colors for rendering them more appealing, especially if they are administered orally. The viscous compositions may be in the form of gels, lotions, ointments, creams and the like (e.g., for transdermal administration) and will typically contain a sufficient amount of a thickening agent so that the viscosity is from about 2500 to 6500 cps, although more viscous compositions, even up to 10,000 cps may be employed. Viscous compositions have a viscosity preferably of 2500 to 5000 cps, since above that range they become more difficult to administer. However, above that range, the compositions can approach solid or gelatin forms, which are then easily administered as a swallowed pill for oral ingestion.

Liquid preparations are normally easier to prepare than gels, other viscous compositions, and solid compositions. Additionally, liquid compositions are somewhat more convenient to administer, especially by injection or orally. Viscous compositions, on the other hand, can be formulated within the appropriate viscosity range to provide longer contact periods with mucosa, such as the lining of the stomach or nasal mucosa.

Obviously, the choice of suitable carriers and other additives will depend on the exact route of administration and the nature of the particular dosage form, e.g., liquid dosage form (e.g., whether the composition is to be formulated into a solution, a suspension, gel or another liquid form), or solid dosage form (e.g., whether the composition is to be formulated into a pill, tablet, capsule, caplet, time release form or liquid-filled form).

Solutions, suspensions and gels, normally contain a major amount of water (preferably purified water) in addition to the active compound. Minor amounts of other ingredients such as pH adjusters (e.g., a base such as NaOH), emulsifiers or dispersing agents, buffering agents, preservatives, wetting agents, jelling agents, (e.g., methylcellulose), colors and/or flavors may also be present. The compositions can be isotonic, i.e., it can have the same osmotic pressure as blood and lacrimal fluid.

The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions may be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected. The important point is to use an amount that will achieve the selected viscosity. Viscous compositions are normally prepared from solutions by the addition of such thickening agents.

A pharmaceutically acceptable preservative can be employed to increase the shelf-life of the compositions. Benzyl alcohol may be suitable, although a variety of preservatives including, for example, parabens, thimerosal, chlorobutanol, or benzalkonium chloride may also be employed. A suitable concentration of the preservative will be from 0.02% to 2% based on the total weight although there may be appreciable variation depending upon the agent selected.

Those skilled in the art will recognize that the components of the compositions should be selected to be chemically inert with respect to the active compound. This will present no problem to those skilled in chemical and pharmaceutical principles, or problems can be readily avoided by reference to standard texts or by simple experiments (not involving undue experimentation), from this disclosure and the documents cited herein.

It is generally envisaged that compounds and compositions of the invention will be administered by injection, as such compounds are to elicit anti-HIV antibodies, and the skilled artisan can, from this disclosure and the knowledge in the art, formulate compounds and compositions identified by herein methods for administration by injection and administer such compounds and compositions by injection.

The inventive compositions of this invention are prepared by mixing the ingredients following generally accepted procedures. For example the selected components may be simply mixed in a blender, or other standard device to produce a concentrated mixture which may then be adjusted to the final concentration and viscosity by the addition of water or thickening agent and possibly a buffer to control pH or an additional solute to control tonicity. Generally the pH may be from about 3 to 7.5. Compositions can be administered in dosages and by techniques well known to those skilled in the medical arts taking into consideration such factors as the age, sex, weight, and condition of the particular patient, and the composition form used for administration (e.g., solid vs. liquid). Dosages for humans or other mammals can be determined without undue experimentation by the skilled artisan, from this disclosure, the documents cited herein, and the knowledge in the art.

Suitable regimes for initial administration and further doses or for sequential administrations also are variable, may include an initial administration followed by subsequent administrations; but nonetheless, may be ascertained by the skilled artisan, from this disclosure, the documents cited herein, and the knowledge in the art.

Accordingly, the invention comprehends; in further aspects, methods for preparing therapeutic or preventive compositions including an active agent, ingredient or compound or neutralizing antibody, such as PGT 127 or PGT 128, binder as from inventive methods herein for ascertaining compounds that bind to, as well as to methods for inhibiting HIV or eliciting antibodies against HIV by administering a compound or compounds that bind to a neutralizing antibody, such as PGT 127 or PGT 128.

Furthermore, as discussed herein, compounds which bind to a neutralizing antibody, such as PGT 127 or PGT 128, are useful in generating antibodies, which are themselves useful in assays as well as in therapeutics as well as diagnostics; and, the compounds which bind to PGT 127 or PGT 128 are useful for detecting anti-HIV antibodies in a sample. From documents cited herein, one can readily make and use such antibodies, and methods for producing monoclonal antibodies are well known to those of ordinary skill in the art, see, e.g., U.S. Pat. Nos. 4,196,265 and 6,221,645. Thus, the compounds that bind to a neutralizing antibody, such as PGT 127 or PGT 128, can be used to generate antibodies and the antibodies can be used, without undue experimentation, e.g., to detect HIV immunogens, antigens or epitopes in a sample.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1: An Exceptionally Potent and Broad Neutralizing Antibody Recognizes and Penetrates the HIV Glycan Shield HIV Antibody PGT 128 achieves extraordinary potency and breadth by multivalent binding of its Fab to two glycans and the backbone of the V3 loop on gp120.

Furthermore, Applicants' data suggest that the high neutralization potency of PGT 127 and The HIV envelope (Env) protein gp120 is protected from antibody recognition by a dense glycan shield. However, several of the recently identified PGT broadly neutralizing antibodies appear to interact directly with the HIV glycan coat. Crystal structures of Fabs PGT 127 and 128 with $Man_9$ at 1.65 and 1.29 Å resolution, respectively, and glycan binding data delineate a specific high mannose binding site. Fab PGT 128 complexed with an engineered fully-glycosylated gp120 outer domain at 3.25 Å reveals that the antibody penetrates the glycan shield and recognizes two conserved glycans as well as a short β-strand segment of the gp120 V3 loop, accounting for its high binding affinity and broad specificity. PGT 128 IgGs may be mediated by cross-linking Env trimers on the viral surface.

Viruses have evolved a variety of mechanisms to escape antibody recognition, many of which involve features of the viral surface proteins, such as high variability, steric occlusion, and glycan coating. For HIV, the dense shield of glycans (1, 2) that decorate the viral Env protein was once believed to be refractory to antibody recognition, shielding conserved protein epitopes of important functional significance whose greater exposure would result in increased susceptibility to antibody neutralization. However, bnMAb 2G12 and several of the recently described PGT antibodies appear to bind directly to the HIV glycan coat. Although carbohydrate-protein interactions are typically weak (3), 2G12 recognizes terminal Manα1,2Man moieties on oligomannose glycans using a unique domain-exchanged antibody structure that creates a multivalent binding surface and enhances the affinity of the interaction through avidity effects (4). However, although 2G12 neutralizes clade B isolates broadly, it is less effective against other clades, in particular clade C viruses that have a somewhat different oligomannose glycan arrangement to clade B viruses. In contrast, Applicants have recently isolated six bnMAbs (PGTs 125-128, 130-131) that bind specifically to the $Man_{8/9}$ glycans on gp120 and neutralize across clades with exceptional breadth and potency (5). PGT 128, the broadest of these antibodies, neutralizes over 70% of globally circulating viruses and is, on average, an order of magnitude more potent than the recently described PG9, PG16, VRC01, and VRC-PG04 bnMAbs (6-8) and two orders of magnitude more potent than prototype bnMAbs described earlier (6, 9).

The neutralization potency exhibited by the PGT class of antibodies suggests that they may provide protection at relatively low serum concentrations. Hence, the epitopes recognized by these antibodies may be good vaccine targets if appropriate immunogens can be designed.

Crystal Structures of PGTs 127 and 128 Bound to $Man_9$.

Figures 8A, 8B:
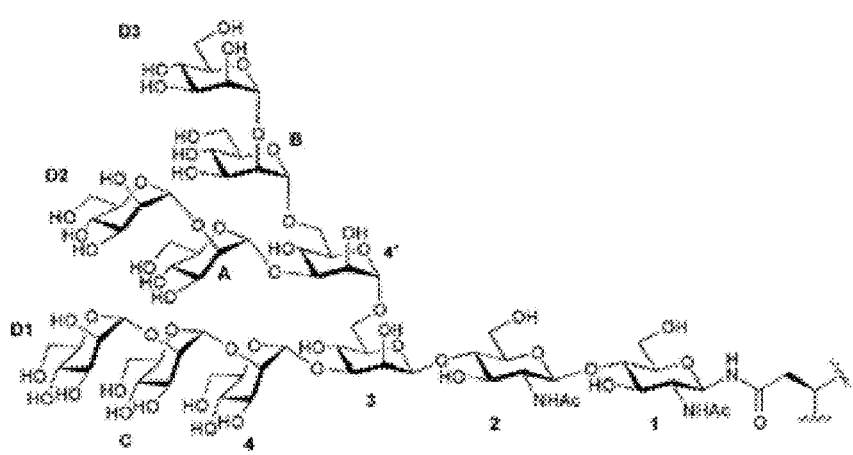
FIG. 8. Dihedral and conformational analysis of Man$_9$ conformation when bound to PGT 128. (A) Chemical representation of Man$_9$GlcNAc$_2$ showing standard nomenclature. (B) Torsional analysis of glycosidic linkages of Man$_9$ bound to PGT 128. †Reference dihedral angles with standard deviations were obtained from Petrescu et al. (74). ‡Dihedral angles follow the "x−1" system for crystallography and are defined as: φ=O5-C1-O-C(x)' and ψ=C1-O-C(x)'-C(x−1)' for Man(α1→2)Man and Man(α1→3)Man, where x=2 or 3 respectively; φ=O5-C1-O-C6', ψ=C1-O-C6'-C5', and ω=O-C6'-C5'-C4' for Man(α1→6)Man linkages. Note equivalence of positive angles over 180 with corresponding negative angles e.g. −169.6°=190.4°. S21 (C) Carbohydrate Ramachandran plots (ψ/φ) of glycosidic linkages (red) compared to with other database values (gray). The axes are now in the "x−1" system rather than the "x+1" system (75). (D) Superposition of PGT 128-bound Man$_9$ (green and red sticks) with 10 other Man$_9$ structures taken from the PDB.

To gain a structural understanding of the specificity for $Man_8GlcNAc_2$ and $Man_9GlcNAc_2$ glycans by PGTs 127 and 128, Applicants first determined crystal structures of the antigen-binding fragments (Fabs) of PGTs 127 and 128 with a synthetic $Man_9$ glycan lacking the core N-acetylglucosamine (GlcNAc) moieties at 1.65 and 1.29 Å resolution, respectively (Table S1). The bound glycan is well ordered, except for the terminal mannose residue of the D2 arm (FIG. 1, FIG. 7 and FIG. 8A). The PGT 127/$Man_9$ and PGT 128/$Man_9$ structures show highly similar conformations for the glycan (FIG. 7), demonstrating a conserved mode of recognition by these clonally related antibodies.

Figure 8C:
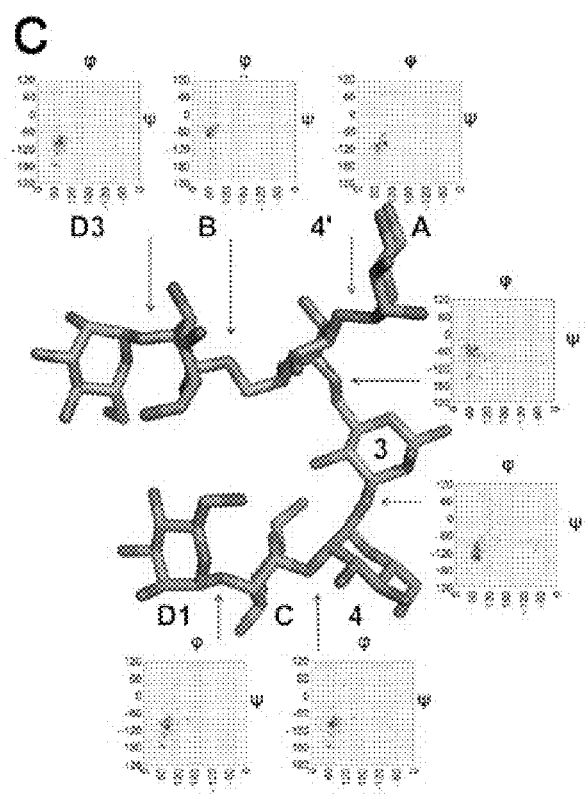
Figure 8D:
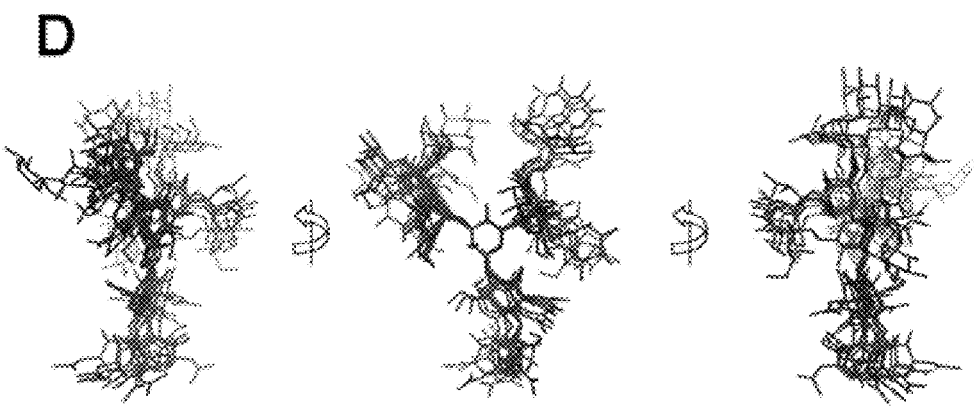
Figure 9A:
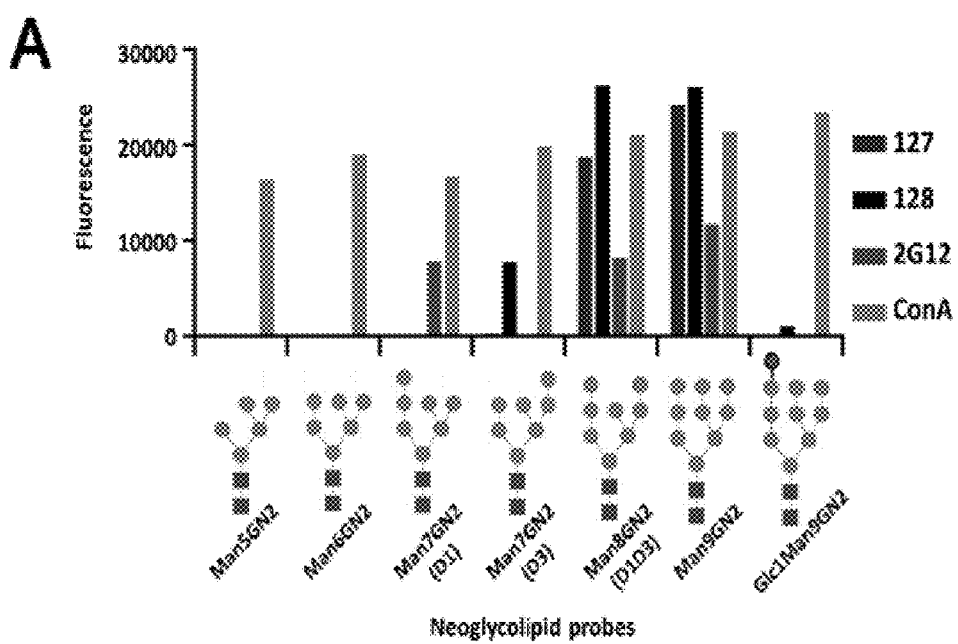
FIG. 9. Glycan specificity profiling of PGTs 127 and 128. (A) Binding of PGTs 127 and 128, and antibody 2G12 to oligomannose and glucosylated Man$_9$ N-glycans arrayed (5 fmol) in the neoglycolipid microarrays. Concanavalin A (ConA) is included as a positive control. The full array data with 50 oligosaccharide probes are in Table S6. (B) Glycosidase inhibition studies with PGTs 127 and 128 and 2G12 on HIV-1$_{JR-FL}$. Pseudovirus was prepared in the presence of 25 μM kifunensine (ER-mannosidase I enzyme) to generate virus displaying Man$_9$GlcNAc$_2$ glycans and/or 2 mM NB-DNJ (ER-α-glucosidase I and II enzymes) to generate virus displaying Glc$_{1-3}$Man$_9$GlcNAc$_2$ glycans. Due to the endomannosidase activity present in 293T cells, virus was also prepared in the presence of NB-DNJ and kifunensine.
Figure 9B:
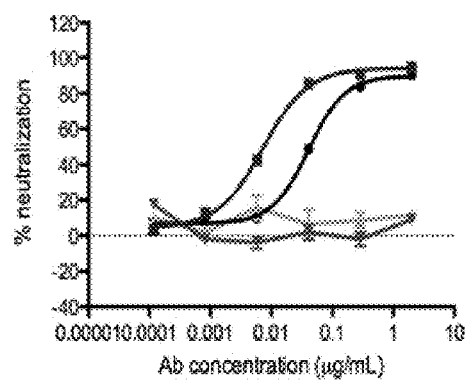
Figure 9B:
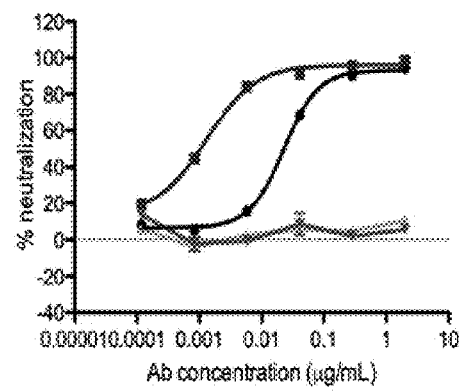
Figure 9B:
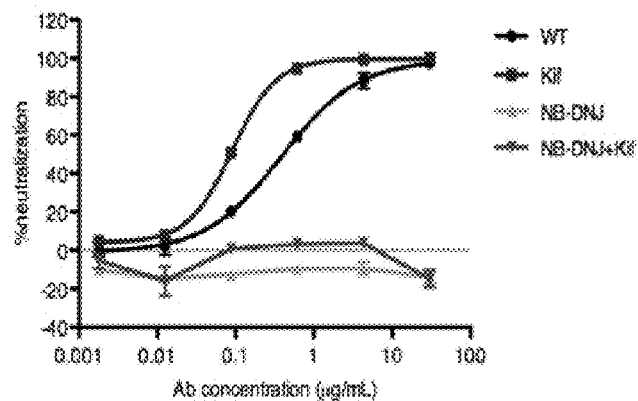

Analysis of these crystal structures reveals the origin of their specificity for $Man_{8/9}$ glycans. The terminal mannose residues of both the D1 and D3 arms, which are only present on $Man_{8/9}$ glycans (FIG. 1B and FIG. 8A), are heavily contacted, forming 11 of the 16 total hydrogen bonding interactions with the antibody (Table S2). This specificity for glycans is consistent with glycan array data showing binding of PGT127/8 to $Man_8$ and $Man_9$, but not to monoglucosylated $Man_9$ N-glycans (FIG. 9A), and with glycosidase inhibitor specificity profiling (FIG. 9B). The D3 arm of $Man_{8/9}$ is bound by CDR L3 Asn94, Trp95, and Asp 95a (FIG. 1C and Table S2). Several ordered water molecules are present in the glycan-antibody interface and also bridge the mannose residues (FIG. 1C), as previously noted as key features of other antibody-carbohydrate interfaces (10). In addition, two hydrogen bonds are observed between mannose residues that reside on different arms. The individual dihedrals of the glycan are in stable, low energy conformations (FIG. 8), consistent with a high affinity interaction.

Figure 3A:
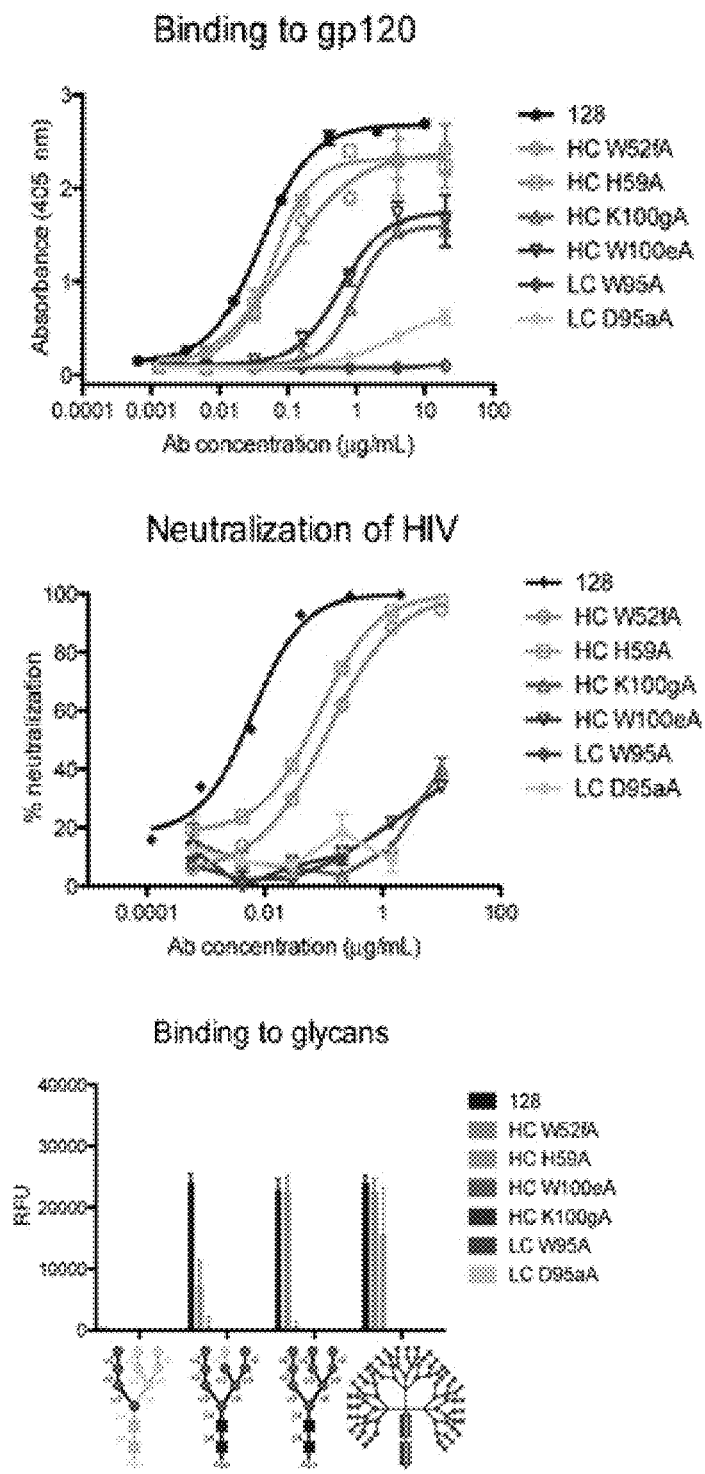
FIG. 3. Effect of PGT 128 paratope mutations in the individual glycan subsites on neutralization of HIV-1$_{JR-FL}$ and glycan binding. Binding of PGT 128 mutants to gp120 was tested by ELISA (left panel) or to glycans on the high mannose glycan microarray (right panel). (A) Mutation of select residues in the primary glycan binding site (Man$_{8/9}$) that recognizes the N332 glycan. Residues (HC, heavy chain; LC, light chain) that disrupt the formation of the hydrophobic core of the binding site ($V_H$ K100gA, W100eA, and $V_L$ W95A) or disrupt hydrogen bonding to terminal mannose residues ($V_H$ H59A and $V_L$ D95aA) compromise neutralization (middle panel), as well as gp120 and glycan binding. (B) Mutation of select residues interacting with the secondary glycan binding site that recognizes the N301 glycan. Mutation of $V_H$ H52aA results in a decrease in gp120 binding and neutralization, while disruption of the CDR H1-H2 disulfide ($V_H$C32A, C52bA, or double mutant) greatly compromises both gp120 binding and neutralization. (C) Contribution of the 6-residue CDR H2 insert deletion on neutralization and glycan binding ("RSYYNT" disclosed as SEQ ID NO: 2 and "ASYWNR" disclosed as SEQ ID NO: 3. PGT 128 retains ability to bind Man$_{8/9}$ and neutralize to a lesser extent without the insert, whereas PGT 127 no longer neutralizes, although still has some ability to bind Man$_{8/9}$. Swapping of the insert between 127 and 128 allows 128 to retain some binding and neutralization, but substantially reduces binding and abrogates neutralization when the PGT 128 H2 insert is transplanted onto PGT 127.
Figure 3B:
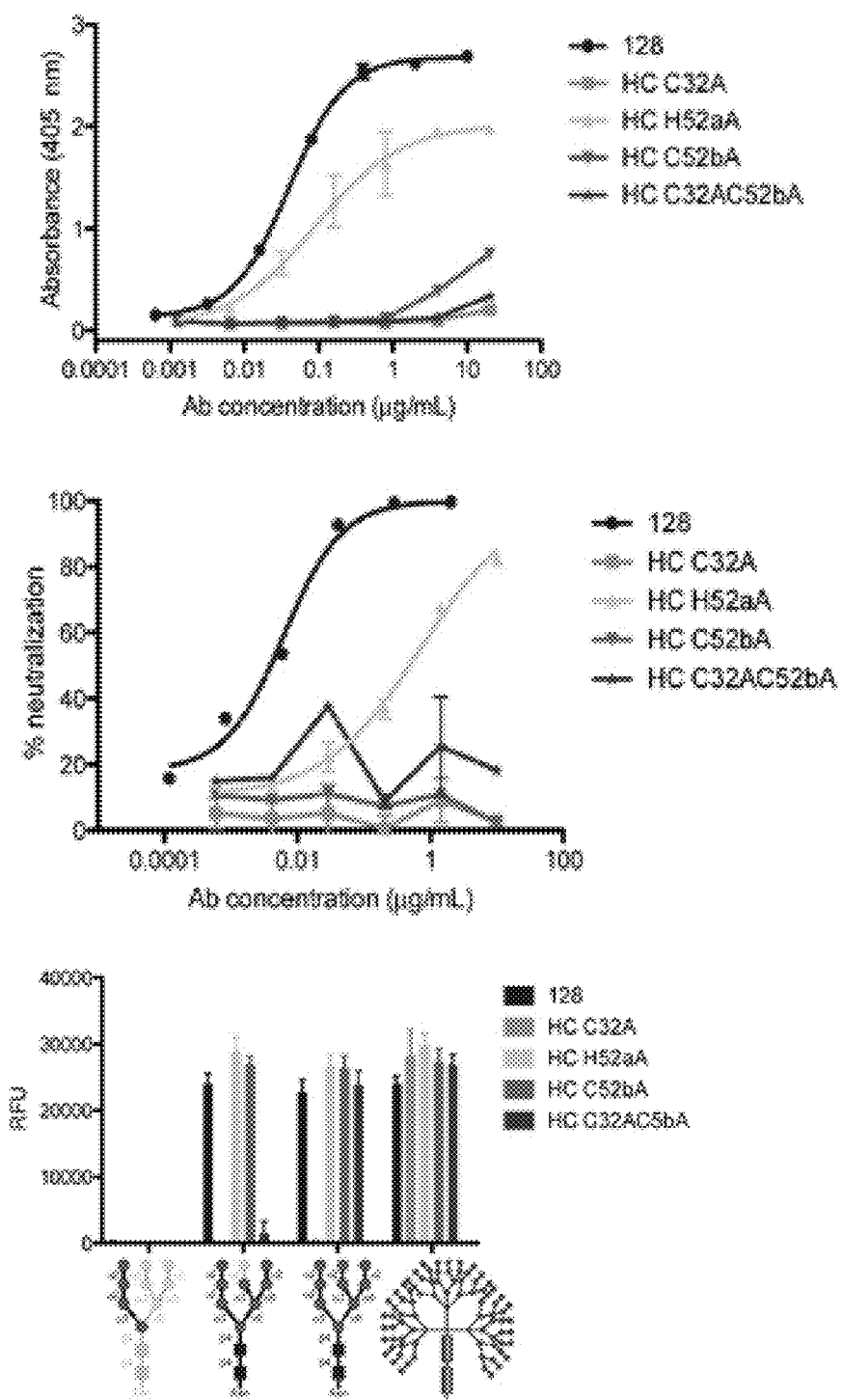
Figure 3C:
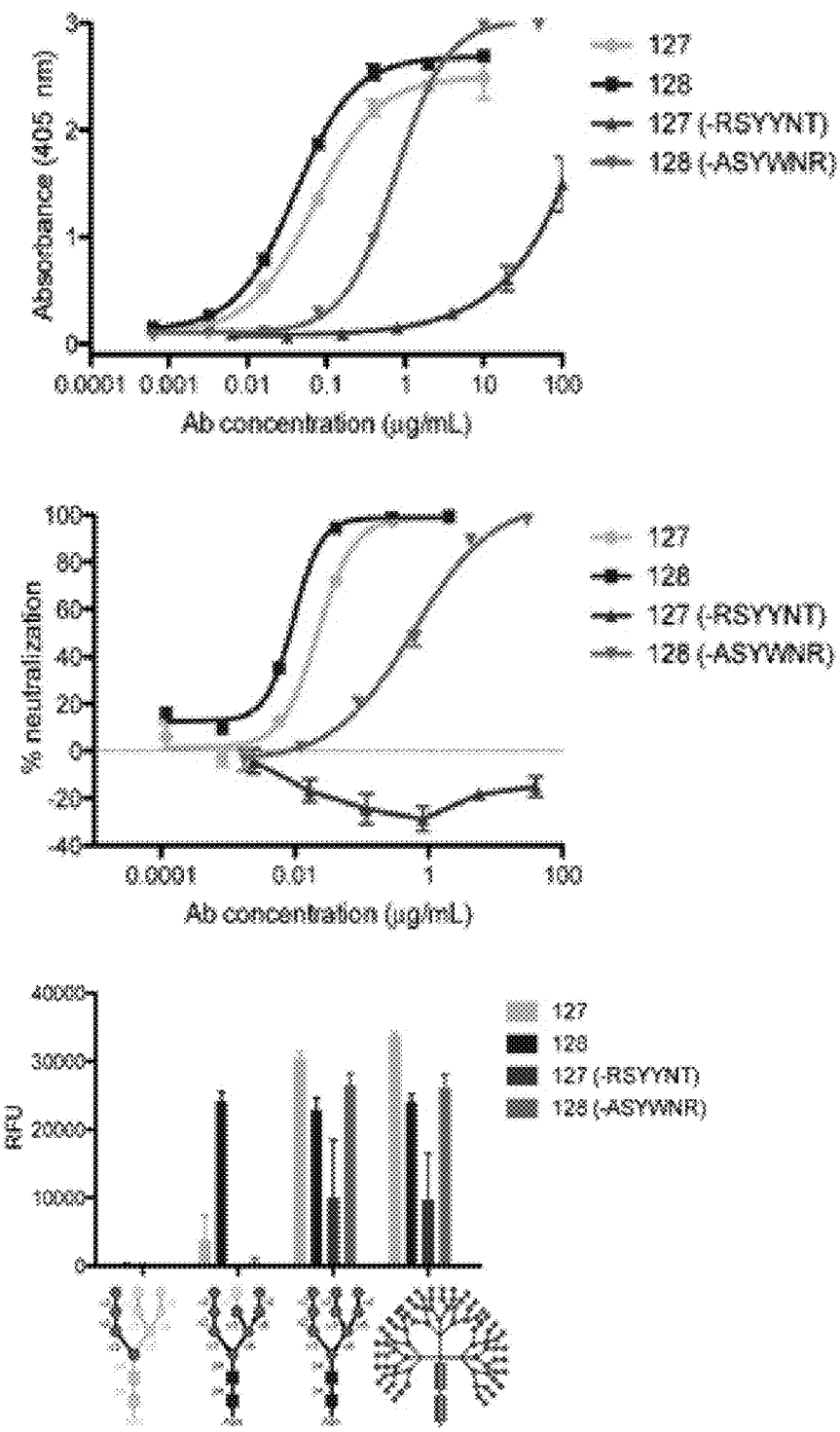
Figure 10:
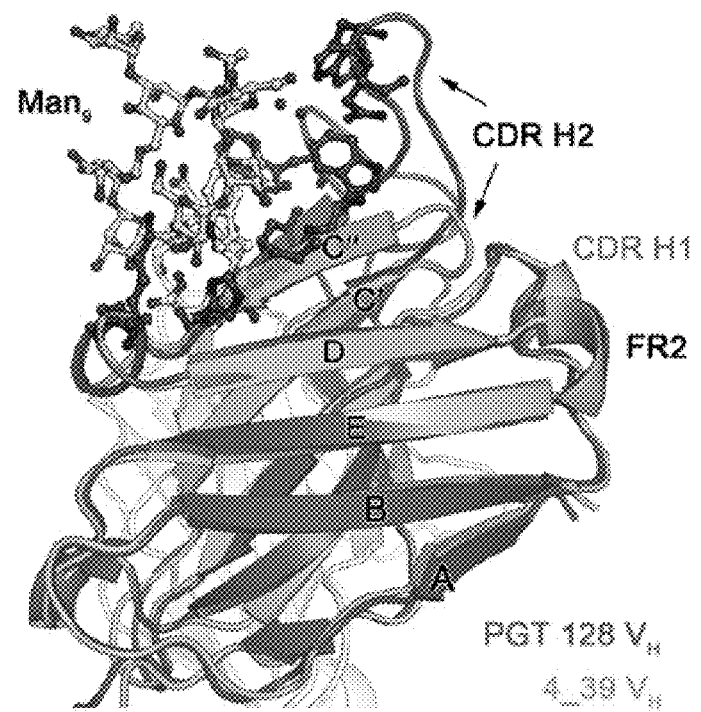
FIG. 10. Comparison PGT 128 V$_H$ domain to germline IGHV 4_39 model. (left) side view of the superposition of a model IGHV 4_39 V$_H$ domain derived from PDB entry 2J6E (green) with PGT 128 V$_H$ (purple). The C" β-strand is displaced by the 6-residue CDR H2 insertion. (right) Top-down view of superposition.
Figure 10:
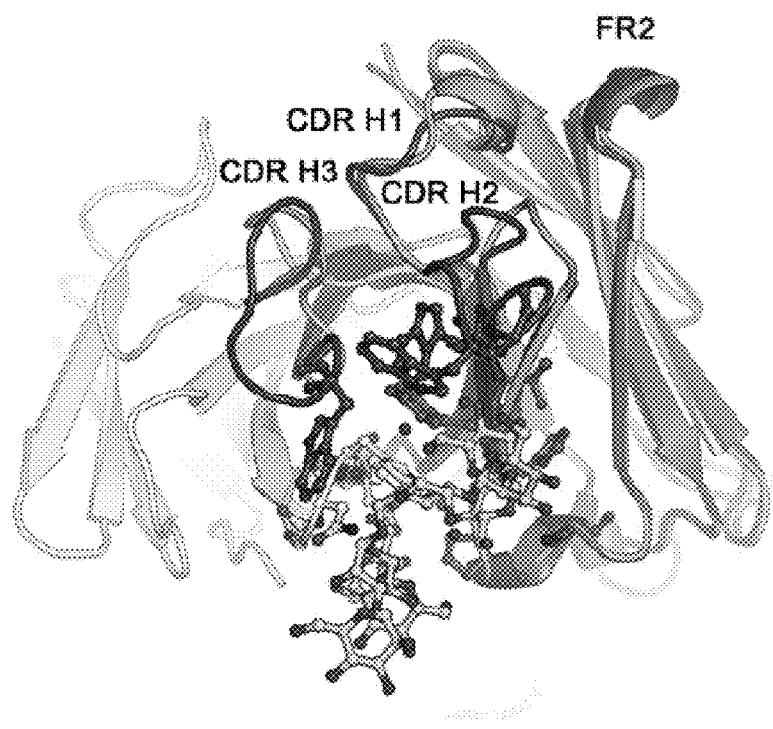
Figure 11A:
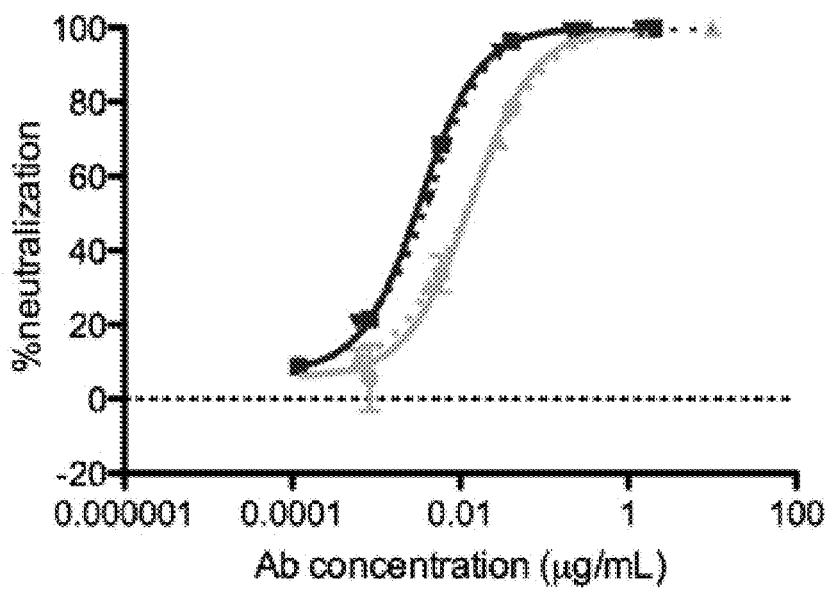
FIG. 11. PGT 127 and 128 CDR H2 6-residue insert swap and effect on neutralization potency. Neutralizing activity of antibodies against (A) WT JR-CSF, (B) JRCSF N332A, and (C) 92TH021. Residues RSYYNT (SEQ ID NO: 2) in PGT 127 were replaced with ASYWNR (SEQ ID NO: 3) and residues ASWNR (SEQ ID NO: 3) in PGT 128 were replaced with RSYYNT (SEQ ID NO: 2).
Figure 11B:
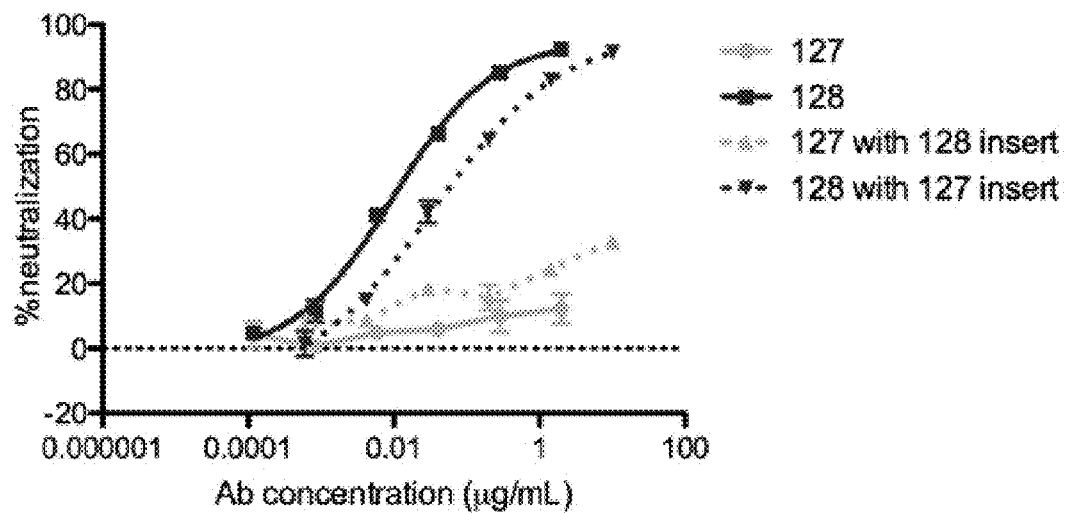

PGTs 125-128 contain a 6-residue insertion in CDR H2 (5), which was likely introduced somatically during affinity maturation (11). This insertion mediates an outward displacement of the C" β-strand of $V_H$ (FIG. 10) and promotes contact with the $Man_9$ D1 arm (FIG. 1 and Table S2). Deletion of the insert resulted in diminished gp120 binding and neutralization potency for PGTs 127 and 128 (FIG. 3C). However, a reciprocal swap of the PGT 127 and 128 insert residues did not result in a complete interchange of their binding to gp120 or their neutralization profiles (FIG. 3C and FIG. 11), indicating that the insert does not solely account for their differences in breadth and potency (12-13). The high affinity for $Man_9$ is explained by its extensive buried surface area (394 Å2 by PGT 128 and 352 Å2 by PGT 127) (Table S2) in a binding mode that differs from other carbohydrate-binding antibodies or lectins and notably from 2G12, which only contacts the terminal Manα1,2Man moieties of $Man_9$, particularly at the tip of the D1 arm (4).

Crystal Structure of PGT 128 Bound to a Glycosylated Gp120 Outer Domain.

Figures 11C, 12:
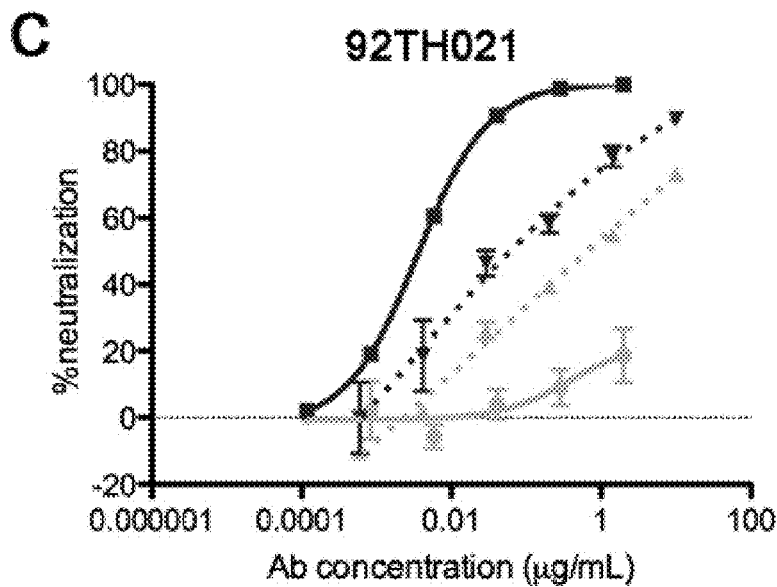
FIG. 12. Amino-acid sequence of engineered outer domain construct containing mini-V3 (SEQ ID NO: 12). The locations of mini-V3 (dashed line), N301 (*) and N332 (●) are indicated. The base strain for eOD is HxB2; mini-V3 (mV3) is based on JR-FL and corresponds to V3 loop residues 298-304 and 321-329.
Figure 13:
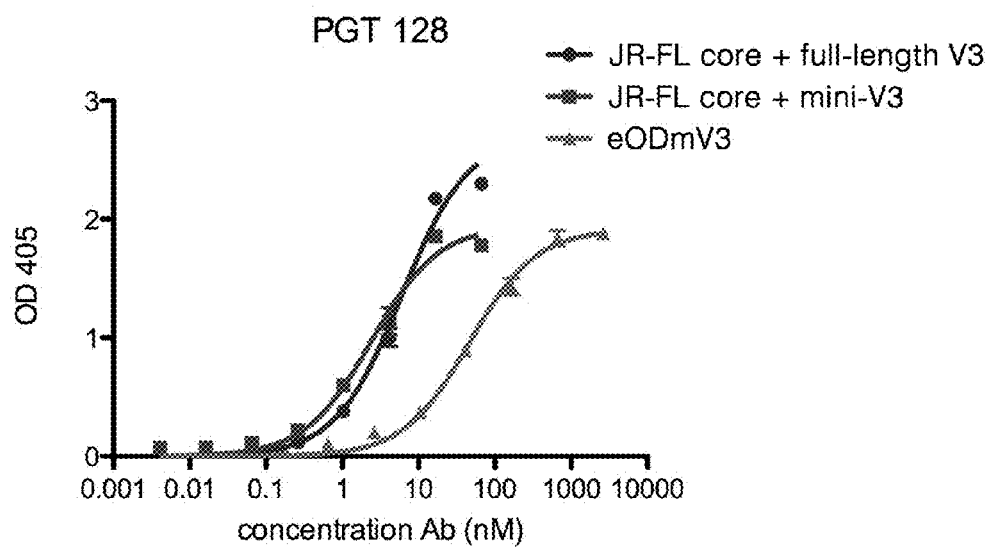
FIG. 13. Binding of IgG PGT 128 to HIV envelope constructs. ELISA binding of IgG PGT 128 to HIV-1$_{JR-FL}$ core gp120 with a full-length V3 (blue circles), HIV-1$_{JR-FL}$ core gp120 with mini-V3, containing a deletion of residues 305-320, (maroon squares) and eODmV3 (green triangles).

To structurally define the epitope recognized by PGT 128 in the context of gp120, Applicants co-crystallized Fab PGT 128 with a glycosylated gp120 outer domain construct containing a truncated V3 loop (engineered outer domain mini-V3; eODmV3 (14)) (FIG. 12). PGT 128 binds to eODmV3 with an apparent affinity of 46 nM, which is ~8-fold less than its interaction with HIV-1JR-FL gp120 core with a full-length V3 (FIG. 13). The purified complex was homogenous as assessed by SEC-MALS (FIG. 14) and the crystal structure was solved by molecular replacement and refined to an $R_{cryst}$ of 0.21 and $R_{free}$ of 0.26 (Table S1).

Figure 2:
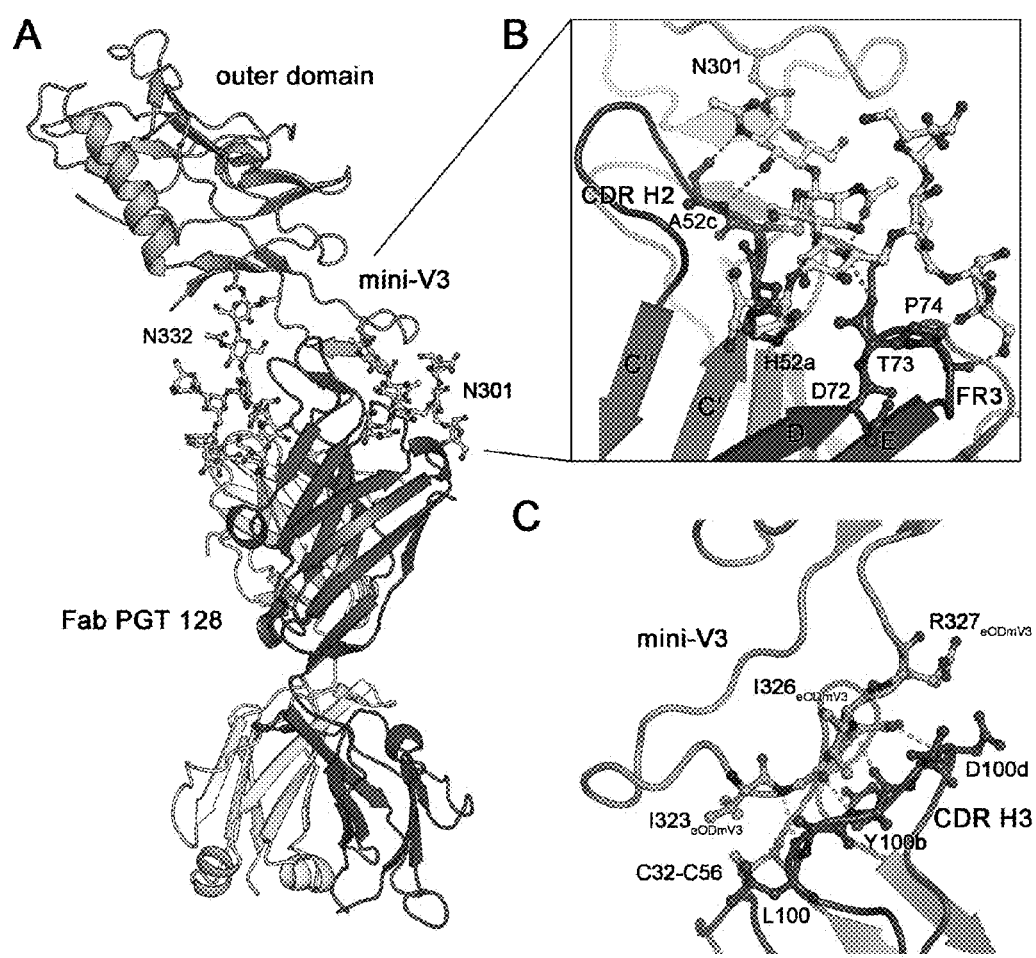
FIG. 2. Crystal structure of PGT 128 Fab in complex with an engineered glycosylated gp120 outer domain (eODmV3). (A) Overall view of PGT128/eODmV3. PGT128 Fab heavy and light chains are depicted as in FIG. 1. eODmV3 is shown in green cartoon ribbon representation. Glycans are depicted in a ball-and-stick representation. PGT128 binds the N332 glycan in the primary glycan binding site by interactions with the terminal mannose residues of the D1 and D3 arms. The mode of interaction and site of recognition is identical to that visualized in the high resolution Man$_9$ complex. The secondary glycan binding site recognizes the N301 glycan. (B) Close up view of the secondary glycan interaction site and contacts made with N301 glycan. The mannose residues of the N301 glycan splay out around FR3 residues D72, T73, P74, and K75. The terminal mannose resides are not ordered in the electron density. (C) Close up view of V3 interactions with CDR H3. The C-terminus of V3, residues D325-Q328, make van der Waals and hydrogen bonding contacts to one side of an extended β-strand region of PGT 128 CDR H3, which includes L100-D100d. The V3 base is intercalated between the apex of the H2 insert (Y52e and W52f) and H3.

The crystal structure unexpectedly revealed that PGT 128 in fact engages two different glycans, as well as the C-terminal end of the V3 loop, within the binding site. The primary glycan-binding site is occupied by the high-mannose glycan attached to N332 ($Man_{8/9}GlcNAc_2$), while a secondary glycan-binding site is occupied by N301, which appears as $Man_5GlcNAc_2$ in the electron density maps (FIG. 2). The secondary glycan-binding site is focused on the core pentasaccharide of N301, as only the $Man_5GlcNAc_2$ portion of the glycan is visible in the density map (FIG. 2B). The two GlcNAc residues bind atop the CDR H1-H2 disulfide in a favorable hydrophobic interaction; hydrogen bonds are formed between the backbone amide and carbonyl of Ala52c and the N-acetyl and 03 hydroxyl of the first Asn-linked GlcNAc. FR3 and CDR H1 residues form the contact site for the mannose sugars (FIG. 2B and Table S4).

The CDR H3 apex contacts the V3 loop on the gp120 outer domain. The C-terminal residues of V3, Ile323-Arg327, are bound in a groove between CDRs H2 and H3. Leu100-Asp100d in CDR H3 adopt a β-strand conformation that is primed for β-sheet type interactions with the gp120 V3 loop (15).

To assess the importance of the individual glycan binding sites for epitope recognition, A series of antibody variants containing single amino-acid substitutions were tested in each subsite. Mutations in the primary glycan binding site (N332) compromised neutralization, gp120 binding, and binding to $Man_{8/9}$ on the glycan array (FIG. 3A and Table S3). Although numerous interactions are made with the glycan, including a total of 17 hydrogen bonds, disruption of the bidentate interaction between Man D3 and CDR L3 Asp95a resulted in a loss of gp120 and glycan binding and neutralizing activity (FIG. 3A). Mutation of residues involved in the secondary site (N301), particularly the H1-H2 disulfide, also resulted in a loss of gp120 binding and virus neutralization (FIG. 3B and Table S3). Nevertheless, the affinity of this secondary glycan binding site (N301) was too low to detect directly by glycan array, as evidenced by lack of glycan binding capacity by a primary glycan-binding site loss-of-function variant (VL Asp95a→Ala). Also, mutation of FR3 and CDR H1 that interact with the mannose residues in the secondary binding site generally had little to no effect on neutralization by PGT 128, suggesting that the interactions with the mannose residues in the secondary site are not as crucial as the GlcNAc interactions (Table S3). Notwithstanding, the N301 glycan is required for high-affinity binding to gp120 and neutralization. The importance of the N332 and N301 glycans in forming the PGT 128 epitope was confirmed by alanine scanning mutagenesis where substitutions at positions 332 and 301 resulted in loss of neutralizing activity against most isolates tested (Table S5). PGT 127 displayed a similar glycan reactivity profile as PGT 128 against most isolates, suggesting that the two antibodies share a similar conserved mode of epitope recognition.

Figure 15:
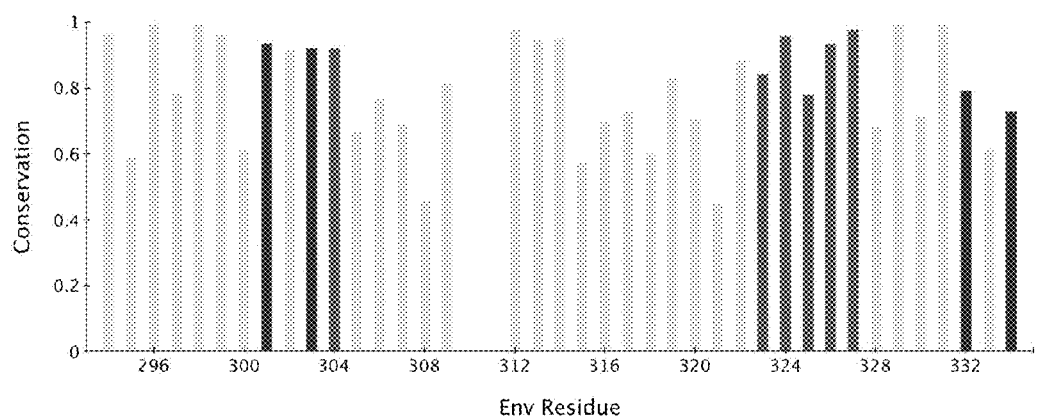
FIG. 15. Conservation of V3 stem residues and glycans that form the epitope of PGT 128. Conservation of residues among >1600 aligned sequences taken from the Los Alamos HIV sequence database. N301 and N332 NXS/T glycan sequons are depicted as blue bars, and other amino acids involved as direct contact residues in the PGT 128 epitope are shown as green bars.
Figure 16A:
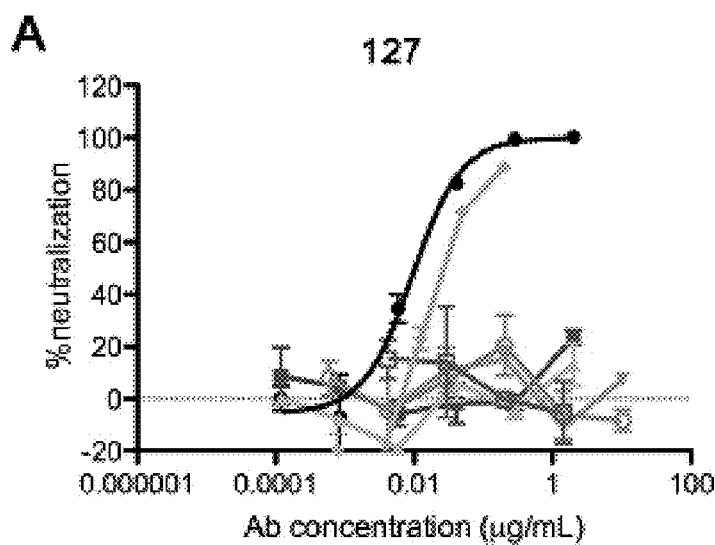
FIG. 16. Neutralizing activity of PGTs 127 and 128 against single and double HIV-1$_{JR-CSF}$ glycan mutants. One or two N-linked glycans (N295, N301 or N332) were removed from HIV-1$_{JR\text{-}CSF}$, and PGTs 127 and 128 were tested for neutralizing activity.
Figure 16B:
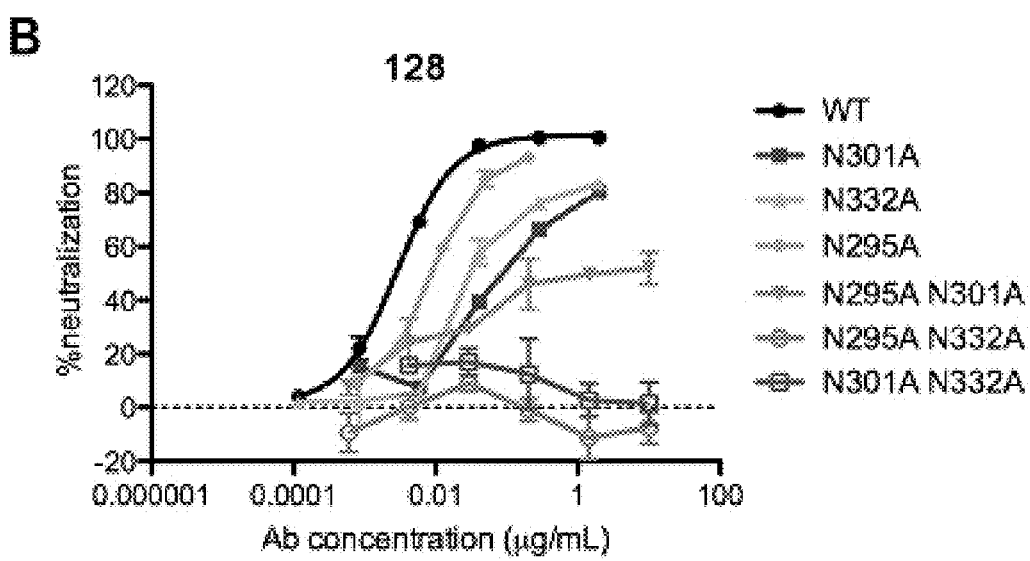
Figure 17A:
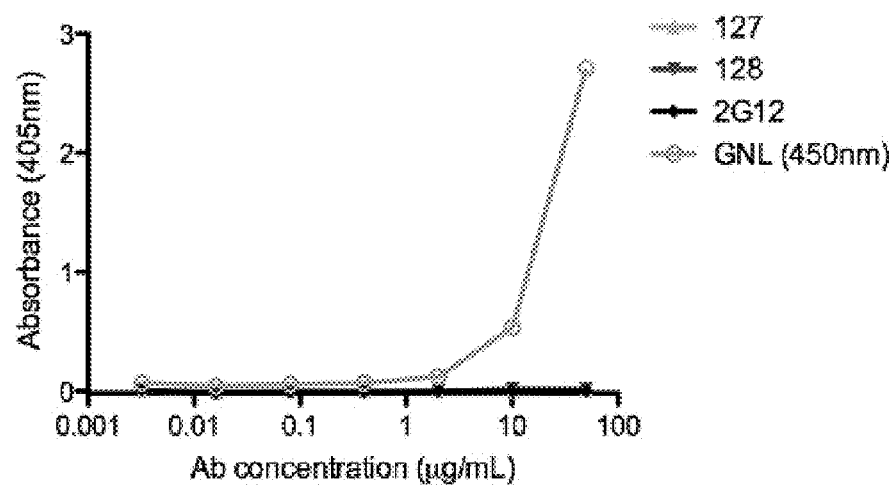
FIG. 17. Lack of binding of PGTs 127 and 128 to self-glycoproteins and glycoproteins displaying high-mannose glycans. (A) RNAse B and (B) human C3. bnMAb 2G12 and *Galanthus nivalis* lectin (GNL) are included as controls. Anti-C3 is a goat-anti-human polyclonal raised against human C3. Anti-serum was used at an initial dilution of 1:50. GNL and the anti-goat secondary were HRP conjugated and absorbance read at 450 nm.
Figure 17B:
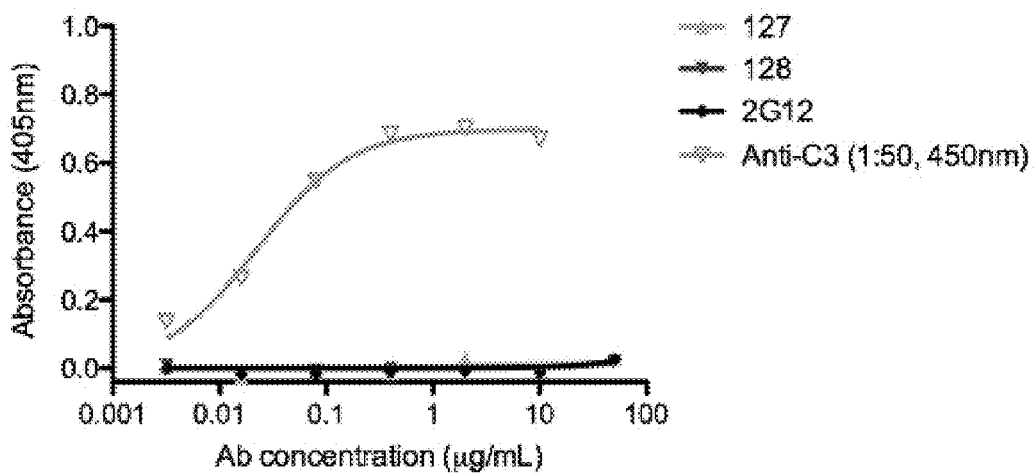
Figure 18A:
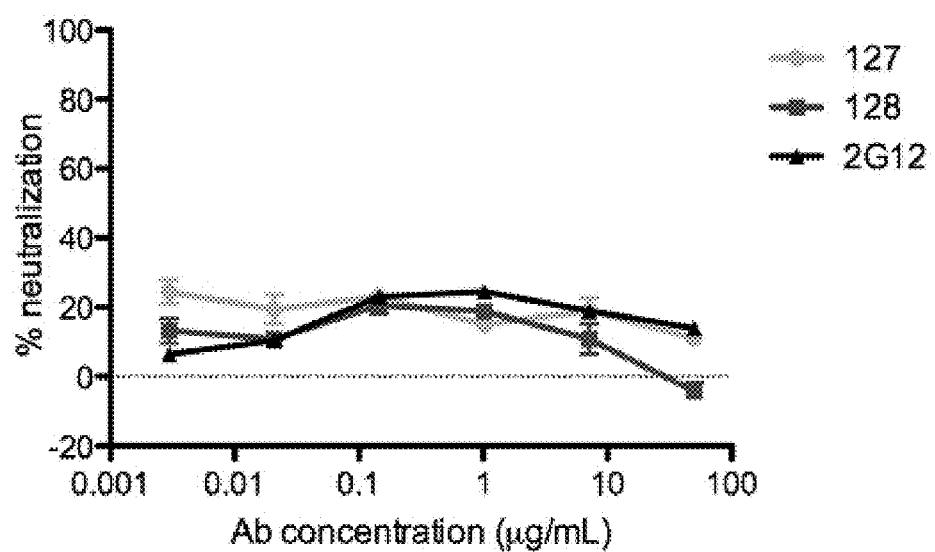
FIG. 18. Neutralization of other highly glycosylated viruses by PGT 127 and 128. Neutralization of (A) SIV mac239 and (B) HIV-2 was measured in a single round replication pseudovirus assay with TZM-bl target cells. No neutralization was observed as with 2G12.
Figure 18B:
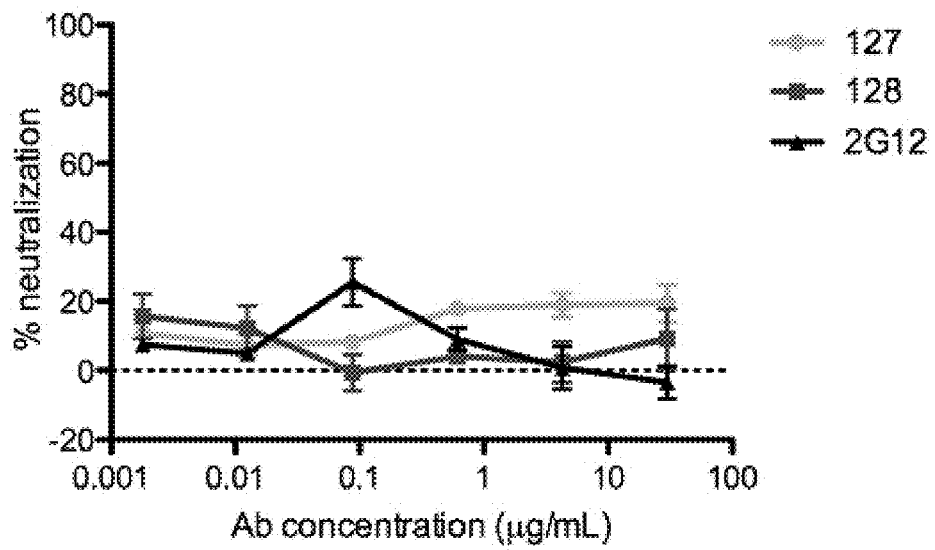

Notably, the N301 and N332 glycans are 93% and 73% conserved among HIV isolates (FIG. 15), respectively, which accounts for the ability of PGT 128 to neutralize 72% of circulating viruses. Interestingly, in the context of HIV-$1_{JR-CSF}$, individual alanine mutations at positions 332 and 301 had little to no effect on neutralization by PGT 128 (5), but various combinations of double glycan substitutions completely abolished neutralizing activity (FIG. 16). These results suggest that, for JR-CSF, the epitope may be more promiscuous and accommodate antibody binding to two out of three glycans. The PGT 128 requirement for two closely spaced N-linked glycans (Table S5 and FIG. 16) likely accounts for its lack of reactivity with self-glycoproteins displaying single $Man_{8/9}GlcNAc_2$ (FIG. 17) and for resistance of HIV-2 and SIV viruses to neutralization (FIG. 18). Specific interactions with V3 were more difficult to investigate, as the V3 contacts with PGT 128 CDR H3 are primarily mediated through backbone hydrogen bonding and van der Waals interactions that are tolerant of side-chain variation, as seen for the V3 crown-specific antibody 447-52D (16). Thus, three discontinuous sites on the gp120 outer domain (449 Å$^2$ from N332, 328 Å$^2$ from N301, and 305 Å$^2$ from V3) combine to form 1081 A2 of buried surface area (Table S4), which is similar in overall size to other anti-HIV bnMAbs VRC01 and VRC-PG04 that bury 1229 Å$^2$ and 1080 Å$^2$ on the CD4 binding site of core gp120, respectively (8, 17).

The PGT 128 Epitope is Highly Accessible on the HIV Trimer.

Figure 4:
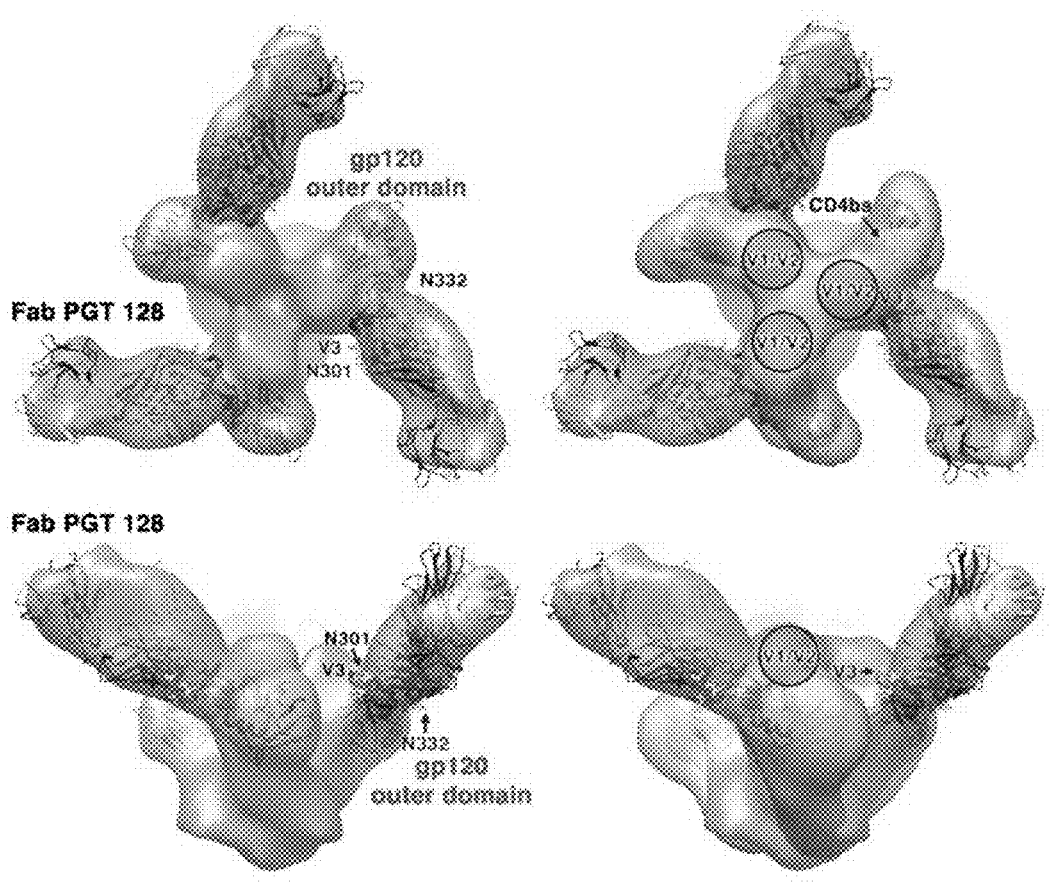
FIG. 4. Negative stain reconstruction of partially-deglycosylated soluble 664G Env trimer in complex with PGT128 Fab. Soluble (664G) Env trimer was complexed with Fab PGT 128 and treated with Endo H to remove non-protected glycans. (A) Coordinates of the 128/eODmV3 complex structure fitted into the reconstruction density (blue). Overhead (top) and side (bottom) views show the fit of the crystal structure to the EM density. Fab 128, depicted as blue (heavy) and white (light), and eODmV3 (red) are depicted in schematic backbone representation with glycans shown as yellow sticks. (B) Reconstruction density overlayed with cryo-electron tomographic reconstruction of native, unliganded trimer (yellow) (30). The putative location of V1/V2 is indicated. V3 N301 and N332 are exposed on the surface of the outer domain and slightly below the trimer apex, which corresponds to location of the V1/V2 loops. The PGT 128 epitope located approximately on the opposite side of gp120 from the CD4bs (FIG. 19C).
Figure 5A:
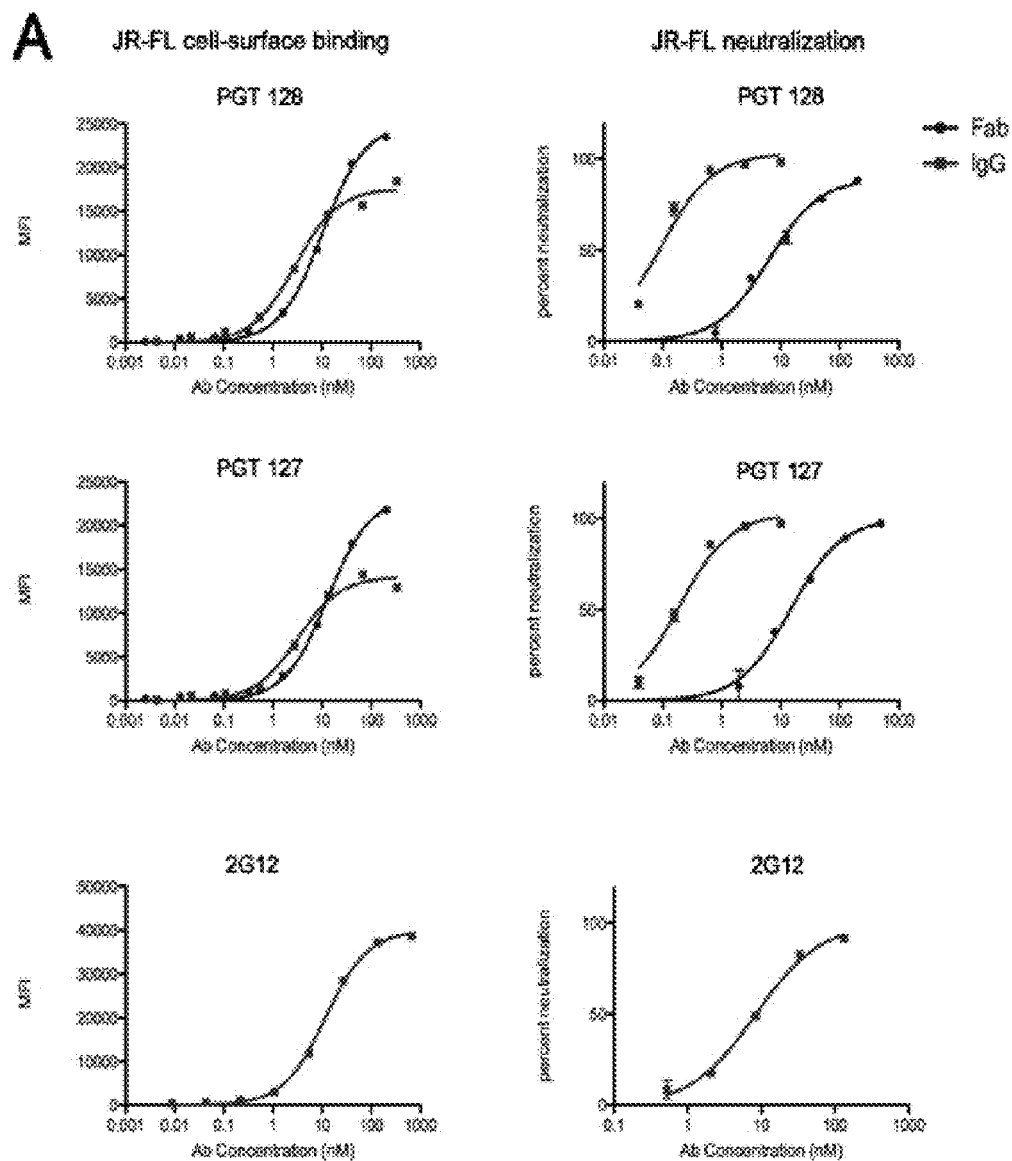
FIG. 5. Cell-surface binding and neutralization properties of PGT 127 and PGT 128 IgGs and Fabs. (A) (left) Binding of PGT 127 and PGT 128 Fabs and IgGs to HIV-1$_{JR-FL}$ trimers expressed on the surface of transfected 293T cells as determined by flow cytometry. (right) Neutralizing activity of PGT 127 and PGT 128 IgGs and Fabs against HIV-1$_{JR-FL}$. 2G12 is included for comparison. Experiments were performed in duplicate and data are representative of at least two independent experiments. MFI, mean fluorescence intensity. (B) (top) Comparison of binding (EC$_{50}$) and neutralization (IC$_{50}$) for PGT 127 and PGT 128 Fabs and IgGs against HIV-1$_{JR-FL}$. 2G12 is included for comparison. (bottom) Bar graph representation of Fab (IC$_{50}$): IgG (IC$_{50}$) ratios for PGT 127, PGT 128, b12, PG16, PGT 121, 2F5, and 4E10. Ratios were calculated as IC$_{50}$ of the Fab/IC$_{50}$ of IgG.
Figure 5B:
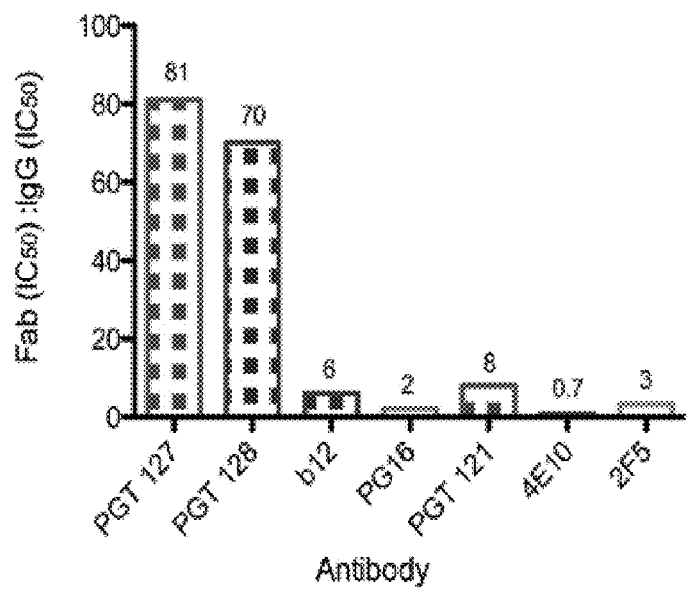
Figure 6A:
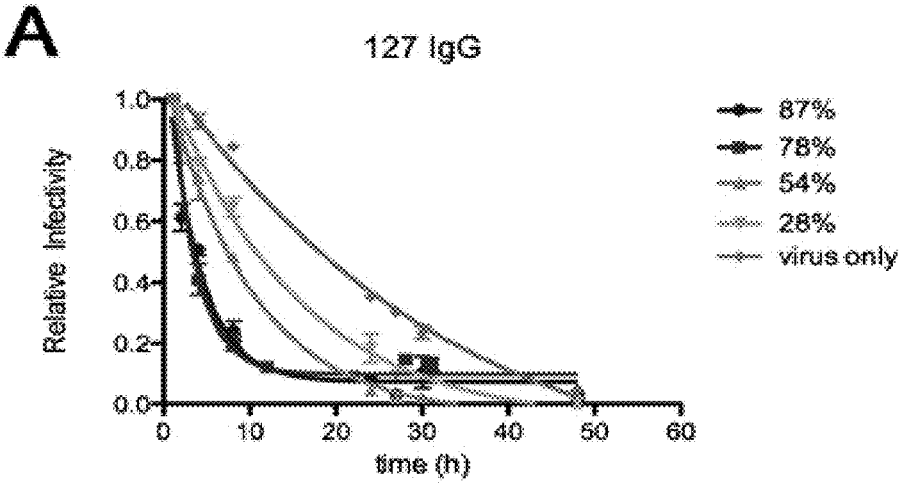
FIG. 6. Impact of PGT 127 and PGT 128 on viral infectivity decay. (A,B) Viral infectivity decay of HIV-1$_{JR-FL}$ was measured in the presence of PGT 127 and PGT 128 IgGs and Fabs. 2G12 is included for comparison. Data were fitted to a single-phase exponential decay to obtain half-life. Individual experiments were performed in triplicate, and error bars represent the standard error of two independent experiments. (C) The fold-reduction in the half-life of HIV-1$_{JR-FL}$ (expressed as an x-fold decrease) in the presence of antibodies at concentrations providing 90% neutralization, compared to the absence of antibody. Error bars represent the standard error of two independent experiments.
Figure 6A:
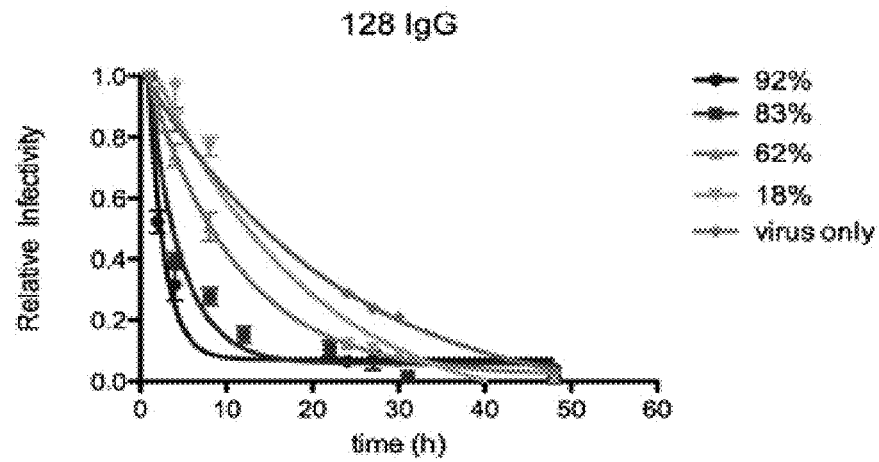
Figure 6A:
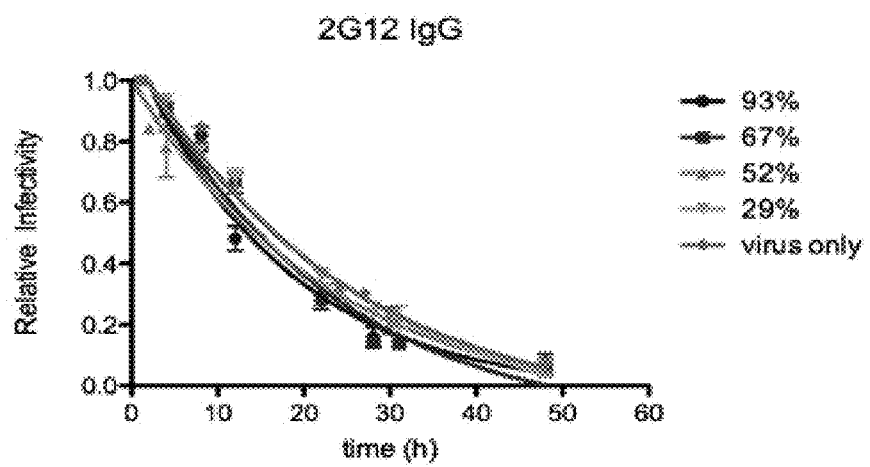
Figure 6B:
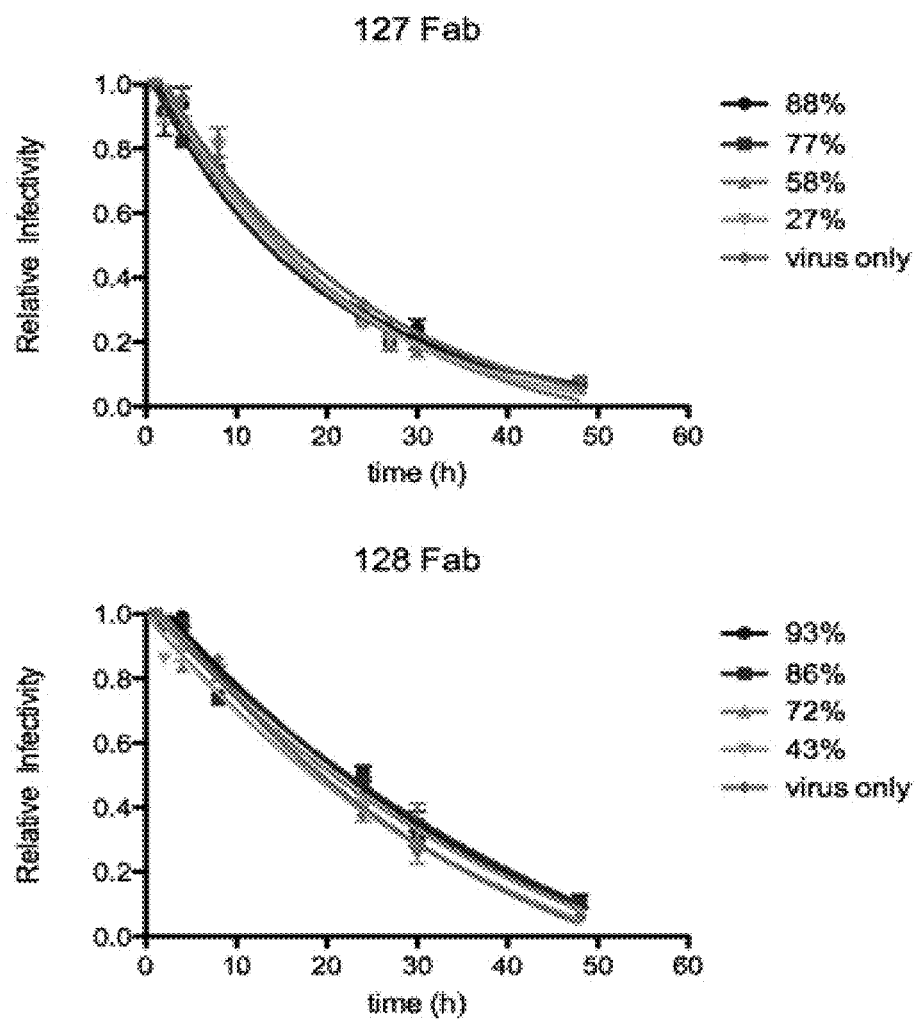
Figure 6C:
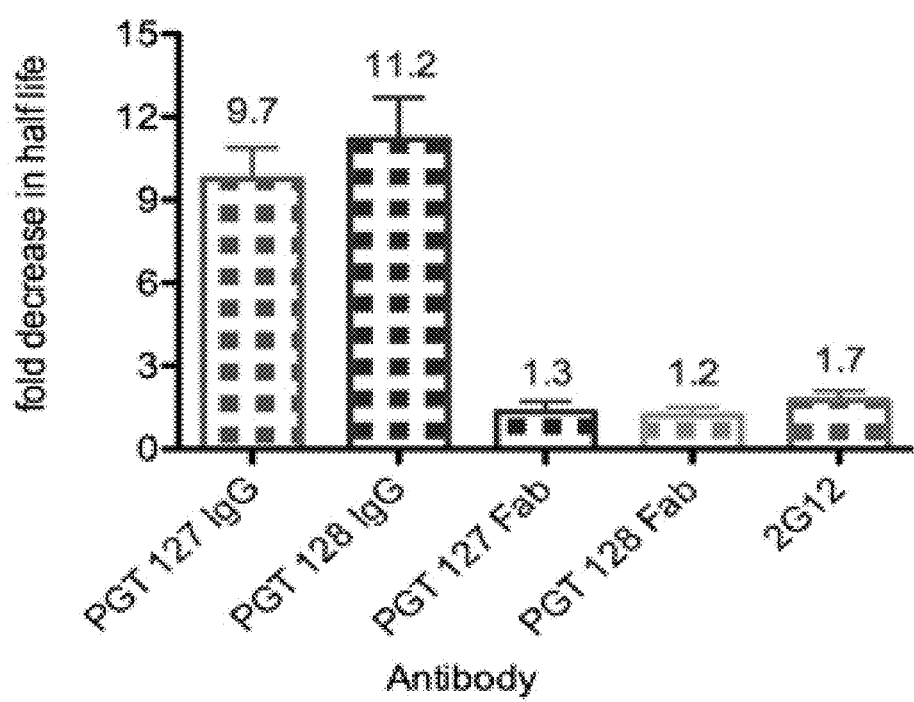
Figure 7A:
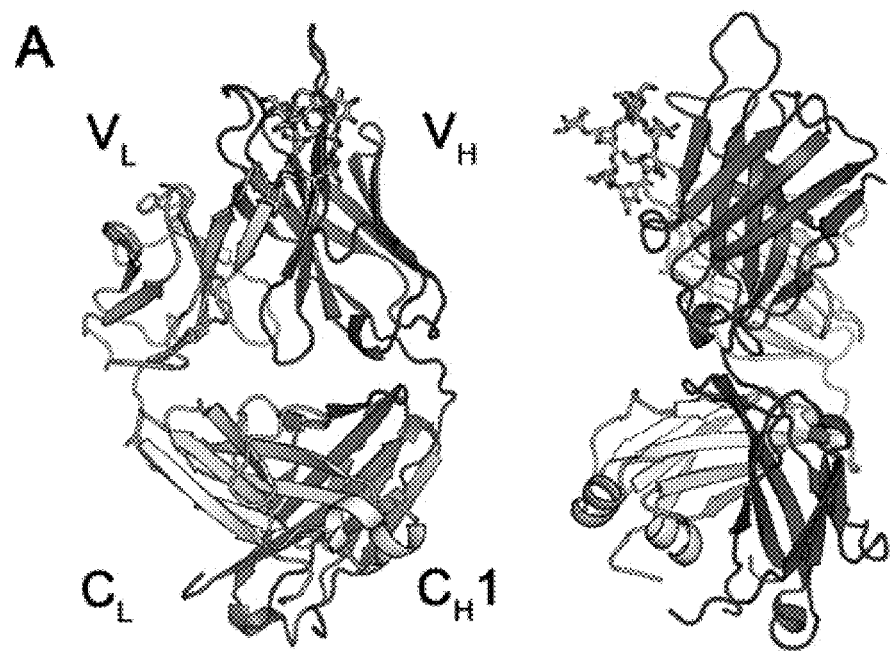
FIG. 7. Crystal structure of Man$_9$ complex with PGT 127 Fab. (A) Front (left) and side (right) views of PGT 127, shown as pink (heavy) and white (light) cartoon ribbons, bound to Man$_9$, depicted in ball and stick representation. (B) Glycan binding site of PGT 127 showing electron density (2Fo-Fc) at 1σ for glycan and select water molecules (red density) that bridge mannose residues. (C) Detailed view of Man$_9$ binding site of PGT 127. Hydrogen bonding interactions are shown in green dashes. (D) Superposition of PGT 127 and PGT 128 Man$_9$ complexes, depicted in ribbon representation, and bound glycan, shown as red (carbon) and black (oxygen) sticks. (E) Close up view of superposition of Man$_9$ binding sites of PGT 127 and PGT 128. The 6-residue H2 inserts adopt distinct conformations. The H2 insert in PGT 127 does not interact with Man$_9$, due to lattice contacts and, possibly, weaker association of Y52e and N53 relative to corresponding residues (W52e and N53) in PGT 128.
Figure 7B:
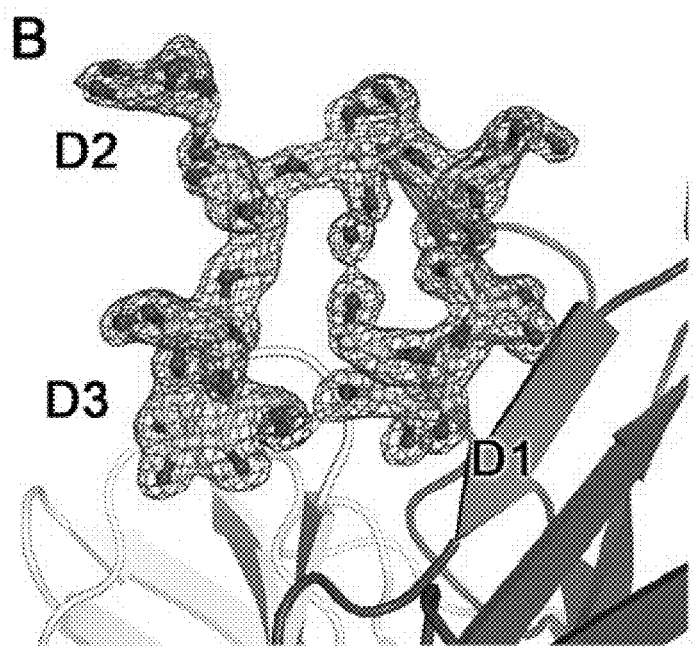
Figure 7C:
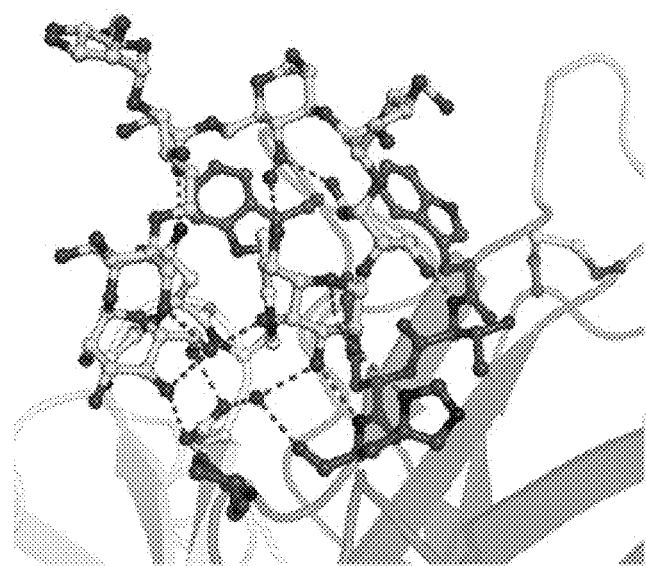
Figure 7D:
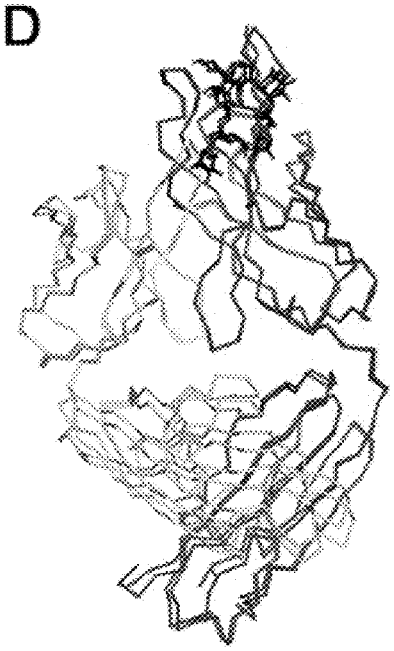
Figure 7E:
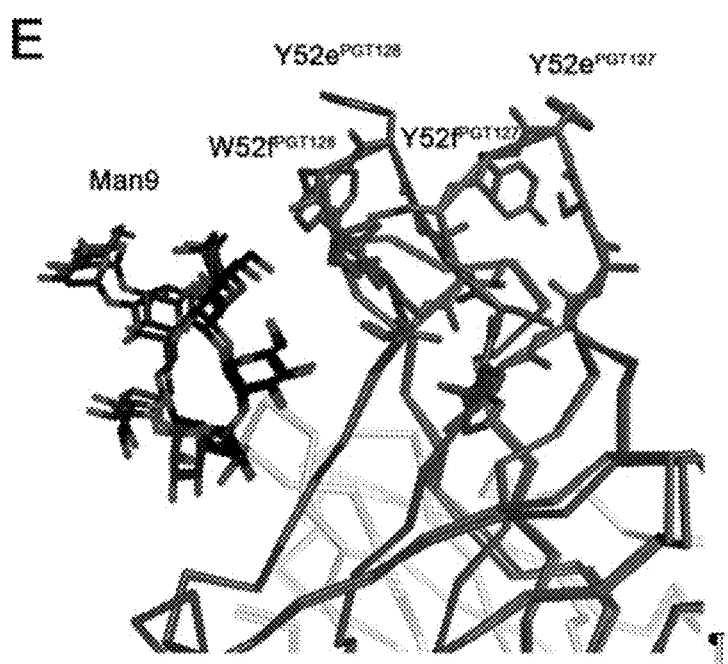
Figure 14:
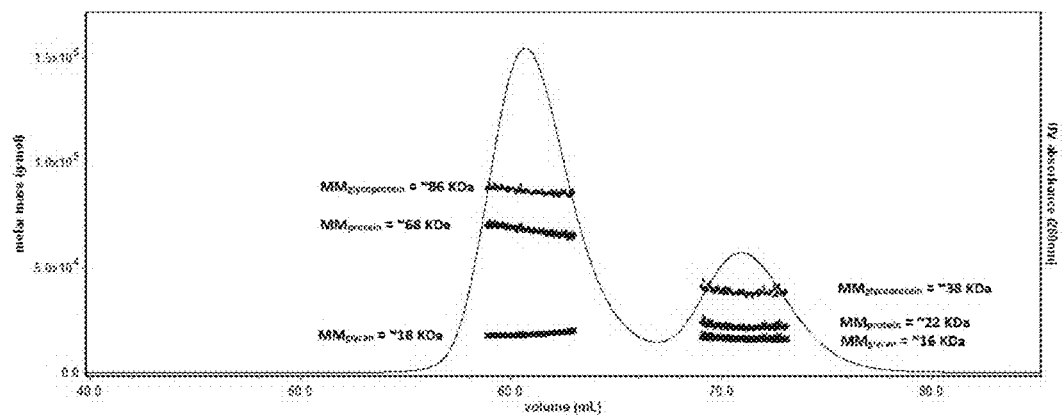
FIG. 14. SEC-UV/MALS/RI characterization of PGT 128 Fab in complex with eODmV3. The UV$_{280}$ absorbance trace is shown for the Superdex 200 16/60 elution profile of PGT 128 Fab in complex with eODmV3. Two major peaks were identified and further characterized by combining the measured UV$_{280}$ signal with MALS and RI online measurements. The calculated molar masses of the eluting glycoprotein, as well as the individual protein and carbohydrate molar mass contributions are represented as closely spaced blue dots forming a semi-connected line across the peak. The average molar masses determined by SEC-UV/MALS/RI are labeled and indicate that the first peak at 60.7 mL contains the PGT 128 Fab complex with eODmV3 (86 KDa total weight of glycoprotein=47 KDa for PGT 128 Fab+21 KDa for ODmV3 protein+18 KDa for eODmV3 glycan) whereas the second peak eluting at 71.0 mL is composed of unbound eODmV3, (38 KDa total weight of glycoprotein=22 KDa for eODmV3 protein+16 KDa for eODmV3 glycan). The theoretical molar masses of PGT 128 Fab (MM$_{protein}$=47,715.4 g/mol) and eODmV3 (MM$_{protein}$=21, 992.4 g/mol) are in agreement with those determined by SEC-UV/MALS/RI, and are within experimental error. Analysis of the glycan content of S27 the complex and eODmV3 (16-18±5 KDa) is consistent with utilization of the majority of the 12 predicted N-linked glycosylation. This SEC-UV/MALS/RI purification and characterization strategy allowed us to confidently assess the homogeneity of PGT 128 Fab/eODmV3 for crystallization studies.
Figure 19:
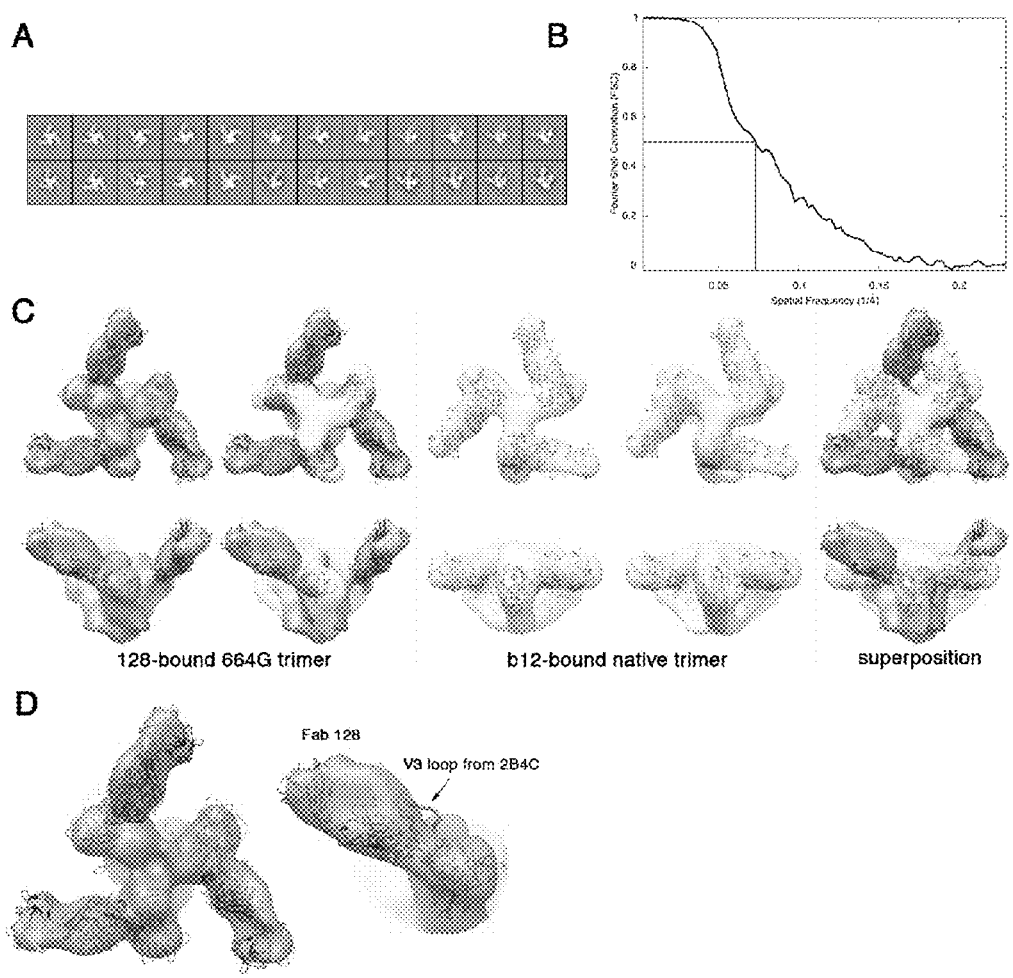
FIG. 19. Analysis of negative stain reconstruction of 664G trimer with PGT 128 Fab. (A) Comparison of reference free 2D class averages to reference projections: (top row) reference calculated from the d664G+PGT128 complex showing top to side view, (bottom row) reference free 2D class averages aligned to the respective reference shown in the top row. (B) The resolution of the reconstruction is 14.0 A, as determined from the Fourier shell correlation (FSC) plot. (C) Comparison of Fab PGT 128 and b12 complexes with Env trimers. The crystal structure of Fab PGT 128 in complex with eODmV3 fit to the negative stain S31 reconstruction (left). Superposed native, unliganded trimer cryoelectron tomographic reconstruction (30) (yellow) is shown for comparison (second image). Unliganded (yellow) and b12-liganded (green) native trimer (30) fit with b12-bound gp120 core (third and fourth images) (76). Superposed Fab PGT 128-liganded soluble 664G and native b12-liganded trimer densities fit with Fab PGT 128-bound eODmV3 and b12-bound gp120 core, respectively (right). (D) Localization of V3 in the Fab PGT 128-bound 664G trimer. (left) Top view of the 664G trimer with docked Fab PGT 128/eODmV3 structure (eODmV3, red; PGT 128 Fab white and blue) and CD4- and X5-bound HIV-1$_{JR\text{-}FL}$ gp120 core (PDB 2B4C; gp120, yellow; V3, magenta; CD4 and X5 Fab are not shown for clarity). The mini-V3 loop is shown as a thick magenta tube. (right) Side view showing that one side of the V3 loop from PDB 2B4C protrudes from the electron density, whereas the V3 loop tip encroaches into PGT 128 Fab density. However, the V3 loop is quite flexible and there is sufficient space to rotate its distal end closer to the central axis of the trimer, where the V1/V2 loops appear to be located.
Figure 20A:
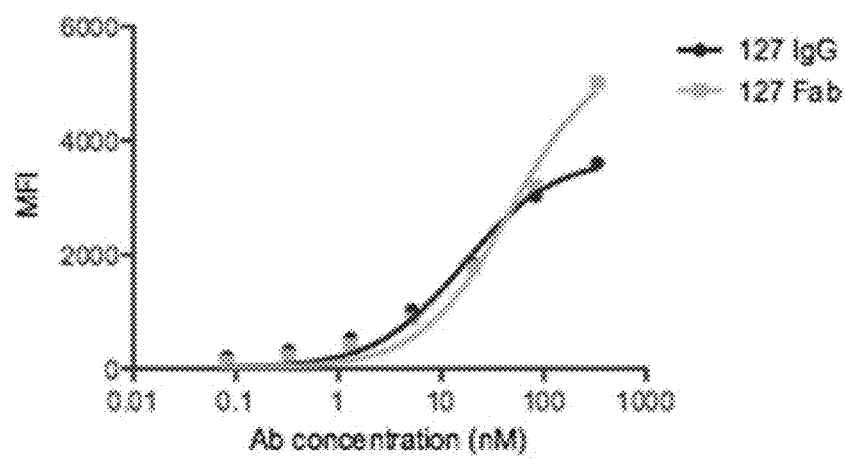
FIG. 20. Comparison of binding affinity of PGTs 127 and 128 IgGs and Fabs for cell surface trimers and neutralization potency. (A) Binding of PGT 127 and 128 IgGs (blue) and Fabs (cyan) to HIV-1$_{YU2}$ expressed on the surface of transfected 293T cells as determined by flow cytometry. (B) Neutralizing activity of PGT 127 and 128 IgGs (blue) and Fabs (cyan) against HIV-1$_{YU2}$.
Figure 20A:
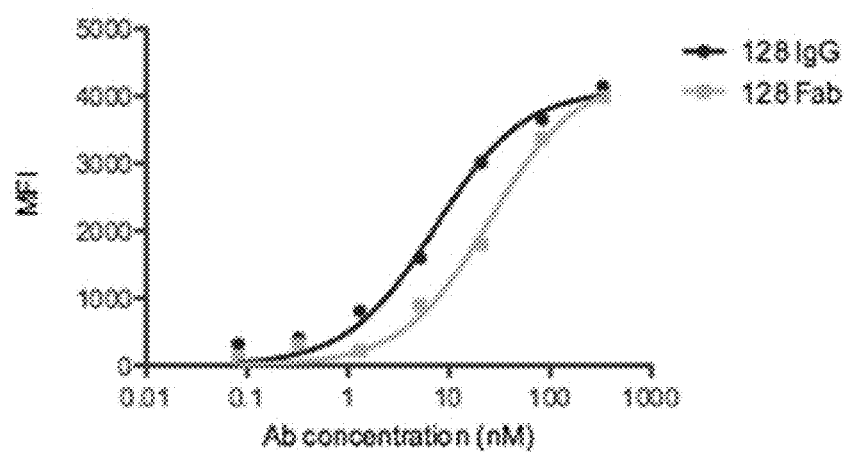
Figure 20B:
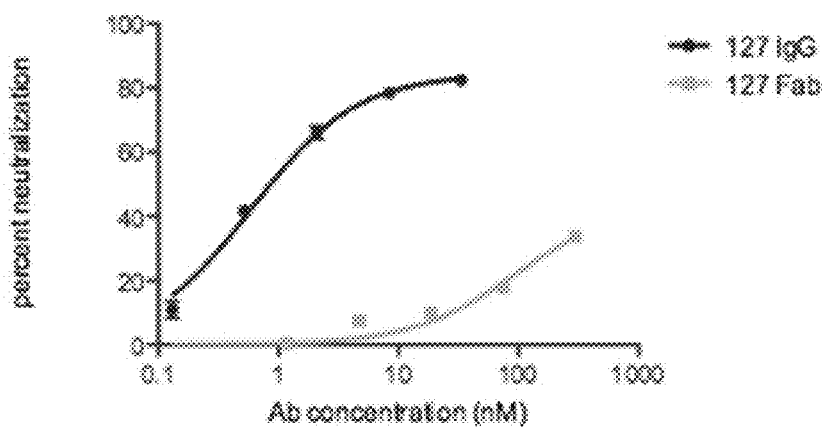
Figure 20B:
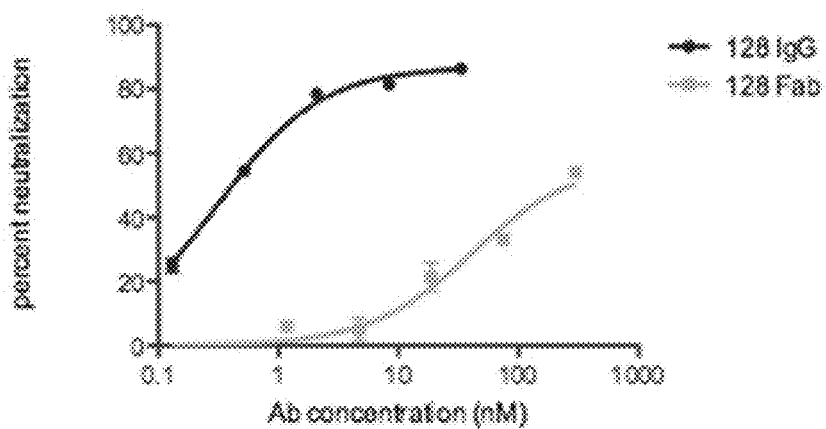
Figure 21:
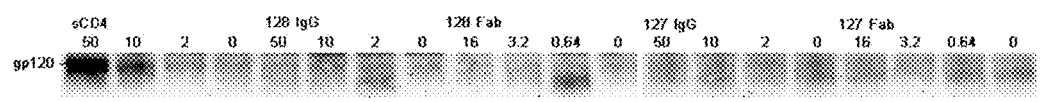
FIG. 21. Shedding of gp120 from HIV-1$_{JR\text{-}FL}$ transfected cells. Soluble CD4 (sCD4) and IgG and Fab PGT 127 and 128 (μg/ml quantities as indicated) were incubated with HIV-1$_{JR\text{-}FL}$ transfected cells, and the supernatants were analyzed by western blot. Only sCD4 shows evidence of gp120 shedding.

To gain a structural understanding of the epitope recognized by PGT 128 in the context of the HIV trimer, A negative stain reconstruction of a soluble, partially deglycosylated 664G trimer in complex with PGT 128 Fab was generated. This engineered Env trimer incorporates stabilizing mutations that allow it to maintain integrity upon deglycosylation (18-23). Three Fabs bind to the trimer with no close contacts to neighboring gp120 protomers, indicating that the outer domain epitope is accessible and highly exposed (FIG. 4A and FIG. 14). Fitting of the crystal structure of the PGT 128/eODmV3 complex into the reconstruction also revealed that the V3 base (FIG. 4B and FIG. 19D) is surface exposed, but below and adjacent to the density corresponding to the V1/V2 loops. No large-scale conformational changes in the trimer appear to take place upon Fab binding. Thus, the elements that form the PGT 128 epitope are almost directly opposite the CD4bs on gp120 and appear to be accessible and not subject to steric occlusion in the trimer.

Studies of protein-carbohydrate interactions have established various principles of molecular recognition. For example, because glycan-protein interactions are weak due to unfavorable entropy contributions associated with glycan binding, multivalency is crucial to enhance binding affinity. Here, Applicants provide an example of multivalency achieved through the combination of glycan and protein; the three sub-sites for N332, N301, and the C-terminal V3 stem are essentially independent, but combine to mediate high-affinity recognition of a glycan-based epitope on HIV Env. Considering the highly exposed nature of this epitope and the high conservation of its two glycan and V3 loop backbone components, coupled with recent studies demonstrating that broad and potent serum neutralizing activity is frequently mediated by antibodies that target N332A-sensitive epitopes (11, 40-43), it appears that this antigenic region may serve as a particularly attractive vaccine target if appropriate immunogens can be designed.

TABLE S1

X-ray diffraction data processing and structure refinement statistics.

| Crystal | PGT 128/eODmV3 | PGT 127/Man$_9$ | PGT 128/Man$_9$ |
|---|---|---|---|
| Space group | P2$_1$2$_1$2$_1$ | C2 | C222$_1$ |
| Unit cell constants (Å, °) | a = 50.79, b = 73.51, c = 241.45 α = β = γ = 90.00 | a = 103.55, b = 71.60, c = 78.83; β = 117.02 | a = 72.14, b = 106.02, c = 145.31; α = β = γ = 90.00 |
| Data processing statistics | | | |
| Beamline | SSRL 11-1 | APS GM/CA-CAT | SSRL 12-2 |
| Detector | MAR325 | MAR325 | PILATUS 6M |
| Program | HKL2000 | XDS | XDS |
| Resolution (Å) | 50-3.25 (3.37-3.25) | 25.0-1.65 (1.69-1.65) | 25.0-1.29 (1.33-1.29) |
| No. of observations | 54,241 (2,800) | 100,549 (7,449) | 907,457 (64,879) |
| No. of unique reflections | 13,365 (800) | 57,078 (4,316) | 139,361 (10,219) |
| Mosaicity (°) | 0.50 | 0.22 | 0.11 |
| Completeness | 91.7 (55.6) | 92.2 (94.9) | 99.9 (99.9) |
| Multiplicity | 4.1 (3.5) | 1.8 (1.7) | 6.5 (6.4) |
| I/σI | 6.6 (1.74) | 10.0 (2.22) | 13.1 (3.27) |
| R$_{sym}$ | 0.157 (0.55) | 0.055 (0.47) | 0.077 (0.55) |
| Refinement statistics | | | |
| $^+$Resolution (Å) | 50-3.25 (3.61-3.25) | 25.0-1.65 (1.68-1.65) | 25.0-1.29 (1.32-1.29) |
| $^+$Rcryst (%) | 0.207 (0.223) | 0.192 (0.237) | 0.159 (0.152) |
| $^+$R$_{free}$ (%) | 0.257 (0.272) | 0.215 (0.252) | 0.184 (0.177) |
| No. free reflections | 405 | 2810 | 1643 |
| Wilson B (Å$^2$) | 50.0 | 20.8 | 14.0 |
| Mean B-value (Å$^2$) | | | |
| Protein | 119.6 | 28.8 | 20.2 |
| V$_L$ and V$_H$ | 61.0 | 29.6 | 18.6 |
| C$_L$ and C$_H$1 | 152.5 | 27.7 | 22.3 |
| mini-V3 | 90.1 | n/a | n/a |
| Glycan | 74.3 | 37.3 | 25.8 |
| Water | n/a | 31.3 | 26.9 |
| RMSD bond lengths (Å) | 0.01 | 0.01 | 0.01 |
| RMSD and angles (°) | 1.22 | 1.26 | 1.27 |
| Ramachandran plot most favored (%) | 88.9 | 97.0 | 97.7 |

$^+$Statistics in highest resolution bin are in parentheses.

TABLE S2

Direct contacts and buried surface area between Fabs PGT 127 and PGT 128 and Man9.

Van der Waals contacts

| Man$_9$ glycan | Fab PGT 127 residue | Fab PGT 128 residue |
|---|---|---|
| Man$^3$ | Trp$^{L95}$, Trp$^{H100E}$ | Trp$^{L95}$, Trp$^{H100E}$ |
| Man$^4$ | | Asn$^{H53}$ |
| Man$^C$ | Trp$^{L95}$, Trp$^{H56}$, Thr$^{H57}$, Tyr$^{H58}$ | Trp$^{L95}$, Trp$^{H56}$, Thr$^{H57}$, Tyr$^{H58}$, |
| Man$^{D1}$ | Trp$^{L95}$, Thr$^{H57}$, Tyr$^{H58}$, His$^{H59}$, Lys$^{H64}$ | Trp$^{L95}$, Thr$^{H57}$, Tyr$^{H58}$, His$^{H59}$, Lys$^{H64}$ |
| Man$^4$ | | |
| Man$^{4'}$ | Asn$^{L94}$ | Asn$^{L94}$, Trp$^{L95}$ |
| Man$^B$ | Asn$^{L94}$ | Asn$^{L94}$ |
| Man$^{D3}$ | Gly$^{L93}$, Asn$^{L94}$, Trp$^{L95}$, Asp$^{L95A}$, Pro$^{H61}$ | Gly$^{L93}$, Asn$^{L94}$, Trp$^{L95}$, Asp$^{L95A}$, Pro$^{H61}$ |

Hydrogen bond contacts

| Man9 glycan | PGT 127 atom | Distance (Å) | PGT 128 atom | Distance (Å) |
|---|---|---|---|---|
| Man$^3$ | | | | |
| Man$^4$ | | | Trp$^{H52F}$-O | 3.03 |
| Man$^C$-O2 | Thr$^{H57}$-O | 3.32 | Thr$^{H57}$-O | 3.33 |
| Man$^C$-O3 | Thr$^{H57}$-O | 2.70 | Thr$^{H57}$-O | 2.74 |
| Man$^C$-O4 | Thr$^{H57}$-N | 3.17 | Thr$^{H57}$-N | 3.09 |
| Man$^{D1}$-O2 | His$^{H59}$-Nδ1 | 2.80 | His$^{H59}$-Nδ1 | 2.71 |
| Man$^{D1}$-O2 | Lys$^{H64}$-Nζ | 2.98 | Lys$^{H64}$-Nζ | 3.15 |
| Man$^{D1}$-O4 | Trp$^{L95}$-Nε1 | 2.92 | Trp$^{L95}$-Nε1 | 2.97 |
| Man$^{D1}$-O3 | His$^{H59}$-N | 2.94 | His$^{H59}$-N | 2.90 |
| Man$^{D1}$-O3 | | | His$^{H59}$-O | 3.38 |
| Man$^{D1}$-O5 | Lys$^{H64}$-Nζ | 3.17 | Lys$^{H64}$-Nζ | 3.01 |
| Man$^4$ | | | | |
| Man$^{4'}$-O5 | Asn$^{L94}$-Nδ2 | 3.18 | Asn$^{L94}$-Nδ2 | 3.03 |
| Man$^{4'}$-O6 | | | Asn$^{L94}$-Nδ2 | 3.20 |

TABLE S2-continued

Direct contacts and buried surface area between Fabs PGT 127 and PGT 128 and Man9.

| | | | | |
|---|---|---|---|---|
| Man$^{D3}$-O4 | Asp$^{L95A}$-Oδ2 | 2.63 | Asp$^{L95A}$-Oδ2 | 2.74 |
| Man$^{D3}$-O5 | Asn$^{L94}$-N | 3.39 | Asn$^{L94}$-N | 3.19 |
| Man$^{D3}$-O6 | Asp$^{L95A}$-Oδ1 | 2.80 | Asp$^{L95A}$-Oδ1 | 2.72 |
| Man$^{D3}$-O6 | Trp$^{L95}$-N | 3.03 | Trp$^{L95}$-N | 2.94 |
| Man$^{D3}$-O6 | Asn$^{L94}$-N | 3.05 | Asn$^{L94}$-N | 3.06 |

Buried surface area in the PGT 127 and PGT 128 combining sites

| Glycan residue | Buried SA (Å$^2$) | PGT 127 residue | Buried SA (Å$^2$) | Glycan residue | Buried SA (Å$^2$) | PGT 128 residue | Buried SA (Å$^2$) |
|---|---|---|---|---|---|---|---|
| Man$^3$ | 24.9 | Val$^{L92}$ | 5.7 | Man$^3$ | 33.5 | Val$^{L92}$ | 5.5 |
| Man$^4$ | 10.4 | Gly$^{L93}$ | 18.6 | Man$^4$ | 31.1 | Gly$^{L93}$ | 19.0 |
| Man$^C$ | 85.8 | Asn$^{L94}$ | 38.5 | Man$^C$ | 88.8 | Asn$^{L94}$ | 40.9 |
| Man$^{D1}$ | 96.2 | Trp$^{L95}$ | 60.7 | Man$^{D1}$ | 100.9 | Trp$^{L95}$ | 60.5 |
| Man$^A$ | 0.0 | Asp$^{L95A}$ | 25.3 | Man$^A$ | 0.0 | Asp$^{L95A}$ | 27.3 |
| Man$^{4'}$ | 28.7 | | | Man$^{4'}$ | 35.8 | Trp$^{H52F}$ | 28.3 |
| Man$^B$ | 11.6 | | | Man$^B$ | 10.6 | Asn$^{H53}$ | 19.5 |
| Man$^{D3}$ | 94.8 | | | Man$^{D3}$ | 93.2 | Arg$^{H54}$ | 0.8 |
| | | Asp$^{H55}$ | 7.02 | | | Gly$^{H55}$ | 6.9 |
| | | Trp$^{H56}$ | 31.1 | | | Trp$^{H56}$ | 29.3 |
| | | Thr$^{H57}$ | 32.3 | | | Thr$^{H57}$ | 32.2 |
| | | Tyr$^{H58}$ | 16.2 | | | Tyr$^{H58}$ | 15.2 |
| | | His$^{H59}$ | 33.9 | | | His$^{H59}$ | 36.4 |
| | | Pro$^{H61}$ | 19.3 | | | Pro$^{H61}$ | 20.4 |
| | | Lys$^{H64}$ | 25.3 | | | Lys$^{H64}$ | 26.3 |
| | | Asp$^{H100D}$ | 2.4 | | | Asp$^{H100D}$ | 3.9 |
| | | Trp$^{H100E}$ | 21.3 | | | Trp$^{H100E}$ | 24.1 |
| Total | 352.4 | | 337.6 | | 393.9 | | 396.5 |

Hydrogen bonds and van der Waals contacts were identified with CONTACSYM (77). Buried surface area was calculated with the Molecular Surface package (78).

TABLE S3

Summary of PGT 128 paratope mapping by site-directed mutagenesis.
Fold change in neutralization and gp120 binding are reported as
IC50 or EC50 of antibody variant/IC50 or EC50 of WT antibody.

| | | Fold change in gp120 binding | | | Fold change in neutralization | | |
|---|---|---|---|---|---|---|---|
| Chain | Variant | JR-CSF | JR-FL | BaL | JR-CSF | JR-FL | BaL |
| HC | D27A | 1.1 | 1.0 | 1.1 | 0.9 | n.d. | 1.6 |
| | S28A | 0.8 | 0.6 | n.d. | 1.2 | 0.9 | n.d. |
| | A30S | 0.8 | 0.7 | 0.6 | 0.9 | n.d. | 1.4 |
| | A30Q | 1.9 | 1.5 | n.d. | 2.4 | 11.4 | n.d. |
| | A31S | 0.8 | 1.1 | 0.9 | 1.1 | n.d. | 1.2 |
| | C32A | >150 | >200 | >150 | >2000 | >3000 | >4000 |
| | N33A | 0.5 | 0.6 | 0.8 | 0.7 | n.d. | 0.4 |
| | L51A | 0.7 | 0.7 | 1.5 | 1.2 | n.d. | 1.2 |
| | H52aA | 64 | 2.8 | 2.4 | 2.4 | 146 | 9.8 |
| | C52bA | >150 | >200 | >150 | >2000 | >3000 | >4000 |
| | Y52eA | 1.2 | 0.7 | 0.9 | 2.1 | 21.1 | 12.9 |
| | W52fA | 1.5 | 1.0 | 1.5 | 3.9 | 34.5 | 29.5 |
| | R54A | 0.9 | 0.5 | 0.6 | 0.6 | n.d. | 2.3 |
| | G55D | 0.7 | 1.4 | 2.5 | 2.0 | n.d. | 2.3 |
| | H59A | 1.0 | 0.8 | 1.0 | 6.8 | 12.4 | 11.5 |
| | K64A | 0.8 | 0.4 | n.d. | 1.2 | 1.3 | n.d. |
| | A70D | 0.5 | 1.0 | n.d. | 1.9 | n.d. | n.d. |
| | D72A | 0.9 | 0.7 | 0.7 | 1.0 | n.d. | 1.2 |
| | T73A | 1.6 | 2.2 | n.d. | 1.6 | 77.6 | n.d. |
| | P74A | 0.9 | 0.8 | n.d. | 0.8 | 1.2 | n.d. |
| | K75A | 2.1 | 1.6 | n.d. | 2.9 | 2.9 | n.d. |
| | F79A | 0.5 | 0.6 | n.d. | 0.9 | n.d. | n.d. |
| | L100A | 1.7 | n.d. | 1.3 | 0.8 | n.d. | 2.0 |
| | R100aA | 0.7 | 1.0 | 1.5 | 1.3 | n.d. | 2.1 |
| | T100cA | 1.2 | 0.9 | n.d. | 1.5 | 1.2 | n.d. |
| | D100dA | 0.1 | 0.1 | n.d. | 0.5 | 0.3 | n.d. |
| | W100eA | 17.4 | 9.4 | 15.0 | 29.7 | >3000 | 658 |
| | K100gA | >150 | 22.3 | 28.0 | 142 | >3000 | 1700 |
| | C32A C52bA | >150 | >200 | >150 | >2000 | >3000 | >4000 |

TABLE S3-continued

Summary of PGT 128 paratope mapping by site-directed mutagenesis.
Fold change in neutralization and gp120 binding are reported as
IC50 or EC50 of antibody variant/IC50 or EC50 of WT antibody.

| Chain | Variant | Fold change in gp120 binding | | | Fold change in neutralization | | |
|---|---|---|---|---|---|---|---|
| | | JR-CSF | JR-FL | BaL | JR-CSF | JR-FL | BaL |
| LC | N94A | 0.7 | 1.1 | n.d. | 3.5 | 1.3 | n.d. |
| | W95A | >150 | >200 | >150 | >2000 | >3000 | >4000 |
| | D95aA | >150 | >200 | >150 | 68.5 | >3000 | >4000 | n.d. = not determined.

TABLE S4

Direct contacts and buried surface area between Fab PGT 128 and eODmV3.

Van der Waals contacts

| eODmV3 | | Fab PGT 128 |
|---|---|---|
| Residue* | Region | Residue |
| $Arg^{304}$ | mini-V3 | $Leu^{H100}$ |
| $Ile^{323}$ | mini-V3 | $Leu^{H100}$, $Cys^{H32}$ |
| $Gly^{324}$ | mini-V3 | $Leu^{H100}$, $Arg^{H100A}$, $Tyr^{H100B}$ |
| $Asp^{325}$ | mini-V3 | $Trp^{H52F}$, $Tyr^{H100B}$, $Thr^{H100C}$, $Asp^{H100D}$ |
| $Ile^{326}$ | mini-V3 | $Arg^{H100A}$, $Tyr^{H100B}$, $Thr^{H100C}$ |
| $Arg^{327}$ | mini-V3 | $Tyr^{H52B}$, $Trp^{H52F}$, $Thr^{H100C}$, $Asp^{H100D}$ |
| $GlcNAc^1$ | N332 | $Tyr^{H52E}$ |
| $GlcNAc^2$ | N332 | $Tyr^{H52B}$, $Trp^{H52F}$ |
| $Man^3$ | N332 | $Trp^{L95}$ |
| $Man^{4'}$ | N332 | $Asn^{L94}$ |
| $Man^C$ | N332 | $Trp^{L95}$, $Trp^{H56}$, $Thr^{H57}$, $Tyr^{H58}$ |
| $Man^{D1}$ | N332 | $Trp^{L99}$, $Tyr^{H58}$, $His^{H59}$, $Lys^{H64}$ |
| $Man^{D3}$ | N332 | $Gly^{L93}$, $Asn^{L94}$, $Trp^{L95}$, $Asp^{L95A}$, $Pro^{H61}$ |
| $GlcNAc^1$ | N301 | $Cys^{H32}$, $Ala^{H52C}$ |
| $GlcNAc^2$ | N301 | $Ala^{H30}$, $His^{H52A}$, $Cys^{H52B}$ |
| $Man^3$ | N301 | $His^{H52A}$, $Thr^{H71}$, $Pro^{H74}$ |
| $Man^4$ | N301 | $His^{H52A}$, $Arg^{H54}$, $Thr^{H71}$ |
| $Man^{4'}$ | N301 | $Ala^{H30}$, $Thr^{H73}$, $Pro^{H74}$ |
| $Man^B$ | N301 | $Ser^{H28}$, $Pro^{H74}$ |

Hydrogen bond contacts

| eODmV3 | | Fab PGT 128 | | |
|---|---|---|---|---|
| Atom* | Region | Atom | Region | Distance (Å) |
| $Gly^{324}$-N | mini-V3 | $Leu^{H100}$-O | CDR H3 | 2.9 |
| $Gly^{324}$-O | mini-V3 | $Tyr^{H100B}$-N | CDR H3 | 3.1 |
| $Asp^{325}$-Oδ1 | mini-V3 | $Asp^{H100D}$-N | CDR H3 | 3.1 |
| $Asp^{325}$-Oδ2 | mini-V3 | $Asp^{H100D}$-N | CDR H3 | 3.3 |
| $Ile^{326}$-N | mini-V3 | $Tyr^{H100B}$-O | CDR H3 | 3.1 |
| $GlcNAc^1$-O3 | N332 | $Tyr^{H52E}$-OH | CDR H2 | 3.1 |
| $GlcNAc^2$-O6 | N332 | $Tyr^{H52E}$-OH | CDR H2 | 3.4 |
| $Man^{4'}$-O5 | N332 | $Asn^{L94}$-Nδ2 | CDR L3 | 3.4 |
| $Man^C$-O3 | N332 | $Thr^{H57}$-O | FR2 | 2.6 |
| $Man^C$-O4 | N332 | $Thr^{H57}$-O | FR2 | 3.1 |
| $Man^C$-O4 | N332 | $Thr^{H57}$-N | FR2 | 3.1 |
| $Man^{B1}$-O2 | N332 | $His^{H59}$-Nδ1 | FR2 | 2.6 |
| $Man^{B1}$-O2 | N332 | $Lys^{H64}$-Nζ | FR2 | 2.9 |
| $Man^{D1}$-O3 | N332 | $His^{H59}$-N | FR2 | 2.8 |
| $Man^{D1}$-O3 | N332 | $His^{H59}$-O | FR2 | 3.1 |
| $Man^{D3}$-O4 | N332 | $Asp^{L85A}$-Oδ1 | CDR L3 | 3.1 |
| $Man^{D3}$-O6 | N332 | $Asp^{L85A}$-Oδ2 | CDR L3 | 3.0 |
| $Man^{D3}$-O6 | N332 | $Trp^{L85}$-N | CDR L3 | 3.3 |
| $GlcNAc^1$-N2 | N301 | $Ala^{H52C}$-O | CDR H2 | 3.0 |
| $GlcNAc^1$-O3 | N301 | $Ala^{H52C}$-N | CDR H2 | 3.3 |
| $GlcNAc^2$-O7 | N301 | $Ala^{H30}$-O | CDR H1 | 2.7 |
| $Man^3$-O5 | N301 | $Thr^{H73}$-Oγ1 | FR3 | 3.1 |
| $Man^B$-O6 | N301 | $Pro^{H74}$-O | FR3 | 3.0 |

Buried surface area in the PGT 128 combining site

| eODmV3 residue* | Buried SA (Å²) | PGT 128 residue | Buried SA (Å²) |
|---|---|---|---|
| $Thr^{297}$ | 7.5 | $Val^{L92}$ | 8.9 |
| $Arg^{298}$ | 1.8 | $Gly^{L93}$ | 16.4 |
| $Asn^{300}$ | 17.3 | $Asn^{L94}$ | 41.7 |
| $Asn^{301}$ | 2.2 | $Trp^{L95}$ | 59.5 |
| $Arg^{304}$ | 20.0 | $Asp^{L95A}$ | 27.7 |
| $Ile^{322A}$ | 12.7 | $Asp^{H27}$ | 2.5 |
| $Ile^{323}$ | 42.1 | $Ser^{H28}$ | 20.0 |
| $Gly^{324}$ | 35.9 | $Ala^{H30}$ | 48.6 |
| $Asp^{325}$ | 53.8 | $Ala^{H31}$ | 4.1 |
| $Ile^{326}$ | 38.5 | $Cys^{H32}$ | 35.1 |
| $Arg^{327}$ | 66.1 | $His^{H52A}$ | 53.6 |
| $His^{330}$ | 6.7 | $Cys^{H52B}$ | 20.2 |
| $GlcNAc^{1(N332)}$ | 29.6 | $Ala^{H52C}$ | 31.2 |
| $GlcNAc^{2(N332)}$ | 37.6 | $Ser^{H52D}$ | 19.1 |
| $Man^{3(N332)}$ | 40.8 | $Tyr^{H52E}$ | 76.2 |
| $Man^{4(N332)}$ | 26.5 | $Trp^{H52F}$ | 78.0 |
| $Man^{4'(N332)}$ | 33.4 | $Asn^{H53}$ | 15.8 |
| $Man^{C(N332)}$ | 81.8 | $Arg^{H54}$ | 26.8 |
| $Man^{D1(N332)}$ | 101.1 | $Gly^{H55}$ | 5.8 |
| $Man^{B(N332)}$ | 11.1 | $Trp^{H56}$ | 28.4 |
| $Man^{D3(N332)}$ | 86.9 | $Thr^{H57}$ | 32.6 |
| $GlcNAc^{1(N301)}$ | 59.2 | $Tyr^{H58}$ | 16.7 |
| $GlcNAc^{2(N301)}$ | 72.1 | $His^{H59}$ | 38.3 |
| $Man^{3(N301)}$ | 44.0 | $Pro^{H61}$ | 20.6 |
| $Man^{4(N301)}$ | 56.8 | $Lys^{H64}$ | 22.4 |
| $Man^{4'(N301)}$ | 39.8 | $Leu^{H71}$ | 7.0 |
| $Man^{B(N301)}$ | 55.9 | $Thr^{H73}$ | 49.6 |
| | | $Pro^{H74}$ | 45.9 |
| | | $Lys^{H75}$ | 1.2 |
| | | $Asn^{H76}$ | 17.7 |
| | | $Glu^{H98}$ | 1.4 |
| | | $Leu^{H100}$ | 49.5 |
| | | $Arg^{H100A}$ | 32.8 |
| | | $Tyr^{H100B}$ | 55.0 |
| | | $Thr^{H100C}$ | 31.5 |
| | | $Asp^{H100D}$ | 32.8 |
| | | $Trp^{H100E}$ | 25.0 |
| Total | 1081.2 | | 1099.6 |

Hydrogen bonds and van der Waals contacts were identified with CONTACSYM (77). Buried surface area was calculated with the Molecular Surface package (78).
*The V3 base and loop residues are converted here to their standard (HxB2) nomenclature, but are designated by consecutive numbers (101-118) for the eODmV3 construct in the PDB coordinates.

TABLE S5

Sensitivity of PGTs 127 and 128 to removal of the glycans at positions N301 and N332 in different HIV-1 envelopes.

| | 127 | | 128 | |
|---|---|---|---|---|
| Strain | N301A | N332A | N301A | N332A |
| JRCSF | >250 | >200 | 10.7 | 1.4 |
| JRFL | >200 | >200 | >200 | >200 |

TABLE S5-continued

Sensitivity of PGTs 127 and 128 to removal of the glycans at positions N301 and N332 in different HIV-1 envelopes.

| Strain | 127 N301A | 127 N332A | 128 N301A | 128 N332A |
|---|---|---|---|---|
| 92RW020 | n.d. | 6.3 | n.d. | 1.6 |
| SF162 | >200 | >200 | >200 | >200 |
| BaL | >200 | >200 | >200 | >200 |
| ADA | >200 | >200 | >200 | >200 |

Values are presented as fold change in $IC_{50}$ of variant envelope compared to WT envelope (Fold change = $IC_{50}$ variant/$IC_{50}$ WT).
n.d. = not determined.

TABLE S6

Neoglycolipid probes included in the microarrays (N-glycan-related Array Set 1) with their binding signals (fluorescence intensities) for PGTs 127 and 128, 2G12 and plant lectin ConA.

| Position | Probe[a] | Sequence | 127 | 128 | 2G12 | ConA |
|---|---|---|---|---|---|---|
| 1 | Man2(α2)-DH | Manα-2Man-DH | — | — | 73 | — |
| 2 | Man2(α3)-DH | Manα-3Man-DH | — | 82 | 136 | — |
| 3 | Man2(α6)-DH | Manα-6Man-DH | — | — | 205 | 608 |
| 4 | Man3(α3,α6)-DH | Manα–6Man-DH<br>\|<br>Manα-3 | — | — | — | 759 |
| 5 | Man5(α3,α6)-DH | Manα-6<br>\|<br>Manα-3Manα–6<br>\|<br>Man-DH<br>\|<br>Manα-3 | — | — | 34 | 15,291 |
| 6 | Man1GN1-DH | Manβ-4GlcNAc-DH | — | — | 101 | — |
| 7 | Man2GN1-DH | Manα-3Manβ-4GlcNAc-DH | — | 16 | — | 575 |
| 8 | Man2aGN2-DH | Manα-6Manβ-4GlcNAcβ-4GlcNAc-DH | — | — | — | 1,923 |
| 9 | Man3aGN2-DH | Manα-6<br>\|<br>Manβ-4GlcNAcβ-4GlcNAc-DH<br>\|<br>Manα3 | — | — | 24 | 14,192 |
| 10 | Man3FGN2-DH | Manα-6   Fucα-6<br>\|    \|<br>Manβ-4GlcNAcβ-4GlcNAc-DH<br>\|<br>Manα3 | — | — | 52 | 20,011 |
| 11 | Man3XylGN2-DH | Manα-6<br>\|<br>Xylβ-2Manβ-4GlcNAcβ-4GlcNAc-DH<br>\|<br>Manα-3 | — | — | — | 977 |
| 12 | Man3FXylGN2-DH | Manα-6<br>\|<br>Xylβ-2Manα-4GlcNAcβ-4GlcNAc-DH<br>\|         \|<br>Manα-3     Fucα-3 | — | — | — | 3,932 |
| 13 | Man4aGN2-DH | Manα-3Manα-6<br>\|<br>Manβ-4GlcNAcβ-4GlcNAc-DH<br>\|<br>Manα-3 | — | 26 | — | 2,885 |
| 14 | Man4bGN2-DH | Manα-6<br>\|<br>Manα-3Manα-6<br>\|<br>Manβ-4GlcNAcβ-4GlcNAc-DH | — | — | — | 16,615 |

TABLE S6-continued

Neoglycolipid probes included in the microarrays (N-glycan-related Array Set 1) with their binding signals (fluorescence intensities) for PGTs 127 and 128, 2G12 and plant lectin ConA.

| Position | Probe[a] | Sequence | Fluorescence signal intensity[b] | | | |
|---|---|---|---|---|---|---|
| | | | 127 | 128 | 2G12 | ConA |
| 15 | Man5GN2-DH | Manα-6<br>\|<br>Manα-3Manα-6<br>\|<br>Manβ-4GlcNAcβ-4GlcNAc-DH<br>\|<br>Manα-3 | — | — | — | 16,390 |
| 16 | Man6GN2-DH | Manα-6<br>\|<br>Manα-3Manα-6<br>\|<br>Manβ-4GlcNAcβ-4GlcNAc-DH<br>\|<br>Manα-2Manα-3 | — | — | 49 | 19,006 |
| 17 | Man7(D1)GN2-DH | Manα-6<br>\|<br>Manα-3Manα-6<br>\|<br>Manβ-4GlcNAcβ-4GlcNAc-DH<br>\|<br>Manα-2Manα-2Manα-3 | — | 235 | 7,834 | 16,701 |
| 18 | Man7(D1)GN2-AO | Manα-6<br>\|<br>Manα-3Manα-6<br>\|<br>Manβ-4GlcNAcβ-4GlcNAc-AO<br>\|<br>Manα-2Manα-2Manα-3 | — | — | 15,667 | 15,893 |
| 19 | Glc2Man7(D1)GN1-AO | Manα-6<br>\|<br>Manα-3Manα-6<br>\|<br>Manβ-4GlcNAc-AO<br>\|<br>Glcα-3Glcα-3Manα-2Manα-2Manα-3 | — | — | — | 13,495 |
| 20 | Glc3Man7(D1)GN1-AO | Manα-6<br>\|<br>Manα-3Manα-6<br>\|<br>Manβ-4GlcNAc-AO<br>\|<br>Glcα-2Glcα-3Glcα-3Manα-2Manα-2Manα-3 | — | — | — | 16,532 |
| 21 | Man7(D3)GN2-DH | Manα-2Manα-6<br>\|<br>Manα-3Manα-6<br>\|<br>Manβ-4GlcNAcβ-4GlcNAc-DH<br>\|<br>Manα-2Manα-3 | 276 | 7,740 | — | 19,801 |
| 22 | Man8(D1D3)GN2-DH | Manα-2Manα-6<br>\|<br>Manα-3Manα-6<br>\|<br>Manβ-4GlcNAcβ-4GlcNAc-DH<br>\|<br>Manα-2Manα-2Manα-3 | 16,733 | 26,229 | 8,190 | 21,047 |
| 23 | Man9GN2-DH | Manα-2Manα-6<br>\|<br>Manα-2Manα-3Manα-6<br>\|<br>Manβ-4GlcNAcβ-4GlcNAc-DH<br>\|<br>Manα-2Manα-2Manα-3 | 24,209 | 26,071 | 11,717 | 21,359 |

TABLE S6-continued

Neoglycolipid probes included in the microarrays (N-glycan-related Array Set 1) with their binding signals (fluorescence intensities) for PGTs 127 and 128, 2G12 and plant lectin ConA.

| Position | Probe[a] | Sequence | Fluorescence signal intensity[b] | | | |
|---|---|---|---|---|---|---|
| | | | 127 | 128 | 2G12 | ConA |
| 24 | Man9GN2-AO | Manα-2Manα-6<br>             Manα-2Manα–3Manα-6<br>                             Manβ-4GlcNAcβ-4GlcNAc-AO<br>Manα-2Manα-2Manα-3 | 26,603 | 27,025 | 11,248 | 24,379 |
| 25 | Glc1Man9GN2-DH | Manα-2Manα-6<br>             Manα-6<br>Manα-2Manα-3<br>             Manβ-4GlcNAcβ-4GlcNAc-DH<br>Glcα-3Manα-2Manα-2Manα-3 | — | 1,042 | — | 23,414 |
| 26 | Glc1Man9GN2-AO | Manα-2Manα-6<br>             Manα-6<br>Manα-2Manα-3<br>             Manβ-4GlcNAcβ-4GlcNAc-AO<br>Glcα-3Manα-2Manα-2Manα-3 | — | 2,266 | — | 20,993 |
| 27 | Glc2Man9GN2-AO | Manα-2Manα-6<br>             Manα-6<br>Manα-2Manα-3<br>             Manβ-4GlcNAcβ-4GlcNAc-AO<br>Glcα-3Glcα-3Manα-2Manα-2Manα-3 | — | 4,140 | — | 20,647 |
| 28 | Glc3Man9GN2-AO | Manα-2Manα-6<br>             Manα-6<br>Manα-2Manα-3<br>             Manβ-4GlcNAc-AO<br>Glcα-2Glcα-3Glcα–3Manα-2Manα-2Manα-3 | 55 | 4,037 | NT | 23,004 |
| 29 | N1-DH | Galβ-4GlcNAcβ-2Manα-6    Fucα-6<br>                       Manβ-4GlcNAcβ-4GlcNAc-DH<br>             Manα-3 | — | — | 128 | 3,334 |
| 30 | N2-DH | Manα-6<br>         Manβ-4GlcNAcβ-4GlcNAc-DH<br>Galβ-4GlcNAcβ-2Manα-3 | — | — | — | 10,470 |
| 31 | N4-DH | Galβ-4GlcNAcβ-2Manα-6<br>                     Manβ-4GlcNAcβ-4GlcNAc-DH<br>             Manα-3 | — | — | — | 1,409 |
| 32 | N3-DH | GlcNAcβ-2Manα-6    Fucα-6<br>+Galβ-4            Manβ-4GlcNAcβ-4GlcNAc-DH<br>       GlcNAcβ-2Manα-3 | — | — | — | 7,874 |
| 33 | NGA2-DH | GlcNAcβ-2Manα-6<br>              Manβ-4GlcNAcβ-4GlcNAc-DH<br>GlcNAcβ-2Manα-3 | — | — | — | 2,139 |

TABLE S6-continued

Neoglycolipid probes included in the microarrays (N-glycan-related Array Set 1) with their binding signals (fluorescence intensities) for PGTs 127 and 128, 2G12 and plant lectin ConA.

| Position | Probe[a] | Sequence | Fluorescence signal intensity[b] | | | |
|---|---|---|---|---|---|---|
| | | | 127 | 128 | 2G12 | ConA |
| 34 | NGA2F-DH | GlcNAcβ-2Manα-6<br>              \|          Fucα-6<br>                            \|<br>              Manβ-4GlcNAcβ-4GlcNAc-DH<br>              \|<br>GlcNAcβ-2Manα-3 | — | — | — | 8,921 |
| 35 | NGA2B-DH | GlcNAcβ-2Manα-6<br>              \|<br>    GlcNAcβ-4Manβ-4GlcNAcβ-4GlcNAc-DH<br>              \|<br>GlcNAcβ-2Manα-3 | — | — | — | 5,258 |
| 36 | NGA3B-DH | GlcNAcβ-2Manα-6<br>              \|<br>    GlcNAcβ-4Manβ-4GlcNAcβ-4GlcNAc-DH<br>              \|<br>GlcNAcβ-4Manα-3<br>      \|<br>GlcNAcβ-2 | — | — | — | — |
| 37 | NGA4-DH | GlcNAcβ-6<br>    \|<br>GlcNAcβ-2Manα-6<br>              \|<br>            Manβ-4GlcNAcβ-4GlcNAc-DH<br>            \|<br>GlcNAcβ-2Manα-3<br>    \|<br>GlcNAcβ-2 | — | — | — | 290 |
| 38 | NGA5B-DH | GlcNAcβ-6<br>    \|<br>GlcNAcβ-2Manα-6<br>GlcNAcβ-4    \|<br>        GlcNAcβ–4Manβ-4GlcNAcβ-4GlcNAc-DH<br>GlcNAcβ-4Manα-3<br>    \|<br>GlcNAcβ-2 | — | — | 58 | — |
| 39 | GNMan5BGN2-DH | Manα-6<br>  \|<br>Manα-3Manα-6<br>           \|<br>    GlcNAcβ-4Manβ-4GlcNAcβ-4GlcNAc-DH<br>           \|<br>GlcNAcβ-2Manα-3 | — | — | — | 13,768 |
| 40 | NA2-DH | Galβ-4GlcNAcβ-2Manα-6<br>                    \|<br>              Manβ-4GlcNAcβ-4GlcNAc-DH<br>                    \|<br>Galβ-4GlcNAcβ-2Manα-3 | — | — | — | 4,353 |
| 41 | NA2F-DH | Galβ-4GlcNAcβ-2Manα-6      Fucα-6<br>                    \|         \|<br>              Manβ-4GlcNAcβ-4GlcNAc-DH<br>                    \|<br>Galβ-4GlcNAcβ-2Manα-3 | — | — | — | 2,405 |
| 42 | NA2F-AO | Galβ-4GlcNAcβ-2Manα-6      Fucα-6<br>                    \|         \|<br>              Manβ-4GlcNAcβ-4GlcNAc-AO<br>                    \|<br>Galβ-4GlcNAcβ-2Manα-3 | — | — | — | 3,121 |

TABLE S6-continued

Neoglycolipid probes included in the microarrays (N-glycan-related Array Set 1) with their binding signals (fluorescence intensities) for PGTs 127 and 128, 2G12 and plant lectin ConA.

| Position | Probe[a] | Sequence | Fluorescence signal intensity[b] | | | |
|---|---|---|---|---|---|---|
| | | | 127 | 128 | 2G12 | ConA |
| 43 | NA2FB-DH | Galβ-4GlcNAcβ-2Manα-6<br>　　　　　Fucα-6<br>GlcNAcβ-4Manβ-4GlcNAcβ-4GlcNAc-DH<br>Galβ-4GlcNAcβ-2Manα-3 | — | — | — | — |
| 44 | NA3-Le[c]-DH | Galβ-4GlcNAcβ-2Manα-6<br>+Fucα-3　Manβ-4GlcNAcβ-4GlcNAc-DH<br>Galβ-4GlcNAcβ-2Manα-3<br>Galβ-4GlcNAcβ-2 | — | — | — | — |
| 45 | NA4-DH | Galβ-4GlcNAcβ-6<br>Galβ-4GlcNAcβ-2Manα-6<br>　Manβ-4GlcNAcβ-4GlcNAc-DH<br>Galβ-4GlcNAcβ-2Manα-3<br>Galβ-4GlcNAcβ-2 | — | — | — | — |
| 46 | A2F(2-3)-DH | NeuAcα-3Galβ-4GlcNAcβ-2Manα-6　Fuc-6<br>Manβ-4GlcNAcβ-4GlcNAc-DH<br>NeuAcα-3Galβ-4GlcNAcβ-2Manα-2 | — | — | — | 782 |
| 47 | A2(2-6)-DH | NeuAcα-6Galβ-4GlcNAcβ-2Manα-6<br>Manβ-4GlcNAcβ-4GlcNAc-DH<br>NeuAcα-6Galβ-4GlcNAcβ-2Manα-2 | — | — | — | 670 |
| 48 | (6P)Man5GN2-AO | P6-Manα-6<br>Manα-6<br>Manα-3　Manβ-4GlcNAcβ-4GlcNAc-AO<br>Manα-3 | — | — | NT | 3,369 |
| 49 | (6P)Man6GN2-AO | P6-Manα-6<br>Manα-6<br>Manα-3　Manβ-4GlcNAcβ-4GlcNAc-AO<br>Manα-2Manα-3 | — | — | NT | 16,736 |
| 50 | Dextran-6-AO | Glcα-6Glcα-6Glcα-6Glcα-6Glcα-6Glc-AO | — | — | — | 1,138 |

[a]The oligosaccharide probes are all lipid-linked, and are from the collection assembled in the course of research in Glycosciences Laboratory.
DH, designates neoglycolipids (NGLs) prepared from reducing oligosaccharides by reductive amination with the amino lipid, 1,2-dihexadecyl-sn-glycero-3-phosphoethanolamine (DHPE) (69); AO, designates NGLs prepared from reducing oligosaccharides by oxime ligation with an aminooxy-functionalized DHPE (70). Whereas DH-NGLs have fully ring-opened monosaccharide cores, a significant proportion of monosaccharide cores of AO-NGLs are in ring-closed form (70).
[b]—Signal less than 1.
[c]2G12 was tested in a different version of the microarray.
NT, not tested.

Example 2: Materials and Methods

Antibodies and Antigens.

The following antibodies and reagents were procured by the International AIDS Vaccine Initiative (IAVI) Neutralizing Antibody Consortium: antibody 2G12 (Polymun Scientific), antibody F425/b4E8 (provided by L. Cavacini, Beth Israel Deaconess Medical Center), and soluble CD4 (Progenics).

Expression and Purification of PGT 127 and 128 Fabs and eODmV3.

Recombinant Fabs 127 and 128 were produced in Free-Style™ 293F (Invitrogen) suspension cultures by transfection of plasmids containing expression constructs for light chain and heavy chain terminating at Asp$^{H234}$. Fabs were purified by anti-human lambda affinity chromatography and cation exchange as previously described (44). Fab fractions were pooled and purified further by size exclusion chromatography (SEC) using Superdex 200™ (GE Healthcare) in 20 mM Tris pH 8.0, 150 mM NaCl. The Fab peak was pooled and concentrated to 56 mg/ml in SEC buffer.

A recombinant engineered outer domain containing a truncated JR-FL V3 loop, "mini-V3", termed eODmV3, was expressed in HEK 293S GnTI$^{-/-}$ cells (45). Plasmid pHLsec containing eODmV3 was transfected using the linear 25 kDa polyethyleneimine (PEI) under serum free conditions. Following transfection, cells were allowed to secrete eODmV3 for 72 hours. Culture supernatant was concentrated to 0.5 L using a tangential flow apparatus and 10 kDa ultrafiltration membrane. Concentrated supernatant was loaded onto *Galanthus nivalis* lectin beads at a flow-rate of 1 ml/ml, washed with Dulbecco's phosphate buffered saline (DPBS) pH 7.2, washed again with DPBS+0.5M NaCl, and eluted with DPBS+1M methyl-α-D-mannopyranoside. Eluted eODmV3 was concentrated and further purified by SEC on Superdex 200 16/60 (GE Healthcare).

PGT 128 IgG antibody variants were produced in FreeStyle™ 293F (Invitrogen) suspension cultures by transfection of plasmids containing expression constructs for light chain and heavy chain and pAdVAntage™ Vector (Promega) using 293Fectin (Invitrogen). Supernatants were harvested 96 hours after transfection. Antibodies were purified using ProteinA Sepharose™ (GE Healthcare) or used without purification with concentration determined by ELISA.

KNH1144 SOSIP 664G Production.

$5.6 \times 10^6$ 293 S cells were seeded in Hyperflasks (Corning Life Sciences) and incubated for 72 hrs until confluent in Dulbecco's modified Eagle's medium supplemented with 10% calf serum (Invitrogen), 100 mM Sodium Pyruvate (Invitrogen), GlutaMAX supplement (Invitrogen), Penicillin/Streptomycin (Invitrogen) and 10 mM non-essential amino acids solution (Invitrogen). KNH1144 SOSIP 664G (Depetris et al. manuscript in preparation) protein was produced by cotransfection of the adherent 293S cells with pPI4 KNH1144 SOSIP 664G and pcDNA3.1 Furin using PEI Max (Polysciences), followed by 32° C. incubation for 48 hrs. The harvested supernatant was passed through 0.22 μm filter before storing at 4° C. for subsequent purification steps.

Affinity Purification of KNH1144 SOSIP 664G.

Transfection supernatants were passed (0.5-1 ml/min flow rate) through CNBr-activated Sepharose 4B (GE Healthcare) beads coupled with broadly neutralizing antibody 2G12 (Polymun Sciences). The beads were washed with 15-20 column volumes of wash buffer (500 mM Nacl, 10 mM Tris, pH 8.0) before eluting the envelope trimers with 3-5 column volumes of 3M MgCl$_2$ (elution buffer). The eluted trimers were immediately buffer exchanged into 75 mM NaCl, 10 mM Tris, pH 8.0 using Vivaspin ultrafilters (100 kDa MWCO).

Preparation of 128 Fab Complex with Fully-Glycosylated Gp120 Outer Domain.

The first half of the monomer eODmV3 SEC peak was pooled and a sub-stoichiometric quantity PGT 128 Fab was added, allowing PGT 128 to select the heavier MW glycoform with intact Man$_{8/9}$ sugars. This complex was again passed over Superdex 200 to remove unbound, underglycosylated, eODmV3. The complex peak was concentrated to 15 mg/ml in SEC buffer.

Determination of Absolute Molar Mass and Carbohydrate Composition of eODmV3 in Complex with Fab 128 by SEC-UV/MALS/RI.

Approximately 5 mg of PGT 128 Fab+eODmV3 complex was separated on a Superdex 200 16/60 column (GE Healthcare) using an AKTA Avant FPLC system (GE Healthcare). Size exclusion chromatography (SEC) was coupled in-line with the following calibrated detectors: a HP1 1050 Hewlett-Packard UV detector (Norwalk), a MiniDawn Treos multi-angle light scattering (MALS) detector (Wyatt Corporation), and an Optilab T-reX refractive index (RI) detector (Wyatt Corporation). These combined measurements allow for the determination of the absolute molar mass of an eluting glycoprotein, as well as the individual contribution from protein and carbohydrate components to the total molar mass, as previously described. The Astra V software (Wyatt Corporation) was used for this analysis by applying the protein conjugate template to the measured data. The extinction coefficient of the PGT 128 Fab and eODmV3 polypeptides, $A^{0.1\%}{}_{280}$ were determined to be 2014 mL*mg$^{-1}$ cm$^{-1}$ and 841 mL*mg$^{-1}$ cm$^{-1}$ from their primary amino acid sequence, respectively (http://web.expasy.org/protparam). To derive the molar mass, the following pre-established refractive index increment values were used: $(dn/dc)_{protein}=0.185$ mL/g and $(dn/dc)_{carbohydrate}=0.140$. Uncertainty in the reported molar masses of the glycoprotein components range between 1% to 30%, and is attributed to: 1% error in the dn/dc value of the glycoprotein will propagate as a corresponding ±1% error in the calculated molar mass (46), as much as 10% error due instability of the system (46), and errors propagated in the calculations performed by Astra V range between 1% to 14%.

Preparation of PGT 128 Fab Complex with Partially Deglycosylated 664G Trimer.

664G trimer was combined with excess PGT 128 Fab and allowed to incubate on ice 1 hour. 1M sodium acetate was added to a final concentration of 100 mM and Endo H (Roche) was added. Deglycosylation was allowed to proceed for 3 hrs at 37° C. The partially-deglycosylated complex was then loaded separated from Endo H, free Fab, and released glycans by Superdex 200 16/60.

Crystallization of 127 and 128 Fab Complexes with Man$_9$.

A synthetic glycan consisting of Man$_9$ linked to an amino group via five methylene carbons (47), Man$_9$ (MW 1562 Da), was dissolved in water to a concentration of 20 mM. Fabs of PGT 127 and 128 were mixed with Man$_9$ to give a final concentration of 18.5 mg/ml Fab and 6.5 mM glycan. Crystals of 127/Man$_9$ were grown in 14% PEG 4000, 0.1M HEPES pH 7.5, 8.5% isopropanol, and 15% glycerol. Crystals of PGT 128/Man$_9$ were grown in 11% PEG 4000, 0.1M HEPES pH 7.5, and 10% isopropanol at 4° C. 127/Man$_9$ crystals were cryoprotected by transferring into a solution consisting of 14% PEG 4000, 0.1M HEPES pH 7.5, 10% isopropanol, 20% glycerol, and 6.5 mM Man$_9$. 128/Man$_9$ crystals were cryoprotected by transferring into a solution consisting of 14% PEG 4000, 0.1M HEPES pH 7.5, 10% isopropanol, 20% glycerol, and 6.5 mM Man$_9$. Crystals were then looped using Hampton Research mounting loops and frozen by plunging into liquid nitrogen.

Crystallization of 128 Fab Complex with Glycosylated eODmV3.

Co-crystals of Fab 128 with glycosylated eODmV3 were grown by mixing the concentrated complex (15 mg/ml) 1:1 with 24% PEG 3350 and 0.29M CaCl$_2$. Crystals were cryoprotected by transferring to a solution of 16% PEG 3350, 0.1M Tris pH 8.0, 0.2M CaCl$_2$, and 30% glycerol.

Structure Solution and Refinement.

Crystals of 128/Man$_9$ complex diffracted to 1.29 Å resolution. Diffraction data were collected at SSRL 12-2 using a PILATUS detector (Detectris) and were indexed in space group C222$_1$. The PGT 128/Man$_9$ structure was solved by molecular replacement using the program Phaser (48) in the CCP4 suite (49). The constant chains were placed first, followed by variable light chain from PDB entry 3MUG (44) and the variable heavy domain from PDB entry 2JE6 (50). The structure was refined with phenix.refine (51), by iterative rounds of refinement using rigid body, simulated annealing torsional and cartesian dynamics, coordinate minimization, and anisotropic B-factor refinement. Manual model rebuilding and water placement between rounds of automated refinement with phenix.refine was performed with Coot (52). In the final round, riding hydrogens were added to Fab atoms to improve geometry and minimize steric clashes. The structure of PGT 128/Man$_9$ was refined to a resolution of 1.29 Å with final crystallographic $R_{cryst}/R_{free}$ of 0.159/0.184.

Crystals of 127/Man$_9$ complex diffracted to 1.65 Å resolution. Diffraction data were collected at GM/CA-CAT using a MAR325 detector (Rayonix) and were indexed in space group C2. The PGT 127/Man$_9$ structure was solved using the coordinates of Fab 128 but with the H2 insertion removed. The H2 insert was rebuilt with Coot, the glycan residues were modeled, and the structure was refined with phenix.refine using identical methods, although individual atomic B-factors were refined isotropically, with phenix.refine to a resolution of 1.65 Å with final crystallographic $R_{cryst}/R_{free}$ of 0.195/0.215.

Crystals of the 128/eODmV3 complex diffract to 3.25 Å resolution. Difraction data were collected at SSRL 11-1 using a MAR325 detector (Rayonix) and were indexed in space group P2$_1$2$_1$2$_1$. The structure was solved by molecular replacement with Phaser, using the coordinates of Fab PGT 128. The elbow angle was varied and the best solution, which has a slightly different elbow angle than in the complex with Man$_9$, was refined by rigid body minimization. The outer domain was placed manually by examination of the difference density, in which helix α2 and adjoining β strands were visible. The outer domain was then positioned by rigid body refinement. A 2.8 Å resolution structure was available for the engineered outer domain lacking mini-V3 (Huang et al. manuscript in preparation) and used as the starting model in the complex. Glycans were built using high-resolution coordinates (N332) as a starting model or de novo (N301) using Coot. The mini-V3 was modeled in Coot. The eODmV3 structure was refined with Buster 2.10 (53) by individual, isotropic correlated B-factor adjustment, TLS, and coordinate minimization. Final crystallographic $R_{cryst}/R_{free}$ of 0.207/0.257 were obtained.

Although Applicants report the structure to a final resolution of 3.25 Å, anisotropic ellipsoidal cutoffs (54) of 3.0 Å (a), 3.3 Å (b), and 3.6 (c) were performed using an in-house script and Scalepack (55) to remove the weakest, most poorly measured data (54). B-factor sharpening (56) was used to improve the maps for manual building in Coot.

Electron Microscopy.

Negative stained grids were prepared by applying 0.1 mg/ml of the purified d664G/PGT128 complex to a freshly glow discharged carbon coated 400 Cu mesh grid and stained with 2% uranyl formate. Grids were viewed using a FEI Tecnai TF20 electron operating at a magnification of 100,000× and a high tension of 120 kV. Images were acquired on a Gatan 4 k×4 k CCD camera at 0 and 45° tilt angles using a defocus range of 700 to 900 nm. The 45° tilt angle provided additional particle orientations to improve the image reconstruction. The pixel size of the CCD camera was calibrated at this magnification to be 1.09 Å using a 2D catalase crystal with known cell parameters. A total of 4980 particles were used for the final image reconstruction, and a conservative resolution of 18.3 Å was estimated using an FSC of 0.5.

Image Processing.

Particles were automatically selected from micrographs using the DoG Picker software through the Appion package (57, 58). The contrast transfer function estimation for untilted micrographs were completed using ctffind3 and applied using ACE2 (57, 59). Particles were binned by 4 (80×80 sized boxes) and reference free 2D class averages were produced using the Sparx package (60). An ab initio 3D image reconstruction was generated using these class averages with the EMAN2 package (61). The final 3D image reconstruction, using 3-fold symmetry, was determined using EMAN (62).

Fitting of PGT 128/eODmV3 Coordinates into Trimer Density.

The gp120/Fab PGT 128 complex structure was divided into two rigid bodies. One rigid body consisted of gp120 and the variable region of Fab PGT 128 and the other rigid body consisted of the constant region of Fab PGT 128. The gp120 and Fab PGT 128 variable region rigid body was manually fit into the negative stained image reconstruction and refined using the Fit command of UCSF Chimera. The crystal structure of the entire gp120/Fab PGT 128 complex was then overlaid onto the fitted structure to identify the location of the constant region of Fab PGT 128. The constant region of Fab PGT 128 was then manually fit into the image reconstruction using the Fit in Map function of Chimera with the Real-time S12 correlation/average update function enabled, as the elbow angle between the variable and constant regions can vary under different conditions even for the same Fab, as Applicants noted in the PGT 128 crystal structures. This combination allowed us to minimize the movement of the constant region with respect to the variable region, to reduce atom clashes between the two rigid bodies, while concurrently maximizing the correlation coefficient between the atomic structure and the image reconstruction. The Find Clashes/Contacts function in Chimera was used to identify the number of atomic clashes as a result of VDW overlap >=0.4 A. There are no clashes in the fitted structures.

Antibody and Envelope Mutations.

Mutations in the 128 heavy and light chains and the HIV envelope were made using QuikChange site-directed mutagenesis (Stratagene). Mutations were verified by DNA sequencing.

Gp120, C3, and RNAseB ELISA.

Native Human C3 and goat-anti-Human-C3 were obtained from AbD serotec. RNAseB was obtained from New England Biolabs. 250 ng of antigen was coated onto flat bottom microtitre plates (Costar type 3690, Corning Inc.) at 4° C. overnight. All subsequent steps were performed at room temperature. The plates were washed 5 times with phosphate buffered saline containing 0.05% Tween-20 (PBS-T) then blocked with 5% non-fat milk in PBS-T (100 mL/well) for 1 h. The wells were emptied, and serial dilutions of antibody were added (5% non-fat milk in PBS-T) and incubated for 2 h. After washing, antibody binding was probed with either alkaline phosphatase-conjugated goat anti-human IgG Fc or peroxidase-conjugated rabbit-anti-goat H+L (Jackson, diluted to 1:1000 in 5% non-fat milk in PBS-T) for 1 h. The wells were washed and the bound secondary antibody was visualised with p-nitrophenol phosphate substrate (Sigma) or TMB substrate (Thermo Scientific) and read at 405 nm or 450 nm, respectively.

Generation of Pseudovirus.

Pseudovirus was generated in HEK 293T cells as described previously (63, 64). Briefly, 293T cells were transfected with plasmids carrying the reporter gene expressing the virus backbone PSG-3Aenv and the functional envelope clone at a ratio of 2:1 using Fugene (Roche) or PEI max (Polysciences, Inc) according to the manufacturer's instructions. Virus supernatants were harvested after 3 days. Glycosidase inhibitors were added at the time of transfection and were used at the following concentrations: 25 µM kifunensine and 2 mM N-butyldeoxynojirimycin (NB-DNJ) (65).

Neutralization Assays.

Neutralization activity of antibodies against pseudovirus in TZM-bl cells was determined as described previously (63, 64). Briefly, TZM-bl cells were seeded in a 96-well flat bottom plate and infected with pseudovirus in the presence of inhibitors (200 µl total volume). Viruses were preincubated with the antibody for 1 h at 37° C. Luciferase reporter gene expression was quantified 72 h after infection upon lysis and addition of Bright-Glo™ Luciferase substrate (Promega).

Cell Surface Binding Assays.

Titrating amounts of antibody were added to HIV-1 Env transfected 293T cells, incubated for 1 h at 37° C., washed with FACS buffer, and stained with a 1:200 dilution of goat anti-human IgG F(ab')2 conjugated to phycoerythrin (Jackson). Binding was analyzed using flow cytometry, and binding curves were generated by plotting the mean fluorescence intensity of antigen binding as a function of antibody concentration. A FACSArray plate reader (BD biosciences) was used for flow cytometric analysis and FlowJo software was used for data interpretation.

High-Mannose Array.

$Man_9GlcNAc_2$-oxime, $Man_4$-$(CH_2)_5$—$NH_2$, $Man_8GlcNAc_2Gly$ (66, 67) and $Man_9$-dendron (68) were printed in replicates of six onto NHS-activated glass slides at a concentration of 200 µM (69) using a MicroGridII contact microarray printing robot. Printing efficiency was determined by measuring ConA binding.

Binding of Antibody Mutants to High-Mannose Array.

PGT antibody (30 µg/mL in 3% BSA and 0.05% Tween-20 in PBS) was pre-complexed with goat-anti-human-Fcγ-R-PE (15 µg/mL, Jackson) for 10 min at room temperature. The sample was added to the glycan array and incubated at room temperature for 1 hour. The slides were washed sequentially in PBS/0.05% Tween-20, PBS and water. Arrays were scanned for R-PE fluorescence on a ProScanArray HT (PerkinElmer) confocal slide scanner at 70PMT90LP. Signal intensities were collected using Imagene (BioDiscovery) image analysis software and calculated using the mean intensity of 4 replicate spotted samples.

Neoglycolipid (NGL) Microarray Analyses.

The microarrays (designated N-glycan-related Array Set 1) consisted of NGLs prepared by reductive amination (70) or oxime ligation (71) (Table S5). These were robotically printed onto nitrocellulose-coated glass slides as described (72), each at two levels (2 and 5 fmol/spot) in duplicate. The binding assays (70) were performed at ambient temperature. The PGTs 127 and 128 were pre-complexed with biotinylated anti-human-IgG (Vector) at a 1:3 ratio, w/w, before applying onto the slides at a final concentration of 10 µg/ml. Biotinylated ConA (Vector) was tested at 0.5 µg/ml. Binding was detected with Alexa-Fluor 647 labelled streptavidin (Molecular Probes) at 1 µg/ml. Microarray data analysis was performed with dedicated software. Binding signals were oligosaccharide dose-related. Results at 5 fmol/spot with selected oligomannose NGLs (prepared by reductive amination) are in FIG. 9A, and the full data with the 50 NGLs are shown in Table S6. Included for comparison are the results with human 2G12 (Polymun Scientific) taken from an earlier experiment performed using a different version of microarrays (73). Antibody 2G12 was analyzed at 1:10000 dilution (without pre-complexation), and the binding was detected with biotinylated anti-human-IgG followed by Alexa-Fluor 647 labelled streptavidin.

Example 3: References and Notes

1. P. D. Kwong et al., Structure of an HIV gp120 envelope glycoprotein in complex with the CD4 receptor and a neutralizing human antibody. *Nature* 393, 648-659 (1998).
2. R. Wyatt, J. Sodroski, The HIV-1 envelope glycoproteins: fusogens, antigens, and immunogens. *Science* 280, 1884-1888 (1998).
3. E. J. Toone, Structure and energetics of protein-carbohydrate complexes. *Curr Opin Struct Biol* 4, 719-728 (1994).
4. D. A. Calarese et al., Antibody domain exchange is an immunological solution to carbohydrate cluster recognition. *Science* 300, 2065-2071 (2003).
5. L. M. Walker et al., Broad neutralization coverage of HIV by multiple highly potent antibodies. *Nature*, e-pub August 17 (2011).
6. L. M. Walker et al., Broad and potent neutralizing antibodies from an African donor reveal a new HIV-1 vaccine target. *Science* 326, 285-289 (2009).
7. X. Wu et al., Rational design of envelope identifies broadly neutralizing human monoclonal antibodies to HIV-1. *Science* 329, 856-861 (2010).
8. X. Wu et al., Focused Evolution of HIV-1 neutralizing antibodies revealed by structures and deep sequencing. *Science,* 333, 1593-1602 (2011).
9. J. M. Binley et al., Comprehensive cross-clade neutralization analysis of a panel of anti-human immunodeficiency virus type 1 monoclonal antibodies. *J Virol* 78, 13232-13252 (2004).
10. I. A. Wilson, R. L. Stanfield, A Trojan horse with a sweet tooth. *Nat Struct Biol* 2, 433-436 (1995).
11. P. C. Wilson et al., Somatic hypermutation introduces insertions and deletions into immunoglobulin V genes. *J Exp Med* 187, 59-70 (1998).
12. J. C. Krause et al., An insertion mutation that distorts antibody binding site architecture enhances function of a human antibody. *MBio* 2, e00345-00310 (2011).
13. Notably, it has been shown that a three-amino-acid insertion in the heavy-chain CDR H2 of the influenza virus-specific MAb 2D1 rearranges the antibody-combining site and enhances neutralization potency (12), demonstrating that somatically introduced amino-acid insertions may be a conserved molecular mechanism for increasing antibody potency against viral pathogens.
14. The eODmV3 was expressed in GnTI −/−deficient HEK 293S cells to mimic the oligomannose-type glycosylation of that domain within intact gp120.
15. Three canonical strand-pairing H-bonds are formed as well as an H-bond between V3 Asp325 and the backbone amide of $Asp^{H100d}$ (FIG. 2C). Ile323 also interacts with the CDR H1-H2 disulfide and with $Leu^{H100}$ in CDR H3, and Arg327 is located in close proximity to $Asp^{H100d}$.

Tyr$^{H100b}$ makes aromatic interaction with the Gly324-Asp325 peptide bond. Also, similar to many other anti-HIV bnMAbs, the PGT 128 CDR H3 loop is relatively long (19 amino acids), although not the longest seen to date for human Abs (31-32 residues fo the PGT 140 series (5))

16. R. L. Stanfield, M. K. Gorny, C. Williams, S. Zolla-Pazner, I. A. Wilson, Structural rationale for the broad neutralization of HIV-1 by human monoclonal antibody 447-52D. *Structure* 12, 193-204 (2004).

17. T. Zhou et al., Structural basis for broad and potent neutralization of HIV-1 by antibody VRC01. *Science* 329, 811-817 (2010).

18. S. Beddows et al., Construction and characterization of soluble, cleaved, and stabilized trimeric Env proteins based on HIV type 1 Env subtype A. *AIDS Res Hum Retroviruses* 22, 569-579 (2006).

19. J. M. Binley et al., A recombinant human immunodeficiency virus type 1 envelope glycoprotein complex stabilized by an intermolecular disulfide bond between the gp120 and gp41 subunits is an antigenic mimic of the trimeric virion-associated structure. *J Virol* 74, 627-643 (2000).

20. J. M. Binley et al., Enhancing the proteolytic maturation of human immunodeficiency virus type 1 envelope glycoproteins. *J Virol* 76, 2606-2616 (2002).

21. R. W. Sanders et al., Stabilization of the soluble, cleaved, trimeric form of the envelope glycoprotein complex of human immunodeficiency virus type 1. *J Virol* 76, 8875-8889 (2002).

22. A. Harris et al., Trimeric HIV-1 glycoprotein gp140 immunogens and native HIV-1 envelope glycoproteins display the same closed and open quaternary molecular architectures. *Proc Natl Acad Sci USA* 108, 11440-11445 (2011).

23. The HIV-1 664G trimer is based on the clade A strain KNH1144 and incorporates stabilizing mutations A501C, T605C, and I559P. Applicants have previously shown that trimers incorporating these stabilizing mutations are competent to undergo CD4-induced conformational changes akin to those observed in the native trimer (22).

24. P. W. Parren, D. R. Burton, The antiviral activity of antibodies in vitro and in vivo. *Adv Immunol* 77, 195-262 (2001).

25. P. W. Parren et al., Neutralization of human immunodeficiency virus type 1 by antibody to gp120 is determined primarily by occupancy of sites on the virion irrespective of epitope specificity. *J Virol* 72, 3512-3519 (1998).

26. P. Roben et al., Recognition properties of a panel of human recombinant Fab fragments to the CD4 binding site of gp120 that show differing abilities to neutralize human immunodeficiency virus type 1. *J Virol* 68, 4821-4828 (1994).

27. Q. J. Sattentau, J. P. Moore, Human immunodeficiency virus type 1 neutralization is determined by epitope exposure on the gp120 oligomer. *J Exp Med* 182, 185-196 (1995).

28. M. Pancera, R. Wyatt, Selective recognition of oligomeric HIV-1 primary isolate envelope glycoproteins by potently neutralizing ligands requires efficient precursor cleavage. *Virology* 332, 145-156 (2005).

29. HIV-1$_{JR-FL}$ is the only HIV isolate that has been shown to express a high proportion of fully cleaved Env trimers on the surface of transfected cells and was, therefore, selected for binding studies.

30. J. Liu, A. Bartesaghi, M. J. Borgnia, G. Sapiro, S. Subramaniam, Molecular architecture of native HIV-1 gp120 trimers. *Nature* 455, 109-113 (2008).

31. P. J. Klasse, Modeling how many envelope glycoprotein trimers per virion participate in human immunodeficiency virus infectivity and its neutralization by antibody. *Virology* 369, 245-262 (2007).

32. J. S. Klein, P. J. Bjorkman, Few and far between: how HIV may be evading antibody avidity. *PLoS pathogens* 6, e1000908 (2010).

33. J. S. Klein et al., Examination of the contributions of size and avidity to the neutralization mechanisms of the anti-HIV antibodies b12 and 4E10. *Proc Natl Acad Sci USA* 106, 7385-7390 (2009).

34. C. Ansarah-Sobrinho, S. Nelson, C. A. Jost, S. S. Whitehead, T. C. Pierson, Temperature-dependent production of pseudoinfectious dengue reporter virus particles by complementation. *Virology* 381, 67-74 (2008).

35. S. P. Layne et al., Factors underlying spontaneous inactivation and susceptibility to neutralization of human immunodeficiency virus. *Virology* 189, 695-714 (1992).

36. J. M. Le Doux, H. E. Davis, J. R. Morgan, M. L. Yarmush, Kinetics of retrovirus production and decay. *Biotechnol Bioeng* 63, 654-662 (1999).

37. K. A. Dowd, C. A. Jost, A. P. Durbin, S. S. Whitehead, T. C. Pierson, A dynamic landscape for antibody binding modulates antibody-mediated neutralization of west nile virus. *PLoS pathogens* 7, e1002111 (2011).

38. C. R. Ruprecht et al., MPER-specific antibodies induce gp120 shedding and irreversibly neutralize HIV-1. *J Exp Med* 208, 439-454 (2011).

39. H. Haim et al., Soluble CD4 and CD4-mimetic compounds inhibit HIV-1 infection by induction of a short-lived activated state. *PLoS pathogens* 5, e1000360 (2009).

40. E. S. Gray et al., The neutralization breadth of HIV-1 develops incrementally over four years and is associated with CD4+ T cell decline and high viral load during acute infection. *Journal of virology* 85, 4828-4840 (2011).

41. L. M. Walker et al., A limited number of antibody specificities mediate broad and potent serum neutralization in selected HIV-1 infected individuals. *PLoS Pathog* 6, (2010).

42. H. Tang et al., Epitopes Immediately Below the Base of the V3 Loop of gp120 as Targets for the Initial Autologous Neutralizing Antibody Response in Two HIV-1 Subtype B-Infected Individuals. *J Virol.* 85, 9286-9299 (2011).

43. A. Nandi et al., Epitopes for broad and potent neutralizing antibody responses during chronic infection with human immunodeficiency virus type 1. *Virology* 392, 339-348 (2010).

44. R. Pejchal et al., Structure and function of broadly reactive antibody PG16 reveal an H3 subdomain that mediates potent neutralization of HIV-1. *Proc. Natl. Acad. Sci. USA,* 107, 11483-11488 (2010).

45. P. J. Reeves, N. Callewaert, R. Contreras, H. G. Khorana, Structure and function in rhodopsin: high-level expression of rhodopsin with restricted and homogeneous N-glycosylation by a tetracycline-inducible N-acetylglucosaminyltransferase I-negative HEK293S stable mammalian cell line. *Proc. Natl. Acad. Sci. USA* 99, 13419-13424 (2002).

46. E. Folta-Stogniew, Oligomeric states of proteins determined by size-exclusion chromatography coupled with light scattering, absorbance, and refractive index detectors. *Methods Mol. Biol.* 328, 97-112 (2006).

47. H. K. Lee et al., Reactivity-based one-pot synthesis of oligomannoses: defining antigens recognized by 2G12, a broadly neutralizing anti-HIV-1 antibody. *Angew. Chem. Int. Ed. Engl.* 43, 1000-1003 (2004).
48. A. J. McCoy et al., Phaser crystallographic software. *J. Appl. Crystallogr.* 40, 658-674 (2007).
49. The CCP4 suite: programs for protein crystallography. *Acta. Crystallogr. D Biol. Crystallogr.* 50, 760-763 (1994).
50. S. Duquerroy et al., Crystal structure of a human autoimmune complex between IgM rheumatoid factor RF61 and IgG1 Fc reveals a novel epitope and evidence for affinity maturation. *J. Mol. Biol.* 368, 1321-1331 (2007).
51. P. D. Adams et al., PHENIX: building new software for automated crystallographic structure determination. *Acta Crystallogr. D Biol. Crystallogr.* 58, 1948-1954 (2002).
52. P. Emsley, K. Cowtan, Coot: model-building tools for molecular graphics. *Acta Crystallogr. D Biol. Crystallogr.* 60, 2126-2132 (2004).
53. E. Blanc et al., Refinement of severely incomplete structures with maximum likelihood in BUSTER-TNT. *Acta Crystallogr. D Biol. Crystallogr.* 60, 2210-2221 (2004).
54. M. Strong et al., Toward the structural genomics of complexes: crystal structure of a PE/PPE protein complex from *Mycobacterium tuberculosis*. *Proc. Natl. Acad. Sci. USA* 103, 8060-8065 (2006).
55. Z. Otwinowski, W. Minor, Processing of x-ray diffraction data collected in oscillation mode. *Methods Enzymol.* 276, 307-326 (1997).
56. B. DeLaBarre, A. T. Brunger, Considerations for the refinement of low-resolution crystal structures. *Acta Crystallogr. D Biol. Crystallogr.* 62, 923-932 (2006).
57. G. C. Lander et al., Appion: an integrated, database-driven pipeline to facilitate EM image processing. *J. Struct. Biol.* 166, 95-102 (2009).
58. N. R. Voss, C. K. Yoshioka, M. Radermacher, C. S. Potter, B. Carragher, DoG Picker and TiltPicker: software tools to facilitate particle selection in single particle electron microscopy. *J. Struct. Biol.* 166, 205-213 (2009).
59. J. A. Mindell, N. Grigorieff, Accurate determination of local defocus and specimen tilt in electron microscopy. *J. Struct. Biol.* 142, 334-347 (2003).
60. M. Hohn et al., SPARX, a new environment for Cryo-EM image processing. *J. Struct. Biol.* 157, 47-55 (2007).
61. G. Tang et al., EMAN2: an extensible image processing suite for electron microscopy. *J. Struct. Biol.* 157, 38-46 (2007).
62. S. J. Ludtke, P. R. Baldwin, W. Chiu, EMAN: semiautomated software for high-resolution single-particle reconstructions. *J. Struct. Biol.* 128, 82-97 (1999).
63. M. Li et al., Human immunodeficiency virus type 1 env clones from acute and early subtype B infections for standardized assessments of vaccine-elicited neutralizing antibodies. *J. Virol.* 79, 10108-10125 (2005).
64. D. C. Montefiori, Evaluating neutralizing antibodies against HIV, SIV, and SHIV in luciferase reporter gene assays. *Curr. Protoc. Immunol.* Chapter 12, Unit 12 11 (2005).
65. K. J. Doores et al., Variable loop glycan dependency of the broad and potent HIV-1-neutralizing antibodies PG9 and PG16. *J. Virol.* 84, 10510-10521(2010).
66. I. Matsuo, Y. Ito, Synthesis of an octamannosyled glycan chain, the key oligosaccharide structure in ER-associated degradation. *Carbohydr. Res.* 338, 2163-2168 (2003).
67. K. Totani, I. Matsuo, Y. Ihara, Y. Ito, High-mannose-type glycan modifications of dihydrofolate reductase using glycan-methotrexate conjugates. *Bioorg. Med. Chem.* 14, 5220-5229 (2006).
68. S. K. Wang et al., Targeting the carbohydrates on HIV-1: Interaction of oligomannose dendrons with human monoclonal antibody 2G12 and DC-SIGN. *Proc. Natl. Acad. Sci. USA* 105, 3690-3695 (2008).
69. O. Blixt et al., Printed covalent glycan array for ligand profiling of diverse glycan binding proteins. *Proc. Natl. Acad. Sci.* 101, 17033-17038 (2004).
70. W. Chai, M. S. Stoll, C. Galustian, A. M. Lawson, T. Feizi, Neoglycolipid technology: deciphering information content of glycome. *Methods Enzymol.* 362, 160-195 (2003).
71. Y. Liu et al., Neoglycolipid probes prepared via oxime ligation for microarray analysis of oligosaccharide-protein interactions. *Chem. Biol.* 14, 847-859 (2007).
72. A. S. Palma et al., Ligands for the beta-glucan receptor, Dectin-1, assigned using "designer" microarrays of oligosaccharide probes (neoglycolipids) generated from glucan polysaccharides. *J. Biol. Chem.* 281, 5771-5779 (2006).
73. D. C. Dunlop et al., Polysaccharide mimicry of the epitope of the broadly neutralizing anti-HIV antibody, 2G12, induces enhanced antibody responses to self oligomannose glycans. *Glycobiology* 20, 812-823 (2010).
74. A. J. Petrescu, S. M. Petrescu, R. A. Dwek, M. R. Wormald, A statistical analysis of N- and O-glycan linkage conformations from crystallographic data. *Glycobiology* 9, 343-352 (1999).
75. T. Lutteke, M. Frank, C. W. von der Lieth, Carbohydrate Structure Suite (CSS): analysis of carbohydrate 3D structures derived from the PDB. *Nucleic Acids Res.* 33, D242-246 (2005).
76. T. Zhou et al., Structural definition of a conserved neutralization epitope on HIV-1 gp120. *Nature* 445, 732-737 (2007).
77. S. Sheriff, W. A. Hendrickson, J. L. Smith, Structure of myohemerythrin in the azidomet state at 1.7/1.3 Å resolution. *J. Mol. Biol.* 197, 273-296 (1987).
78. M. L. Connolly, The molecular surface package. *J. Mol. Graph.* 11, 139-141 (1993).

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A polypeptide comprising SEQ ID NO: 1.

2. The polypeptide of claim 1 further comprising one or more glycans.

3. The polypeptide of claim 2 wherein a glycan is $Man_{8/9}GlcNAc_2$.

4. The polypeptide of claim 3 wherein the glycan is attached to N332.

5. The polypeptide of claim 2 a glycan is $Man_5GlcNAc_2$.

6. The polypeptide of claim 5 wherein the glycan is attached to N301.

7. A composition comprising the polypeptide of claim 1, wherein the composition elicits an anti-HIV-1 antibody.

8. A method for eliciting an immunogenic or immunological response, wherein the method comprises administering the composition of claim 7 to an animal that generates antibodies to the composition, collecting a sample from the animal comprising the antibodies, and detecting the presence of anti-HIV antibodies in the sample.

9. A method of generating an anti-HIV immune response comprising administering to an animal capable of eliciting antibodies the composition of claim 7.

10. A method for detecting anti-HIV antibodies comprising contacting a sample suspected of having such antibodies with the composition of claim 7 and detecting antigen-antibody binding activity using ELISA.

* * * * *

SEQUENCE LISTING

```
<160> NUMBER OF SEQ ID NOS: 12

<210> SEQ ID NO 1
<211> LENGTH: 24
<212> TYPE: PRT
```

```
<213> ORGANISM: Human immunodeficiency virus

<400> SEQUENCE: 1

Asn Cys Thr Arg Pro Asn Asn Asn Thr Arg Pro Gly Glu Ile Ile Gly
1               5                   10                  15
Asp Ile Arg Gln Ala His Cys Asn
            20

<210> SEQ ID NO 2
<211> LENGTH: 6
<212> TYPE: PRT
<213> ORGANISM: Homo sapiens

<400> SEQUENCE: 2

Arg Ser Tyr Tyr Asn Thr
1               5

<210> SEQ ID NO 3
<211> LENGTH: 6
<212> TYPE: PRT
<213> ORGANISM: Homo sapiens

<400> SEQUENCE: 3

Ala Ser Tyr Trp Asn Arg
1               5

<210> SEQ ID NO 4
<211> LENGTH: 5
<212> TYPE: PRT
<213> ORGANISM: Homo sapiens

<400> SEQUENCE: 4

Val Gly Asn Trp Asp
1               5

<210> SEQ ID NO 5
<211> LENGTH: 5
<212> TYPE: PRT
<213> ORGANISM: Homo sapiens

<400> SEQUENCE: 5

Asp Trp Thr Tyr His
1               5

<210> SEQ ID NO 6
<211> LENGTH: 8
<212> TYPE: PRT
<213> ORGANISM: Homo sapiens

<400> SEQUENCE: 6

Trp Asn Arg Gly Trp Thr Tyr His
1               5

<210> SEQ ID NO 7
<211> LENGTH: 6
<212> TYPE: PRT
<213> ORGANISM: Homo sapiens

<400> SEQUENCE: 7

Ile Ile Gly Asp Ile Arg
1               5

<210> SEQ ID NO 8
<211> LENGTH: 13
```

```
<212> TYPE: PRT
<213> ORGANISM: Homo sapiens

<400> SEQUENCE: 8

His Cys Ala Ser Tyr Trp Asn Arg Gly Trp Thr Tyr His
1               5                   10

<210> SEQ ID NO 9
<211> LENGTH: 4
<212> TYPE: PRT
<213> ORGANISM: Homo sapiens

<400> SEQUENCE: 9

Thr Pro Lys Asn
1

<210> SEQ ID NO 10
<211> LENGTH: 6
<212> TYPE: PRT
<213> ORGANISM: Homo sapiens

<400> SEQUENCE: 10

Leu Arg Tyr Thr Asp Trp
1               5

<210> SEQ ID NO 11
<211> LENGTH: 4
<212> TYPE: PRT
<213> ORGANISM: Homo sapiens

<400> SEQUENCE: 11

Trp Thr Tyr His
1

<210> SEQ ID NO 12
<211> LENGTH: 190
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Gly Asn Ser Asn
            20                  25                  30

Asn Glu Ser Glu Ile Phe Arg Pro Gly Gly Gly Asp Met Arg Asp Ile
        35                  40                  45

Ala Arg Cys Gln Ile Ala Gly Thr Val Val Ser Thr Gln Leu Leu Leu
    50                  55                  60

Asn Gly Ser Leu Ala Glu Glu Val Val Ile Arg Ser Val Asn Phe
65                  70                  75                  80

Thr Asp Asn Ala Lys Ser Ile Cys Val Gln Leu Asn Thr Ser Val Glu
                85                  90                  95

Ile Asn Cys Thr Arg Pro Asn Asn Asn Thr Arg Pro Gly Glu Ile Ile
            100                 105                 110

Gly Asp Ile Arg Gln Ala His Cys Asn Ile Ser Arg Ala Lys Trp Asn
        115                 120                 125

Asn Thr Leu Lys Gln Ile Ala Ser Lys Leu Arg Glu Gln Phe Gly Asn
    130                 135                 140
```

-continued

```
Asn Lys Thr Ile Ile Phe Lys Gln Ser Ser Gly Gly Asp Pro Glu Ile
145                 150                 155                 160

Val Thr His Ser Phe Asn Cys Gly Gly Glu Phe Phe Tyr Cys Asp Ser
            165                 170                 175

Thr Gln Leu Phe Asn Ser Thr Trp Phe Asn Ser Thr Trp Ser
            180                 185                 190
```